United States Patent
Boeke et al.

(10) Patent No.: US 11,667,962 B2
(45) Date of Patent: Jun. 6, 2023

(54) METHODS AND COMPOSITIONS FOR RAPID AND HIGH THROUGHPUT DIAGNOSIS

(71) Applicants: Opentrons Labworks Inc., Brooklyn, NY (US); New York University, New York, NY (US)

(72) Inventors: Jef D. Boeke, New York, NY (US); Jon Laurent, Brooklyn, NY (US); Andrew Martin, Brooklyn, NY (US); Paolo Mita, Brooklyn, NY (US)

(73) Assignees: Opentrons Labworks Inc., Brooklyn, NY (US); New York University, New York, NY (US)

( * ) Notice: Subject to any disclaimer, the term of this patent is extended or adjusted under 35 U.S.C. 154(b) by 0 days.

(21) Appl. No.: 17/478,415

(22) Filed: Sep. 17, 2021

(65) Prior Publication Data
US 2022/0090186 A1    Mar. 24, 2022

Related U.S. Application Data

(60) Provisional application No. 63/080,556, filed on Sep. 18, 2020, provisional application No. 63/139,601, filed on Jan. 20, 2021.

(51) Int. Cl.
*C12Q 1/68* (2018.01)
*C12Q 1/6848* (2018.01)
*C12Q 1/70* (2006.01)

(52) U.S. Cl.
CPC .......... *C12Q 1/6848* (2013.01); *C12Q 1/701* (2013.01)

(58) Field of Classification Search
None
See application file for complete search history.

(56) References Cited

U.S. PATENT DOCUMENTS

| 2018/0087078 A1* | 3/2018 | Weitz ............... C12N 15/1065 |
| 2020/0200779 A1 | 6/2020 | Sigler et al. |
| 2020/0246976 A1 | 8/2020 | Chau et al. |

FOREIGN PATENT DOCUMENTS

| AU | 2015200465 A1 | 2/2015 | |
| WO | WO-2005029041 A2 * | 3/2005 | .......... B01L 3/50851 |

OTHER PUBLICATIONS

Huang et al. (Scientific Reports, 2014, p. 1-9) (Year: 2014).*
Anderson et al. (Curr Protoc Microbiol, 2018, 51(1):e62, p. 1-25) (Year: 2018).*
Hussain et al. (J of Pharm and Biomed Anal, 2016, 123:128-131) (Year: 2016).*
Batéjat, C, et al. "Heat inactivation of the Severe Acute Respiratory Syndrome" Coronavirus 2 [Preprint] bioRxiv. May 1, 2020; doi: 10.1101/2020.05.01.067769.
"CDC 2019—Novel Coronavirus (2019—nCoV) Real-Time RT-PCR Diagnostic Panel; For Emergency Use Only; Instructions for Use", Jul. 21, 2021.
Kampf, G., et al., "Inactivation of coronaviruses by heat" pii: S0195-6701 J Hosp Infect (Mar. 31, 2020), doi: 10.1016/j.jhin.2020. 03.025S0195-6701 (20)30124-9.
Lieberman, JA, et al. "Comparison of Commercially Available and Laboratory-Developed Assays for In Vitro Detection of SARS-CoV-2 in Clinical Laboratories" J Clin Microbiol. Jul. 23, 2020;58(8):e00821-20. doi: 10.1128/JCM.00821-20. PMID: 32350048; PMCID: PMC7383518.
Research Use Only 2019—Novel Coronavirus (2019—nCoV) Real-time RT-PCR Primers and Probes:, May 29, 2020.
Vogels, C.B.F., et al., "Analytical sensitivity and efficiency comparisons of SARS-CoV-2 RT-qPCR primer-probe sets" Nat Microbiol (2020). https://doi.org/10.1038/s41564-020-0761-6.
Wyllie, et al., "Saliva is more sensitive for SARS-CoV-2 detection in COVID-19 patients than nasopharyngeal swabs" (2020) Yale School of Medicine p. 1-12.
Yang, et al., "Evaluating the accuracy of different respiratory specimens in the laboratory diagnosis and monitoring the viral shedding of 2019-nCoV infections" (2020) Institut Pasteur of Shanghai, Chinese Academy of Sciences, pp. 1-17.
"International Search Report and Written Opinion for PCT Application No. PCT/US2021/050946 dated Dec. 2, 2021".
"Tewhey, et al., "Microdroplet-based PCR amplification for large scale targeted sequencing" Nat Biotechnol. (Nov. 1, 2009) 27(11): 1025-1031".

* cited by examiner

*Primary Examiner* — Stephanie K Mummert
(74) *Attorney, Agent, or Firm* — Wilson Sonsini Goodrich & Rosati

(57) ABSTRACT

Provided herein are methods and compositions for diagnosing a disease or an infection in a high throughput manner. Also provided herein are methods and compositions for diagnosing a disease or an infection with high specificity and high sensitivity.

14 Claims, 18 Drawing Sheets
Specification includes a Sequence Listing.

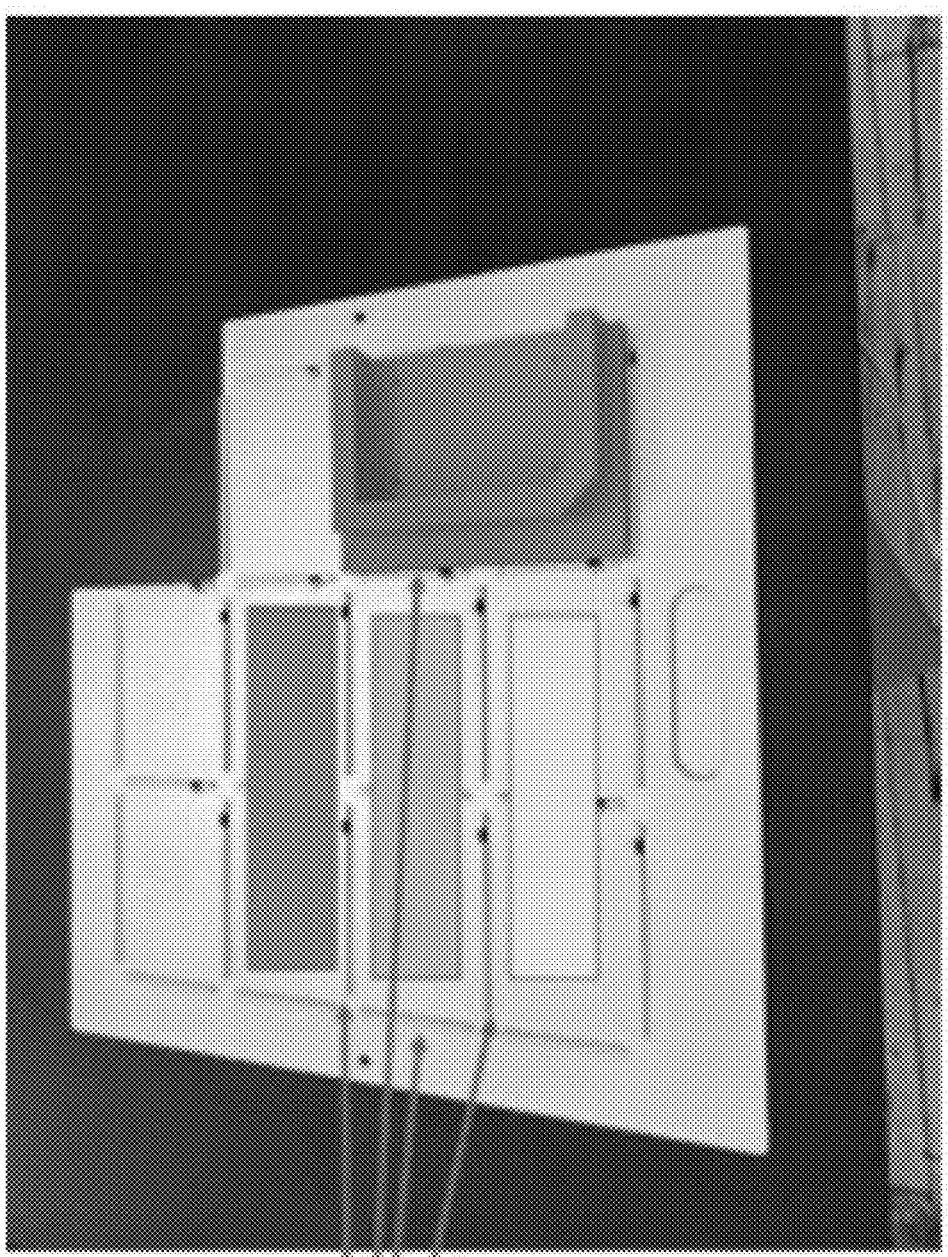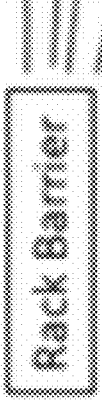
Figure 2H

ReOpen Rack to 96 Deep Well Plate Mapping

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | vol/well | | amount shot | |
|---|---|---|---|---|---|---|---|---|---|---|---|---|---|---|---|---|---|---|---|---|---|---|---|---|---|---|---|---|
| | | | | | | | | | | | | Primer + Probe + Controls (PPC plate) | | | | | | | | | | | | | | | | |
| A | water | water | water | water | water | water | water | water | water | water | water | water | water | water | water | water | water | water | water | water | water | water | water | water | | | 70 nl | N1-fam |
| B | water | water | water | water | water | water | water | water | water | water | water | water | water | water | water | water | water | water | water | water | water | water | water | water | | | 45 nl | N2-hex |
| C | water | water | | | | | | | N1 | N1 | N1 | N1 | N1 | N1 | N1 | N1 | N1 | | | | | water | water | water | 45 | | 20 nl | RP-cy5 |
| D | water | water | | | | | | | N2 | N2 | N2 | N2 | N2 | N2 | N2 | N2 | N2 | | | | | water | water | water | 35 | | | |
| E | water | water | | | | | | | RP | RP | RP | RP | RP | RP | RP | RP | RP | | | | | water | water | water | 25 | | | |
| F | water | water | | | | | | | N1 | N1 | N1 | N1 | N1 | N1 | N1 | N1 | N1 | | | | | water | water | water | 45 | | | |
| G | water | water | | | | | | | N2 | N2 | N2 | N2 | N2 | N2 | N2 | N2 | N2 | | | | | water | water | water | 35 | | | |
| H | water | water | | | | | | | RP | RP | RP | RP | RP | RP | RP | RP | RP | | | | | water | water | water | 25 | | | |
| I | water | water | | | | | | | | | | | | | | | | | | | | water | water | water | | | controls | |
| J | water | water | | | | | | | C1 | C1 | C1 | C1 | C1 | C1 | C1 | C1 | | | | | | water | water | water | 30 | | | H2O |
| K | water | water | | | | | | | C2 | C2 | C2 | C2 | C2 | C2 | C2 | C2 | | | | | | water | water | water | 30 | | C1 | 16c/μl+RP1k c/μl |
| L | water | water | | | | | | | C3 | C3 | C3 | C3 | C3 | C3 | C3 | C3 | | | | | | water | water | water | 30 | | C2 | 3.2c/μl+RP1k c/μl |
| M | water | water | | | | | | | C4 | C4 | C4 | C4 | C4 | C4 | C4 | C4 | | | | | | water | water | water | 30 | | C3 | 0.64c/μl+RP1k c/μl |
| N | water | water | | | | | | | | | | | | | | | | | | | | water | water | water | | | C4 | |
| O | water | water | water | water | water | water | water | water | water | water | water | water | water | water | water | water | water | water | water | water | water | water | water | water | | | | |
| P | water | water | water | water | water | water | water | water | water | water | water | water | water | water | water | water | water | water | water | water | water | water | water | water | | | | |

100 μl in each "water" well

Figure 3C

| | SCOV2 dilutions-> | 1 | 1/2 | 1/4 | 1/8 | 1/16 | 1/32 | 1/64 | 1/128 | 1/256 | 1/512 | 1/1024 |
|---|---|---|---|---|---|---|---|---|---|---|---|---|
| Dispensed with Echo | #positive over 32 | 32 | 32 | 32 | 30 | 22 | 11 | 9 | 8 | 2 | 1 | 1 |
| | %positives | 100 | 100 | 100 | 93.8 | 68.8 | 34.4 | 28.1 | 25 | 6.25 | 3.13 | 3.13 |
| Mixed in MM | #positive over 32 | 32 | 32 | 32 | 25 | 15 | 17 | 4 | 1 | 2 | 5 | 0 |
| | %positives | 100 | 100 | 100 | 78.1 | 46.9 | 53.1 | 12.5 | 3.13 | 6.25 | 15.6 | 0 |

Figure 12

| LoD analysis | RNA copy/μL | 32.0 | 21.3 | 16.0 | 10.7 | 8.0 | 5.3 | 4.0 | 2.7 | 2.0 | 1.3 | 1.0 | 0.7 | 0.5 | 0.3 | 0.25 | 0.17 | 0.13 | 0.08 | 0.05 | 0.04 | 0.03 | 0.03 | 0.02 | 0.0 |
|---|---|---|---|---|---|---|---|---|---|---|---|---|---|---|---|---|---|---|---|---|---|---|---|---|---|
| | #positive over 64 | 64 | 64 | 64 | 64 | 64 | 64 | 64 | 64 | 62 | 63 | 55 | 55 | 39 | 40 | 21 | 24 | 16 | 19 | 12 | 4 | 5 | 0 | | |
| | %positives | 100 | 100 | 100 | 100 | 100 | 100 | 100 | 100 | 96.9 | 98.4 | 85.9 | 85.9 | 60.9 | 62.5 | 32.8 | 37.5 | 25 | 29.7 | 18.8 | 6.25 | 7.81 | 0 | | |
| N1 (Ct values) | Mean | 31.6 | 32.2 | 32.5 | 33.2 | 33.6 | 34.2 | 34.7 | 35.2 | 35.8 | 36.2 | 36.7 | 37 | 37.3 | 37.4 | 37.6 | 38 | 37.7 | 38.1 | 38.5 | 37.9 | 38.1 | | | |
| | Std. Deviation | 0.19 | 0.21 | 0.3 | 0.3 | 0.38 | 0.42 | 0.63 | 0.65 | 0.87 | 0.8 | 1 | 1.22 | 0.94 | 0.83 | 0.66 | 0.75 | 0.99 | 0.45 | 0.87 | 2.23 | 0.54 | 0.73 | | |
| | Std. Error of Mean | 0.02 | 0.03 | 0.04 | 0.04 | 0.05 | 0.05 | 0.08 | 0.08 | 0.11 | 0.1 | 0.13 | 0.17 | 0.13 | 0.14 | 0.11 | 0.18 | 0.22 | 0.11 | 0.21 | 0.67 | 0.27 | 0.37 | | |
| N2 (Ct values) | Mean | 32 | 32.5 | 32.9 | 33.6 | 33.9 | 34.6 | 35.1 | 35.6 | 36.2 | 36.6 | 37.2 | 37.5 | 37.8 | 38.1 | 38.2 | 38.4 | 38.2 | 38.5 | 38.8 | 39 | 40 | 38.6 | | |
| | Std. Deviation | 0.17 | 0.19 | 0.27 | 0.3 | 0.34 | 0.42 | 0.5 | 0.68 | 0.86 | 0.93 | 1 | 1.23 | 0.96 | 1.17 | 0.7 | 0.85 | 1.02 | 0.4 | 1.24 | 1.92 | 3.42 | 0.15 | | |
| | Std. Error of Mean | 0.02 | 0.02 | 0.03 | 0.04 | 0.04 | 0.05 | 0.06 | 0.09 | 0.11 | 0.12 | 0.13 | 0.17 | 0.13 | 0.19 | 0.12 | 0.2 | 0.21 | 0.1 | 0.31 | 0.56 | 1.71 | 0.08 | | |
| RP (Ct values) | Mean | 33.1 | 33.2 | 33.2 | 33.2 | 33.2 | 33.2 | 33.2 | 33.2 | 33.1 | 33.1 | 33.1 | 33.1 | 33.1 | 33.1 | 33.1 | 33 | 33.1 | 33.1 | 33.1 | 33.1 | 33.1 | 33.1 | 33.1 | |
| | Std. Deviation | 0.24 | 0.25 | 0.24 | 0.28 | 0.29 | 0.29 | 0.31 | 0.3 | 0.32 | 0.28 | 0.28 | 0.28 | 0.3 | 0.38 | 0.26 | 0.32 | 0.31 | 0.3 | 0.3 | 0.31 | 0.29 | 0.28 | 0.3 | |
| | Std. Error of Mean | 0.03 | 0.03 | 0.03 | 0.03 | 0.04 | 0.04 | 0.04 | 0.04 | 0.04 | 0.04 | 0.04 | 0.03 | 0.04 | 0.05 | 0.03 | 0.04 | 0.04 | 0.04 | 0.04 | 0.04 | 0.04 | 0.03 | 0.03 | |

Figure 13

METHODS AND COMPOSITIONS FOR RAPID AND HIGH THROUGHPUT DIAGNOSIS

CROSS REFERENCE

This application claims the benefit of U.S. Provisional Application No. 63/080,556, filed on Sep. 18, 2020, and U.S. Provisional Application No. 63/139,601, filed on Jan. 20, 2021, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Sep. 17, 2021, is named 59725-701_201_SL.txt and is 2,360 bytes in size.

BACKGROUND

Rapid and accurate diagnostic tools for detecting pathogens are important for timely patient diagnosis and intervention for infectious diseases. Polymerase chain reaction (PCR)-based methods are currently the most well-developed molecular techniques with a wide range of clinical applications including specific or broad-spectrum pathogen detection, evaluation of emerging novel infections, surveillance, early detection of biothreat agents, and antimicrobial resistance profiling. The recent outbreak of severe acute respiratory syndrome coronavirus 2 (SARS-CoV-2) that led to a global pandemic emphasizes the importance of rapid and high throughput diagnostics for early and informed decision-making related to infection control, patient isolation and treatment with very critical consequences for patients, health providers, and the public. There is a need to further advance the currently available diagnostic tools and develop more rapid, high throughput, and automated molecular diagnostics platform with high detection sensitivity, high specificity, high accuracy, and expanded capacity.

SUMMARY

In some aspects, provided herein is a method of detecting a target nucleic acid sequence in a sample with or without a fluorescence labelled probe, said method comprising contacting said sample with at least one microdroplet comprising a pair of primers, wherein said at least one microdroplet contains a volume of equal to or less than 250 nL, and amplifying said target nucleic acid sequence in said sample, thereby detecting said target nucleic acid sequence in said sample.

In another aspect, provided herein, is a method of amplifying a target nucleic acid sequence in a sample, said method comprising preparing a reaction pre-mixture comprising said sample and a polymerase, wherein said reaction pre-mixture does not comprise a primer, contacting said reaction pre-mixture with a microdroplet comprising a pair of primers to form a reaction mixture, wherein said microdroplet contains a volume of equal to or less than 250 nL, and amplifying said target nucleic acid sequence by thermal cycling in said reaction mixture, wherein said amplification has a lower limit of detection (LoD) as compared to an amplification by thermal cycling in a reaction mixture comprising a sample, a polymerase, and a pair of primers that are pre-mixed prior to amplification.

In some aspects, provided herein is a method of amplifying a target nucleic acid sequence in a plurality of samples, said method comprising: amplifying said target nucleic acid in each of said plurality of samples in a reaction mixture, wherein when said reaction mixture contains a volume of equal to or less than 10 µL, said amplification has a limit of detection (LoD) of 1000 molecules per mL, wherein said LoD is determined by a lowest concentration of the target nucleic acid that allows amplification to be detected when amplified in a plurality of positive control samples each having the lowest concentration of the target nucleic acid sequence, wherein amplification is detected in at least 95% of the plurality of the positive controls.

In some aspects, provided herein is a method of amplifying a target nucleic acid sequence in a plurality of samples, said method comprising: amplifying said target nucleic acid in each of said plurality of samples in a reaction mixture, wherein when said reaction mixture contains a volume of equal to or less than 10 µL, said amplification has a limit of detection (LoD) of 3000 molecules per mL, as measured by amplification with serially diluted positive controls.

In some aspects, provided herein is a method of detecting a target nucleic acid sequence in a plurality of samples at a rate of at least 10000 samples per day with a single device, said method comprising contacting each of said plurality of samples with a pair of primers and amplifying said target nucleic acid sequence in each of said plurality of samples, thereby detecting said target nucleic acid sequence in each of said plurality of samples, wherein said detection has a sensitivity of at least 95% as calibrated with a positive control.

In some aspects, provided herein is a method for simultaneously detecting two or more target nucleic acid sequences in a plurality of samples at a rate of at least 10000 samples per day in a single device, said method comprising contacting said plurality of samples with two or more pairs of primers on a plate comprising a plurality of wells, wherein each well comprises one of said plurality of samples and one pair of said two or more pairs of primers, wherein each one pair of said two or more pairs of primers hybridizes with one of said two or more target nucleic acid sequences, wherein said plurality of wells comprise different pairs of said two or more pairs of primers, and amplifying one of said two or more target nucleic acid sequences in each well to a threshold level, thereby detecting said two or more target nucleic acid sequences in said plurality of samples, wherein said amplification of said detection has a sensitivity of at least 95% as calibrated with a positive control.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2H shows an image depicting the placement of a Manual Reformatting Adapter on the OT-2 deck.

FIG. 3A shows a diagram depicting the arrangement of samples on 96 well plates.

FIG. 3B shows a diagram depicting the arrangement of controls on a 96 well plate.

FIG. 3C shows a diagram depicting the arrangement of primers and probes on a 96 well plate.

FIG. 12 shows a table comparing the number and % positive reaction of SCV2 tests performed with primers and probes separately dispensed with Echo and SCV2 tests performed with primers and probes mixed into the master mix (MM).

FIG. 13 shows a table demonstrating the results of PCR Limit of Detection (LoD) analysis.

DETAILED DESCRIPTION

Figure 1:
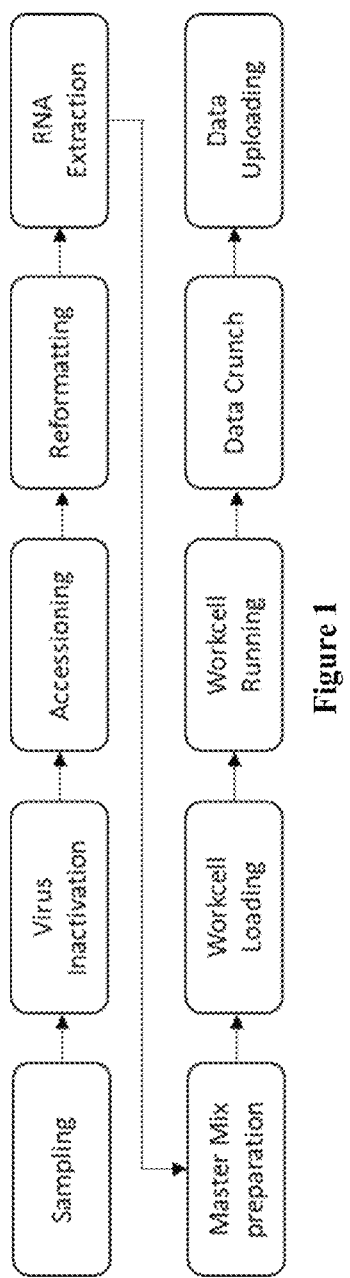
FIG. 1 depicts a schematic of an exemplary workflow.

Provided herein are methods, compositions, and devices for producing polynucleotides using microfluidic workflow that can allow for rapid, highly efficient, accurate, and pure RNA generation. The methods, compositions, and devices described herein provide means to synthesize polynucleotides using an efficient RNA polymerase enzyme, microfluidics, enhanced kinetics, and reduced off-target effects. In some aspects, the methods, compositions, and devices described herein provide single unit cartridge-based portable systems for polynucleotide synthesis.

Definitions

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

Certain specific details of this description are set forth in order to provide a thorough understanding of various embodiments. However, one skilled in the art will understand that the present disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods, and materials are described below.

Diagnostic System

Provided herein are methods and compositions for diagnosing a disease or an infection in a high throughput manner using, for example, a method to amplify a target nucleic acid, including polymerase chain reaction (PCR), quantitative or real-time PCR (qPCR), reverse transcription-PCR (RT-PCR), and/or quantitative or real-time RT-PCR (rRT-PCR or RT-qPCR) at robot-driven working stations. Also provided herein are methods and compositions for diagnosing a disease or an infection in a high throughput manner with high specificity and high sensitivity. Further provided herein are methods and compositions for simultaneously diagnosing two or more diseases or infections in a high throughput manner in a single device using, for example, polymerase chain reaction (PCR), quantitative PCR (qPCR), reverse transcription-PCR (RT-PCR), and/or real-time RT-PCR (rRT-PCR). The reactions can be conducted at robot-driven working stations. The methods and compositions provided herein can be applied to a wide range of PCR or RT-PCR based tests for viral infections (e.g., DNA or RNA virus), bacterial infections, fungal infections, or parasite infections. For example, the method and compositions provided herein can be applied to tests for, including, but not limited to, Covid19 caused by severe acute respiratory syndrome coronavirus 2 (SARS-CoV-2). Other viral infections that can be detected by a method disclosed herein include, but are not limited to, DNA or RNA viral infections such as hepatitis B, adenovirus, papillomavirus, poxvirus, herpesvirus, herpes simplex virus, varicella zoster virus, Epstein-Barr virus, cytomegalovirus, human immunodeficiency virus (HIV), influenza virus, Dengue virus, hepatitis C virus, hepatitis E virus, ebolavirus, lyssavirus, poliovirus, West Nile virus, Human T-cell lymphotropic virus type 1 (HTLV-1), respiratory syncytial virus (RSV), parainfluenza virus (Hy), human metapneumovirus (hMPV), human rhinovirus (HRV), severe acute respiratory syndrome coronavirus 1 (SARS-CoV-1), middle east respiratory syndrome coronavirus (MERS-CoV), and measles virus. Provided herein are methods and compositions for isolating nucleic acids in high purity from a wide variety of samples, e.g., a biological sample obtained from a subject.

An example diagnosis workflow can be as follows (FIG. 1). First, nasal and/or oral swab samples (e.g., 3 mL virus transport media (VTM) with swab) are obtained. This step can further include heat-inactivating the samples in a laboratory convection oven at 65° C. for an hour to inactivate pathogens such as virus in the samples. The heat inactivation step can be substituted or complemented by using DNA/RNA Shield or viral inactivation buffers. Next, samples are accessioned by scanning barcodes on the sample tubes and are placed in racks (e.g., racks of 6 sets of 15 tubes). Barcodes are rescanned to confirm sample tubes are loaded correctly. Samples are then automatically reformatted from sample tubes to 96-well sample blocks using a liquid handler (e.g., OT-2 liquid 96 channel). Next, human and viral nucleic acids are automatically extracted from the samples and dispensed into barcoded 384 well plates. Each step of virus inactivation, sample accessioning, reformatting, and RNA extraction can take about 1 hour. Next, a master mix of primers and/or probes is prepared and a small volume rRT-PCR (e.g., in 10 μL or less reaction volume) is performed with a small amount (e.g., microdroplet such as 0.1 μL or less) of highly concentrated primers and probes to detect target nucleic acids. rRT-PCR results are used for identification of a pathogen, for example, a virus or a bacteria. Positive results are indicative of the presence of a pathogen. In some embodiments, raw data from rRT-PCR results can be converted to visual display to confirm controls worked properly.

Provided herein are methods and compositions of diagnosing a disease or an infection in a high throughput manner using, for example, polymerase chain reaction (PCR), quantitative or real-time PCR (qPCR), reverse transcription-PCR (RT-PCR), and/or quantitative or real-time RT-PCR (rRT-PCR or RT-qPCR), wherein any steps in diagnosis workflow are highly automated using robot-driven working stations. Methods and compositions described herein can utilize specialized sample collection vials that can be used in a substantially- or fully-automated method as disclosed herein. For example, sample collection vials can be small, machine-decappable, machine-recappable, and 1D/2D barcoded. Individual samples collected in collection vials can be reformatted into multiple-well plate format that is suitable for high throughput testing (e.g., rRT-PCR) and analysis. For example, a liquid 96 channel liquid handler as described herein can be used for automatic sample reformatting. Methods and compositions described herein can utilize plates with multiple wells that can be used in a substantially- or fully-automated method as disclosed herein. For example, 96-well, 384-well or 1536-well plates can be used for the methods and compositions described herein. Using an automated process, a master mix of reagents necessary for the nucleic acid extraction or a master mix of reagents for rRT-PCR testing (e.g., reaction mixture or amplification mixture) can be prepared and distributed onto multiple-well plates. In addition, one or more primer and probe sets can be prepared and dispensed automatically. Methods and compositions described herein can utilize instruments described herein or similar instruments suitable for methods and compositions described herein. Sample tracking and uploading results to an electronic health record can be also automated. Instruments for automation described herein are also described in US20200246976 and US20200200779, each of which is incorporated by reference in its entirety.

PCR-Based Diagnostic Tests

Provided herein are methods and compositions for diagnosing a disease or an infection in a high throughput manner using, for example, polymerase chain reaction (PCR), quantitative or real-time PCR (qPCR), reverse transcription-PCR (RT-PCR), and/or real-time RT-PCR (rRT-PCR, RT-qPCR, or qRT-PCR) at robot-driven working stations. PCR is an enzyme-driven process for amplifying short segments of nucleic acid in vitro. This method utilizes partial target nucleic acid sequences to design oligonucleotides (primers) that can hybridize specifically to the target sequences in target nucleic acids. A thermostable polymerase enzyme is used to copy the target sequence in the presence of other necessary components such as nucleotides (e.g., deoxynucleotide triphosphates (dNTPs)) and primers as well as PCR/amplification buffer. The target nucleic acid can be amplified exponentially via multiple amplification cycles including denaturation of target nucleic acid, primer hybridization, and primer extension. This amplification step can be performed in a thermocycler that can run multiple rounds of heating and cooling to provide temperature necessary for each step of the amplification (e.g., denaturation, primer hybridization and extension, etc.). Each step of the cycle can be optimized for different target nucleic acid and primer pair combinations. qPCR is a process where amplification of target nucleic acid and detection of amplified products are coupled in a single reaction vessel. Fluorescent DNA intercalating dyes or fluorescently labeled oligonucleotide probes can be used to visualize the amplified products for real-time monitoring. Examples of fluorescent dyes include, but are not limited to, SYBR-Green I, propidium monoazide (PMA), ethidium monoazide (EMA), SYTOX Orange, SYTO-9, SYTO-13, SYTO-16, SYTO-60, SYTO-62, SYTO-64, SYTO-82, BEBO, YO-PRO-1, LC Green, PO-PRO-3, TO-PRO-3, TOTO-3, POPO-3 and BOBO-3. Examples of oligonucleotide probes include, but are not limited to, TaqMan, fluorescence resonance energy transfer (FRET), molecular beacon probes, scorpion probes, and multiplex probes. The fluorescent signal intensity increases in proportion to the amount of amplified products generated and the amount of starting templates in a sample can be quantified by comparing the exact cycle number at which amplified products accumulate significantly over baseline with a pre-derived quantitative standard. RT-PCR utilizes a reverse transcriptase to generate DNA amplification products from a target RNA by combining the process of reverse transcribing a target RNA into DNA and amplifying specific DNA targets by PCR. RT-PCR can be combined with qPCR to measure the amount of a specific target RNA (rRT-PCR or qRT-PCR).

An amplification reaction mixture described herein can include, for example, a target nucleic acid (or a biological sample containing target nucleic acids such as DNA or RNA), a polymerase, deoxynucleotide triphosphates (dNTPs), reaction or amplification buffer, DNAse/RNAse-free water, and magnesium or manganese. An amplification reaction mixture can further comprise a pair of oligonucleotide primers. In some embodiments, a reaction mixture can comprise two or more pairs of oligonucleotide primers. In some embodiments, a reaction mixture comprises a DNA-dependent DNA polymerase or an RNA-dependent DNA polymerase. In some embodiments, a reaction mixture comprises a DNA-dependent DNA polymerase and an RNA-dependent DNA polymerase. In some embodiments, a reaction mixture comprises a reverse transcriptase. Any DNA polymerase useful for PCR can be used in the methods and compositions disclosed herein. Nonlimiting examples of a DNA-dependent DNA polymerase that can be used in a method disclosed herein include, but are not limited to, a T4 DNA polymerase, a T7 DNA polymerase, a phi29 DNA polymerase, a Bst DNA polymerase, a E. coli DNA polymerase I, a Klenow DNA polymerase, a Taq polymerase, a Pfu DNA polymerase, a Tfl DNA polymerase, and a Tth DNA polymerase. In some embodiments, a polymerase is a thermostable polymerase. In some embodiments, a retroviral reverse transcriptase (RT) can be used for rRT-PCR. Non-limiting examples of retroviral RTs that can be used in a method disclosed herein include, but are not limited to, Avian myeloblastosis virus (AMV) RT and Moloney murine leukemia virus (MMLV or MuLV) RT. In some embodiments, a thermostable DNA polymerase that possesses a reverse transcriptase activity (e.g., a Tfl DNA polymerase or a Tth DNA polymerase), can be used. In some embodiments, a modified version of a DNA polymerase or an RT described herein can be used. For example, an RT with mutations (e.g., point mutations) in RNase H activity domain or deletion of RNase H activity domain can be used to inhibit premature degradation of the RNA strand of an RNA:DNA hybrid.

In some embodiments, a reaction mixture may not comprise a pair of oligonucleotide primers (e.g., pre-mixture). In this embodiment, the pair of oligonucleotide primers can be provided or added separately. For example, a reaction pre-mixture that does not contain primers is prepared first and primers are added to the pre-mixture to form a reaction mixture to amplify a target nucleic acid sequence.

Provided herein are methods and compositions for detecting a target nucleic acid using a method to amplify a target nucleic acid, including polymerase chain reaction (PCR), quantitative or real-time PCR (qPCR), reverse transcription-PCR (RT-PCR), and/or quantitative or real-time RT-PCR (rRT-PCR or RT-qPCR) in a small volume. For example, a reaction mixture or amplification mixture on multiple-well reaction plates can be prepared in a small reaction volume. In some embodiments, a reaction mixture or amplification mixture can have a volume of about 0.1, about 0.2, about 0.3, about 0.4, about 0.5, about 0.6, about 0.7, about 0.8, about 0.9, about 1, about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.5, about 6, about 6.5, about 7, about 7.5, about 8, about 8.5, about 9, about 9.5, about 10, about 10.5, about 11, about 11.5, about 12, about 12.5, about 13, about 13.5, about 14, about 14.5, about 15, about 15.5, about 16, about 16.5, about 17, about 17.5, about 18, about 18.5, about 19, about 19.5, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 µL. In some embodiments, a reaction mixture or amplification mixture can have a volume of about 2.5 µL. In some embodiments, a reaction mixture or amplification mixture can have a volume of about 5 µL. In some embodiments, a reaction mixture or amplification mixture can have a volume of about 10 µL. In some embodiments, a reaction mixture or amplification mixture can have a volume of about 0.1 to about 0.5 µL, about 0.3 to about 0.8 µL, about 0.5 to about 1 µL, about 0.8 to about 1.3 µL, about 1 to about 1.5 µL, about 1.3 to about 1.8 µL, about 1.5 to about 2 µL, about 1.8 to about 2.3 µL, about 2 to about 2.5 µL, about 2.3 to about 2.8 µL, about 2.5 to about 3 µL, about 2.8 to about 3.3 µL, about 3 to about 3.5 µL, about 3.3 to about 3.8 µL, about 3.5 to about 4 µL, about 3.8 to about 4.3 µL, about 4 to about 4.5 µL, about 4.3 to about 4.8 µL, about 4.5 to about 5 µL, about 4.8 to about 5.3 µL, about 5 to about 5.5 µL, about 5.3 to about 5.8 µL, about 5.5 to about 6 µL, about 5.8 to about 6.3 µL, about 6 to about 6.5 µL, about 6.3 to about 6.8 µL, about 6.5 to about 7 µL, about 6.8 to about 7.3 µL, about 7 to about 7.5 µL, about 7.3 to about 7.8 µL, about 7.5 to about 8 µL, about 7.8 to about 8.3 µL, about 8 to about 8.5 µL, about 8.3 to about 8.8 µL, about 8.5 to about 9 µL, about 8.8 to about 9.3 µL, about 9 to about 9.5 µL, about 9.3 to about 9.8 µL, about 9.5 to about 10 µL, about 9.8 to about 10.3 µL, about 10 to about 15 µL, about 13 to about 18 µL, about 15 to about 20 µL, or about 18 to about 23 µL. In some embodiments, reaction mixture has a volume of about 0.5 to about 20 µL. In some embodiments, reaction mixture has a volume of about 0.5 to about 10 µL. In some embodiments, a reaction mixture or amplification mixture can have a volume of about 0.5 to about 1 µL.

Provided herein are methods and compositions of detecting a target nucleic acid in a sample by contacting said sample with at least one microdroplet comprising a pair of primers and amplifying said target nucleic acid. In some embodiments, a microdroplet can contain a volume of from about 1 nL to about 10 µL. In some embodiments, a microdroplet can contain a volume of equal to or less than about 10, about 9, about 8, about 7, about 6, about 5, about 4, about 3, about 2, about 1, about 0.9, about 0.8, about 0.7, about 0.6, about 0.5, about 0.45, about 0.4, about 0.35, about 0.3, about 0.25, about 0.2, about 0.15, about 0.1, about 0.09, about 0.08, about 0.07, about 0.06, about 0.05, about 0.04, about 0.03, about 0.02, or about 0.01 µL. In some embodiments, a microdroplet can contain a volume of equal to or less than about 500, about 450, about 400, about 350, about 300, about 250, about 200, about 190, about 180, about 170, about 160, about 150, about 140, about 130, about 120, about 110, about 100, about 95, about 90, about 85, about 80, about 75, about 70, about 65, about 60, about 55, about 50, about 45, about 40, about 35, about 30, about 25, about 20, about 15, about 10, about 9.5, about 9, about 8.5, about 8, about 7.5, about 7, about 6.5, about 6, about 5.5, about 5, about 4.5, about 4, about 3.5, about 3, about 2.5, about 2, about 1.5, or about 1 nL. In some embodiments, a microdroplet can contain a volume of 150 nL. In some embodiments, a microdroplet can contain a volume of 250 nL. In some embodiments, a microdroplet can contain a volume of 2.5 nL. In some embodiments, a microdroplet can contain a volume of 25 nL.

In some embodiments, a microdroplet can comprise a pair of primers. In some embodiments, a primer or a pair of primers can have a concentration of at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 600, about 700, about 800, about 900, or at least about 1000 nM before being added to an amplification mixture or a reaction mixture. In some embodiments, a primer or a pair of primers can have a concentration of at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 600, about 700, about 800, about 900, or at least about 1000 nM in an amplification mixture or a reaction mixture. In some embodiments, a primer or a pair of primers can have a concentration of at least about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, or at least about 1000 µM before being added to an amplification mixture or a reaction mixture. In some embodiments, a primer or a pair of primers can have a concentration of at least about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, or at least about 1000 µM in an amplification mixture or a reaction mixture.

In some embodiments, a microdroplet can comprise a probe. In some embodiments, a probe can have a concentration of at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 600, about 700, about 800, about 900, or at least about 1000 nM. In some embodiments, a probe can have a concentration of at least about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 60, about 70, about 80, about 90, about 100, about 150, about 200, about 250, about 300, about 350, about 400, about 450, about 500, about 550, about 600, about 650, about 700, about 750, about 800, about 850, about 900, about 950, or at least about 1000 µM.

Further provided herein are methods and compositions for detecting a target nucleic acid in a sample by contacting said sample with two or more microdroplets. In some embodiments, each microdroplet of the two or more microdroplets can comprise a pair of primers. In some embodiments, each microdroplet of the two or more microdroplets can comprise a probe. In some embodiments, methods of detecting a target nucleic acid in a sample as provided herein can comprise contacting the sample with about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 32, about 34, about 36, about 38, about 40, about 42, about 44, about 46, about 48, about 50, about 55, about 60, about 65, about 70, about 75, about 80, about 85, about 90, about 95, or about 100 microdroplets, wherein each microdroplet can comprise a pair of primers and/or a probe. In some embodiments, methods of detecting a target nucleic acid in a sample as provided herein can comprise contacting the sample with 50-100 microdroplets, wherein each of said 50-100 microdroplets can comprise a pair of primers and/or a probe.

Provided herein are methods and compositions of detecting a target nucleic acid in a sample with high accuracy. In some embodiments, amplification can have at least about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or about 100% accuracy. Also provided herein are methods and compositions of detecting a target nucleic acid in a sample with high sensitivity. In some embodiments, amplification has at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or at least about 99% sensitivity relative to a positive control amplification. For example, amplification has at least 95% sensitivity relative to a positive control amplification. In some embodiments, amplification has at least about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or at least about 99% sensitivity relative to a negative control amplification. For example, amplification has at least 95% sensitivity relative to a negative control amplification.

Provided herein are methods and compositions for amplifying a target nucleic acid in a sample with a limit of detection (LoD). The term "limit of detection" or "LoD" as used herein can refer to the lowest quantity or concentration of a component or an analyte, for example, amplification or amplification product, that can be distinguished from the absence of that component or analyte and can be measured or detected with statistical significance. For example, LoD can be defined as the lowest concentration of a target nucleic acid (e.g., DNA or RNA) detected at least 95% of the times among the replicates of that specific concentration.

LoD may be measured and determined using serially diluted controls, for example, positive controls or negative control samples "spiked" with a target nucleic acid sequence of interest, e.g., inactivated viral particles. For example, LoD may be determined by amplifying a target nucleic acid sequence in a plurality of serially diluted positive controls. In some embodiments, the test to determine LoD uses positive control sample serially diluted, with each concentration of the series containing from 0.01, 0.05, 0.1, 0.2, 0.3, 0.4, 0.5, 1, 2, 3, 5, 10, 20, 30, 40, 50, 60, 70, 80, 90, 100, 150, 200, 250, 300, 350, 400, 500 or more copies of the target nucleic acid. An exemplary dilution series may be 0.01, 0.1, 1, 10, 100, 1000 copies of a target nucleic acid sequence in positive controls. An exemplary dilution series may be 0.02, 0.03, 0.04, 0.06, 0.08, 0.13, 0.17, 0.25, 0.5, 0.7, 1, 1.3, 2.0, 2.7, 4.9, 5.3, 8.0, 10.7, 16, 21.3, and 32 copies of a target nucleic acid sequence in positive controls. In some embodiments, LoD is determined by amplification with a plurality of positive control samples at each concentration of the serial dilution, thereby allowing determination of threshold probability for detection of amplification. For example, LoD may be determined as the lowest concentration that allows for detectable amplification in a certain percentage of positive controls at the concentration, e.g., 80%, 85%, 90%, 95%, 99%, 99.9%, or more. The level of detectable amplification by thermal cycling is understood by those skilled in the art, for example, as measured by fluorescent signal or probe quenching signal as used in qRT-PCR.

In some embodiments, LoD is measured and determined for biological samples, or control samples resembling components and formation of biological samples. For example, LoD may be determined by amplifying serially diluted samples each comprising a certain concentration of a biological form harboring a target nucleic acid sequence, e.g., viral particles harboring the target nucleic acid sequence. Such viral particles may be inactivated viral particles. The serially diluted samples comprising the biological form, e.g. inactivated viral particles, may be serially diluted in dilution mixes or solutions that resemble biological samples, for example, inactivated viral particles may be serially diluted in a negative sample matrix that have pooled negative biological specimens (e.g. negative nasal swabs) in viral transport media. In some embodiments, such samples are subsequently carried through a nucleic acid isolation procedure to purify the viral genomic material, with the LoD defined as the lowest concentration of spiked virus detected in in a given percentage of samples of the concentration, for example, 80%, 85%, 90%, 95%, 99%, 99.9% or more of samples. In some embodiments, LoD is determined by the lowest concentration of said target nucleic acid above detection threshold in at least 95% of reactions among the replicates of said lowest concentration. In some embodiments, LoD is determined by the lowest concentration above detection threshold in at least 95% of reactions when tested with serial dilution of positive controls. In some embodiments, LoD is determined by the lowest concentration above detection threshold in at least 95% of reactions when tested with serial dilution of positive controls, wherein said serial dilution comprises inactivated viral particles.

In some embodiments, amplification has a limit of detection (LoD) of about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 500, about 1000, about 1200, about 1400, about 1600, about 1800, about 2000, about 2200, about 2400, about 2600, about 2800, about 3000, about 3200, about 3400, about 3600, about 3800, about 4000, about 4200, about 4400, about 4600, about 4800, or about 5000 molecules or copies per mL as determined by amplification with standard positive controls. In some embodiments, amplification has a limit of detection (LoD) of 10-200 molecules or copies per mL, wherein said LoD is determined by the lowest concentration above detection threshold in at least 95% of reactions when tested with serial dilution of positive controls. In some embodiments, amplification has a limit of detection (LoD) of 1000 molecules or copies per mL, wherein said LoD is determined by the lowest concentration above detection threshold in at least 95% of reactions when tested with serial dilution of positive controls. In some embodiments, amplification has a limit of detection (LoD) of 50 molecules or copies per mL, wherein said LoD is determined by the lowest concentration above detection threshold in at least 95% of reactions when tested with serial dilution of positive controls. In some embodiments, amplification has a limit of detection (LoD) of 100 molecules or copies per mL, wherein said LoD is determined by the lowest concentration above detection threshold in at least 95% of reactions when tested with serial dilution of positive controls. In some embodiments, amplification has a limit of detection (LoD) of 3000 molecules or copies per mL, wherein said LoD is determined by the lowest concentration of said target nucleic acid above detection threshold in at least 95% of reactions among the replicates of said lowest concentration. In some embodiments, amplification has a limit of detection (LoD) of 200 molecules or copies per mL. wherein said LoD is determined by the lowest concentration above detection threshold in at least 95% of reactions when tested with serial dilution of positive controls, wherein said serial dilution comprises inactivated viral particles.

In some embodiments, detection has a limit of detection (LoD) of about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 500, about 1000, about 1200, about 1400, about 1600, about 1800, about 2000, about 2200, about 2400, about 2600, about 2800, about 3000, about 3200, about 3400, about 3600, about 3800, about 4000, about 4200, about 4400, about 4600, about 4800, or about 5000 molecules or copies per mL as determined by amplification with standard positive controls. In some embodiments, detection has a limit of detection (LoD) of 100-2000 molecules or copies per mL as determined by detection with standard positive controls. In some embodiments, detection has a limit of detection (LoD) of 100 molecules or copies per mL as determined by detection with standard positive controls. In some embodiments, detection has a limit of detection (LoD) of 500 molecules or copies per mL as determined by detection with standard positive controls. In some embodiments, detection has a limit of detection (LoD) of 1000 molecules or copies per mL as determined by detection with standard positive controls. In some embodiments, detection has a limit of detection (LoD) of 2000 molecules or copies per mL as determined by detection with standard positive controls.

In some embodiments, amplification has a polymerase chain reaction (PCR) limit of detection (LoD) of from about 0.01 to about 35 molecules or copies of target nucleic acid/µL. In some embodiments, amplification has a PCR LoD of about 0.01, about 0.02, about 0.03, about 0.04, about 0.05, about 0.06, about 0.07, about 0.08, about 0.09, about 0.1, about 0.11, about 0.12, about 0.13, about 0.14, about 0.15, about 0.16, about 0.17, about 0.18, about 0.19 about 0.2, about 0.21, about 0.22, about 0.23, about 0.24, about 0.25, about 0.26, about 0.27, about 0.28, about 0.29, about 0.3, about 0.35, about 0.4, about 0.45, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, about 12.0, about 12.1, about 12.2, about 12.3, about 12.4, about 12.5, about 12.6, about 12.7, about 12.8, about 12.9, about 13.0, about 13.1, about 13.2, about 13.3, about 13.4, about 13.5, about 13.6, about 13.7, about 13.8, about 13.9, about 14.0, about 14.1, about 14.2, about 14.3, about 14.4, about 14.5, about 14.6, about 14.7, about 14.8, about 14.9, about 15.0, about 15.1, about 15.2, about 15.3, about 15.4, about 15.5, about 15.6, about 15.7, about 15.8, about 15.9, about 16.0, about 16.1, about 16.2, about 16.3, about 16.4, about 16.5, about 16.6, about 16.7, about 16.8, about 16.9, about 17.0, about 17.1, about 17.2, about 17.3, about 17.4, about 17.5, about 17.6, about 17.7, about 17.8, about 17.9, about 18.0, about 18.1, about 18.2, about 18.3, about 18.4, about 18.5, about 18.6, about 18.7, about 18.8, about 18.9, about 19.0, about 19.1, about 19.2, about 19.3, about 19.4, about 19.5, about 19.6, about 19.7, about 19.8, about 19.9, about 20.0, about 20.1, about 20.2, about 20.3, about 20.4, about 20.5, about 20.6, about 20.7, about 20.8, about 20.9, about 21.0, about 21.1, about 21.2, about 21.3, about 21.4, about 21.5, about 21.6, about 21.7, about 21.8, about 21.9, about 22.0, about 22.1, about 22.2, about 22.3, about 22.4, about 22.5, about 22.6, about 22.7, about 22.8, about 22.9, about 23.0, about 23.1, about 23.2, about 23.3, about 23.4, about 23.5, about 23.6, about 23.7, about 23.8, about 23.9, about 24.0, about 24.1, about 24.2, about 24.3, about 24.4, about 24.5, about 24.6, about 24.7, about 24.8, about 24.9, about 25.0, about 25.3, about 25.5, about 25.8, about 26.0, about 26.3, about 26.5, about 26.8, about 27.0, about 27.3, about 27.5, about 27.8, about 28.0, about 28.3, about 28.5, about 28.8, about 29.0, about 29.3, about 29.5, about 29.8, about 30.0, about 30.3, about 30.5, about 30.8, about 31.0, about 31.3, about 31.5, about 31.8, about 32.0, about 32.3, about 32.5, about 32.8, about 33.0, about 33.3, about 33.5, about 33.8, about 34.0, about 34.3, about 34.5, about 34.8, or about 35.0 molecules or copies of target nucleic acid/µL (e.g., RNA/µL or DNA/µL).

In some embodiments, amplification can produce an average rRT-PCR/RT-qPCR cycle threshold (Ct) value of about 20 to about 50. In some embodiments, amplification can produce an average Ct value of about 20, about 21, about 22, about 23, about 24, about 25, about 26, about 27, about 28, about 29, about 30, about 30, about 30.1, about 30.2, about 30.3, about 30.4, about 30.5, about 30.6, about 30.7, about 30.8, about 30.9, about 31, about 31.1, about 31.2, about 31.3, about 31.4, about 31.5, about 31.6, about 31.7, about 31.8, about 31.9, about 32, about 32.1, about 32.2, about 32.3, about 32.4, about 32.5, about 32.6, about 32.7, about 32.8, about 32.9, about 33, about 33.1, about 33.2, about 33.3, about 33.4, about 33.5, about 33.6, about 33.7, about 33.8, about 33.9, about 34, about 34.1, about 34.2, about 34.3, about 34.4, about 34.5, about 34.6, about 34.7, about 34.8, about 34.9, about 35, about 35.1, about 35.2, about 35.3, about 35.4, about 35.5, about 35.6, about 35.7, about 35.8, about 35.9, about 36, about 36.1, about 36.2, about 36.3, about 36.4, about 36.5, about 36.6, about 36.7, about 36.8, about 36.9, about 37, about 37.1, about 37.2, about 37.3, about 37.4, about 37.5, about 37.6, about 37.7, about 37.8, about 37.9, about 38, about 38.1, about 38.2, about 38.3, about 38.4, about 38.5, about 38.6, about 38.7, about 38.8, about 38.9, about 39, about 39.1, about 39.2, about 39.3, about 39.4, about 39.5, about 39.6, about 39.7, about 39.8, about 39.9, about 40, about 41, about 42, about 43, about 44, about 45, about 46, about 47, about 48, about 49, or about 50. In some embodiments, amplification can produce an average Ct value of 35. In some embodiments, amplification can produce an average Ct value of about 36. In some embodiments, amplification can produce an average Ct value of about 36.7. In some embodiments, amplification can produce an average Ct value of about 37. In some embodiments, amplification can produce an average Ct value of about 37.2. In some embodiments, amplification can produce an average Ct value of at most about 50, about 45, about 40, about 35, or about 30. In some embodiments, amplification can produce an average Ct value of at most about 40.

Provided herein are methods and compositions for amplifying a target nucleic acid in a sample containing the target nucleic acid and non-target nucleic acids. In some embodiments, the amount of the total nucleic acids (e.g., including the target and non-target nucleic acids for example, DNA or RNA) can be at least about 1 ng to at least about 1000 ng. In some embodiments, the amount of the total nucleic acids can be at least about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 550, about 600, about 650, about 700, about 750, about 800, about 850, about 900, about 950, or at least about 1000 ng.

In some embodiments, the amount of the target nucleic acid in the sample can be at least about 0.1 pg to at least about 100 ng. In some embodiments, the amount of the target nucleic acid in the sample can be at least about 0.1, about 0.2, about 0.3, about 0.4, about 0.5, about 0.6 about 0.7, about 0.8, about 0.9, about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 550, about 600, about 650, about 700, about 750, about 800, about 850, about 900, about 950, or at least about 1000 pg. In some embodiments, the amount of the target nucleic acid in the sample can be at least about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, or at least about 100 ng.

Provided herein are methods and compositions for diagnosing a disease or an infection in a high throughput manner by detecting and/or amplifying a target nucleic acid in a plurality of samples using polymerase chain reaction (PCR), quantitative or real-time PCR (qPCR), reverse transcription-PCR (RT-PCR), and/or quantitative or real-time RT-PCR (rRT-PCR or RT-qPCR) at robot-driven working stations. For example, plurality of samples can comprise at least about 2, about 5, about 10, about 15, about 20, about 25, about 30, about 35, about 40, about 45, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 189, about 190, about 191, about 192, about 193, about 194, about 195, about 196, about 197, about 198, about 199, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about 730, about 740, about 750, about 760, about 770, about 780, about 790, about 800, about 810, about 820, about 830, about 840, about 850, about 860, about 870, about 880, about 890, about 900, about 910, about 920, about 930, about 940, about 950, about 960, about 970, about 980, about 990, about 1000, about 1050, about 1100, about 1110, about 1120, about 1130, about 1140, about 1150, about 1160, about 1170, about 1180, about 1190, about 1200, about 1210, about 1220, about 1230, about 1240, about 1250, about 1260, about 1270, about 1280, about 1290, about 1300, about 1310, about 1320, about 1330, about 1340, about 1350, about 1360, about 1370, about 1380, about 1390, about 1400, about 1410, about 1420, about 1430, about 1440, about 1450, about 1460, about 1470, about 1480, about 1490, about 1500, about 1510, about 1520, about 1530, about 1540, about 1550, about 1560, about 1570, about 1580, about 1590, about 1600, about 1610, about 1620, about 1630, about 1640, about 1650, about 1660, about 1670, about 1680, about 1690, about 1700, about 1710, about 1720, about 1730, about 1740, about 1750, about 1760, about 1770, about 1780, about 1790, about 1800, about 1810, about 1820, about 1830, about 1840, about 1850, about 1860, about 1870, about 1880, about 1890, about 1900, about 1910, about 1920, about 1930, about 1940, about 1950, about 1960, about 1970, about 1980, about 1990, about 2000, about 2010, about 2020, about 2030, about 2040, about 2050, about 2060, about 2070, about 2080, about 2090, about 2100, about 2110, about 2120, about 2130, about 2140, about 2150, about 2160, about 2170, about 2180, about 2190, about 2200, about 2210, about 2220, about 2230, about 2240, about 2250, about 2260, about 2270, about 2280, about 2290, about 2300, about 2310, about 2320, about 2330, about 2340, about 2350, about 2360, about 2370, about 2380, about 2390, about 2400, about 2410, about 2420, about 2430, about 2440, about 2450, about 2460, about 2470, about 2480, about 2490, about 2500, about 2510, about 2520, about 2530, about 2540, about 2550, about 2560, about 2570, about 2580, about 2590, about 2600, about 2610, about 2620, about 2630, about 2640, about 2650, about 2660, about 2670, about 2680, about 2690, about 2700, about 2710, about 2720, about 2730, about 2740, about 2750, about 2760, about 2770, about 2780, about 2790, about 2800, about 2810, about 2820, about 2830, about 2840, about 2850, about 2860, about 2870, about 2880, about 2890, about 2900, about 2910, about 2920, about 2930, about 2940, about 2950, about 2960, about 2970, about 2980, about 2990, or at least about 3000 samples. In some embodiments, said plurality of samples comprises 96-2000 samples. In some embodiments, said plurality of samples comprises at least 384 samples. In some embodiments, said plurality of samples comprises at least 1536 samples.

Further provided herein, in some embodiments, are methods and compositions for detecting and/or amplifying a target nucleic acid sequence in a plurality of samples at a high rate with a single device. For example, methods and compositions described herein allow detecting and/or amplifying a target nucleic acid sequence at a rate of at least about 500, about 1000, about 1500, about 2000, about 2500, about 3000, about 3500, about 4000, about 4500, about 5000, about 5500, about 6000, about 6500, about 7000, about 7500, about 8000, about 8500, about 9000, about 9500, about 10000, about 10500, about 11000, about 11500, about 12000, about 12500, about 13000, about 13500, about 14000, about 14500, about 15000, about 15500, about 16000, about 16500, about 17000, about 17500, about 18000, about 18500, about 19000, about 19500, or at least about 20000 samples per day with a single device. For example, methods and compositions described herein allow detecting and/or amplifying a target nucleic acid sequence at a rate of from about 500 to about 2500, from about 1000 to about 3000, from about 1500 to about 3500, from about 2000 to about 4000, from about 2500 to about 4500, from about 3000 to about 5000, from about 3500 to about 5500, from about 4000 to about 6000, from about 4500 to about 6500, from about 5000 to about 7000, from about 5500 to about 7500, from about 6000 to about 8000, from about 6500 to about 8500, from about 7000 to about 9000, from about 8500 to about 10500, from about 9000 to about 11000, from about 9500, from about 10000 to about 12000, from about 11000 to about 13000, from about 12000 to about 14000, from about 13000 to about 15000, from about 14000 to about 16000, from about 15000 to about 17000, from about 16000 to about 18000, from about 17000 to about 19000, from about 18000 to about 20000, from about 19000 to about 21000, from about 20000 to about 22000, from about 21000 to about 23000, from about 22000 to about 24000, from about 23000 to about 25000, from about 24000 to about 26000, from about 25000 to about 27000, from about 26000 to about 28000, from about 27000 to about 29000, or at a rate of from about 28000 to about 30000 samples per day with a single device. In some embodiments, detection has a rate of at least 10000 samples per day. In some embodiments, detection has a rate of at least 15000 samples per day.

Provided herein are methods and compositions for diagnosing a disease or an infection in a high throughput manner by detecting and/or amplifying a target nucleic acid in a plurality of samples using polymerase chain reaction (PCR), quantitative or real-time PCR (qPCR), reverse transcription-PCR (RT-PCR), and/or quantitative or real-time RT-PCR (rRT-PCR or RT-qPCR) at robot-driven working stations, wherein detection and/or amplification occurs on a reaction plate or an automation plate. In some embodiments, the reaction plate or the automation plate comprises multiple wells. For example, 96-well, 384-well or 1536-well plates can be used for methods and compositions described herein. In some embodiments, each of the multiple wells comprises one of the plurality of samples. In some embodiments, each of the plurality of samples are positioned on the reaction plate or the automation plate in a pre-determined manner. In some embodiments, positioning each of the plurality of samples on the reaction plate or the automation plate in a pre-determined manner is performed using an automated liquid handler.

Provided herein are methods and compositions for diagnosing a disease or an infection in a high throughput and accurate manner by detecting and/or amplifying a target nucleic acid in a sample or a plurality of samples using polymerase chain reaction (PCR), quantitative or real-time PCR (qPCR), reverse transcription-PCR (RT-PCR), and/or quantitative or real-time RT-PCR (rRT-PCR or RT-qPCR) at robot-driven working stations, wherein the target nucleic acid sequence is amplified by at least 5 fold after 2-40 amplification cycles in the sample or in the plurality of samples. For example, the target nucleic acid sequence is amplified by at least 2-30 fold after 2-40 amplification cycles. In some embodiments, the target nucleic acid sequence is amplified by at least about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 fold after 2-40 amplification cycles. In some embodiments, the target nucleic acid sequence is amplified by at least 5 fold after 2-40 amplification cycles. In some embodiments, the target nucleic acid sequence is amplified by at least 2-30 fold after 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amplification cycles.

Provided herein are methods and compositions for amplifying a target nucleic acid in a sample by preparing a reaction pre-mixture that does not comprise a primer and contacting the sample with the reaction pre-mixture prior to addition of the primer. In some embodiments, methods and compositions further comprise contacting the reaction pre-mixture with a pair of primers or a microdroplet comprising a pair of primers described herein to form a reaction mixture and amplifying the target nucleic acid sequence in the reaction mixture. In some embodiments, the target nucleic acid sequence is amplified in the reaction mixture within about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, or about 500 milliseconds after contacting the reaction pre-mixture with a pair of primers to form a reaction mixture. In some embodiments, the target nucleic acid sequence is amplified in the reaction mixture within 50 milliseconds after contacting the reaction pre-mixture with a pair of primers or a microdroplet comprising a pair of primers to form a reaction mixture. In some embodiments, the target nucleic acid sequence is amplified in the reaction mixture within about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, or about 500 seconds after contacting the reaction pre-mixture with a pair of primers or a microdroplet comprising a pair of primers to form a reaction mixture. In some embodiments, the amplification is within 30 seconds after contacting the reaction pre-mixture with a pair of primers or a microdroplet comprising a pair of primers to form a reaction mixture. In some embodiments, the target nucleic acid sequence is amplified in the reaction mixture about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, or about 500 milliseconds after contacting the reaction pre-mixture with a pair of primers to form a reaction mixture. In some embodiments, the target nucleic acid sequence is amplified in the reaction mixture 50 milliseconds after contacting the reaction pre-mixture with a pair of primers or a microdroplet comprising a pair of primers to form a reaction mixture. In some embodiments, the target nucleic acid sequence is amplified in the reaction mixture about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, or about 500 seconds after contacting the reaction pre-mixture with a pair of primers or a microdroplet comprising a pair of primers to form a reaction mixture. In some embodiments, the amplification is commenced 30 seconds after contacting the reaction pre-mixture with a pair of primers or a microdroplet comprising a pair of primers to form a reaction mixture.

In some embodiments, the amplification can have a lower limit of detection (LoD) as compared to an amplification by thermal cycling in a reaction mixture comprising a sample, a polymerase, and a pair of primers that are pre-mixed prior to amplification. In some embodiments, the amplification can have at least about 1.1, about 1.2, about 1.3, about 1.4, about 1.5, about 1.6, about 1.7, about 1.8, about 1.9, about 2, about 2.1, about 2.2, about 2.3, about 2.4, about 2.5, about 2.6, about 2.7, about 2.8, about 2.9, about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.5, about 7, about 7.5, about 8, about 8.5, about 9, about 9.5, about 10, about 11, about 12, about 13, about 14, about 15, about 16, about 17, about 18, about 19, about 20, about 25, about 30, about 40, or at least about 50 fold lower LOD compared to an amplification by thermal cycling in a reaction mixture comprising a sample, a polymerase, and a pair of primers that are pre-mixed prior to amplification. In some embodiments, the amplification can have a higher accuracy as compared to an amplification by thermal cycling in a reaction mixture comprising a sample, a polymerase, and a pair of primers that are pre-mixed prior to amplification. In some embodiments, the amplification can have at least about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% higher accuracy as compared to an amplification by thermal cycling in a reaction mixture comprising a sample, a polymerase, and a pair of primers that are pre-mixed prior to amplification.

Further provided herein are methods and compositions for simultaneously diagnosing two or more diseases or infections in a high throughput manner in a single device using a method to amplify a target nucleic acid, including polymerase chain reaction (PCR), quantitative PCR (qPCR), reverse transcription-PCR (RT-PCR), and/or real-time RT-PCR (rRT-PCR) at robot-driven working stations. The methods and compositions comprise simultaneously detecting two or more target nucleic acid sequences in a single device comprising a plurality of samples. For example, automated multiplex rRT-PCR reactions can be set up with multiple pairs of primers, each of which hybridizes with a different target nucleic acid sequence. In some embodiments, the single device comprises multiple wells comprising a plurality of samples. In one embodiment, each well can comprise a different sample from another well in a multi-well plate. In this embodiment, each well comprising a different sample is contacted with two or more pairs of primers or a microdroplet comprising two or more pairs of primers. For example, two or more target sequences can be amplified in one well containing one sample in a single device by contacting the well with two or more pairs of primers. In some embodiments, each pair of the two or more pairs of primers can hybridize with one of the two or more target nucleic acid sequences. In another embodiment, the two or more wells can comprise the same sample. In this embodiment, each well comprising a sample is contacted with one of the two or more pairs of primers. In this embodiment, each of the two or more wells comprising the same sample is contacted with one pair of the two or more pairs of primers or a microdroplet comprising one pair of the two or more pairs of primers. For example, two or more target sequences can be amplified in multiple wells containing the same sample in a single device, wherein each well of multiple wells comprises one pair of the two or more pairs of primers. In some embodiments, each pair of the two or more pairs of primers can hybridize with one of the two or more target nucleic acid sequences.

In some embodiments, the plurality of samples is contacted with two or more pairs of primers or a microdroplet comprising two or more pairs of primers. In this embodiment, each of the two or more pairs of primers can hybridize with one of two or more target nucleic acid sequences to amplify one of the two or more target nucleic acid sequences to a threshold level for detecting. In one embodiment, at least one of the plurality of samples is contacted with the two or more pairs of primers. In another embodiment, at least one of the plurality of samples is contacted with only one pair of the two or more pairs of primers. In some embodiments, each of the plurality of samples is contacted with the two or more pairs of primers. In some embodiments, each of the plurality of samples is contacted with only one pair of the two or more pairs of primers. In some embodiments, each of the two or more target nucleic acid sequences hybridizes with only one pair of the two or more primers. In some embodiments, the two or more target nucleic acids or target nucleic acid sequences can comprise 2, 3, 4, 5, 6, 7, 8, 9, 10 or more target nucleic acids or target nucleic acid sequences. In some embodiments, the two or more pairs of primers can comprise 2, 3, 4, 5, 6, 7, 8, 9, 10 or more pairs of primers.

Provided herein are methods and compositions for diagnosing a disease or an infection in a high throughput manner by amplifying and/or detecting a target nucleic acid in a plurality of samples using, for example, polymerase chain reaction (PCR), quantitative or real-time PCR (qPCR), reverse transcription-PCR (RT-PCR), and/or quantitative or real-time RT-PCR (rRT-PCR or RT-qPCR) at robot-driven working stations. Target nucleic acids or target nucleic acid sequences as described herein can be DNA or RNA. In some embodiments, target nucleic acids or target nucleic acid sequences can be DNA. In one example, target nucleic acids or target nucleic acid sequences can be any viral DNA. Nonlimiting examples of viral DNA include DNA from hepatitis B, adenovirus, papillomavirus, poxvirus, and herpesvirus including herpes simplex virus, varicella zoster virus, Epstein-Barr virus, and cytomegalovirus.

In another example, target nucleic acids or target nucleic acid sequences can be DNA from a bacterium, a fungus, or a parasite. Nonlimiting examples of bacterial DNA comprises DNA from *Streptococcus pyogenes*, coliform, *Escherichia coli*, *Salmonella*, *Shigella*, *Staphylococcus aureus*, *Gardnerella vaginalis*, *Neisseria gonorrhoeae*, *Chlamydia trachomatis*, *Treponema pallidum*, *Clostridium difficile*, *Mycobacterium tuberculosis*, *Bordetella pertussis*, *Streptococcus pneumoniae*, *Mycoplasma pneumoniae*, *Haemophilus influenzae*, *Legionella pneumophila*, *Neisseria meningitidis*, *Listeria monocytogenes*, *Borrelia burgdorferi*, *Vibrio cholerae*, *Clostridium botulinum*, *Clostridium tetani*, *Clostridium perfringens*, *Campylobacter*, *Vibrio parahaemolyticus*, *Bacillus cereus*, or *Bacillus anthracis*. Nonlimiting examples of fungal DNA comprises DNA from *Candida albicans*, *Trichophyton*, *Microsporum*, *Epidermophyton*, *Trichophyton rubrum*, *Epidermophyton floccosum*, *Aspergillus*, *Histoplasma capsulatum*, *Cryptococcus neoformans*, *Cryptococcus gattii*, *Coccidioides* or *Blastomyces*. Nonlimiting examples of a parasite comprises a protozoan, a helminth, or an ectoparasite.

Protozoa are microscopic, one-celled organisms that can be free-living or parasitic in nature. The protozoa that are infectious to humans can be classified into four groups based on their mode of movement and the four groups include Sarcodina (ameba, e.g., *Entamoeba*), Mastigophora (*flagellates*, e.g., Giardia, *Leishmania*), Ciliophora (ciliates, e.g., *Balantidium*), and Sporozoa (e.g., *Plasmodium*, *Cryptosporidium*). In some embodiments, Plasmodia comprises *Plasmodium falciparum*, *Plasmodium vivax*, *Plasmodium malariae*, or *Plasmodium ovale*. Helminths are large, multicellular organisms that can be either free-living or parasitic in nature. Nonlimiting examples of helminths can include, but are not limited to, flatworms (also called as platyhelminths, e.g., trematodes and cestodes), thorny-headed worms (e.g., acanthocephalins), and roundworms (also called as nematodes). Nonlimiting examples of ectoparasites can include blood-sucking arthropods such as mosquitoes, ticks, fleas, lice, and mites that attach or burrow into the skin and remain there for relatively long periods of time (e.g., weeks to months).

In some embodiments, target nucleic acids or target nucleic acid sequences can be RNA. For example, target nucleic acids or target nucleic acid sequences can be any viral RNA. Nonlimiting examples of viral RNA include RNA from severe acute respiratory syndrome coronavirus 2 (SARS-CoV-2), human immunodeficiency virus (HIV), Human T-cell lymphotropic virus type 1 (HTLV-1), influenza virus (influenza virus A, influenza virus B, and/or influenza virus C), Dengue virus, hepatitis C virus, hepatitis E virus, ebolavirus, lyssavirus, poliovirus, West Nile virus, respiratory syncytial virus (RSV), parainfluenza virus (NV), human metapneumovirus (hMPV), human rhinovirus (HRV), severe acute respiratory syndrome coronavirus 1 (SARS-CoV-1), middle east respiratory syndrome coronavirus (MERS-CoV), and measles virus.

Further provided herein, in some aspects, are methods and compositions for simultaneously amplifying and/or detecting two or more target nucleic acids in a plurality of samples. In this aspect, the two or more target nucleic acids or target nucleic acid sequences can be DNA or RNA. In one example, each of the two or more target nucleic acids or target nucleic acid sequences can be DNA. In another example, each of the two or more target nucleic acids or target nucleic acid sequences can be RNA. In some embodiments, the two or more target nucleic acids or target nucleic acid sequences can comprise DNA and RNA. For example, one of the two or more target nucleic acids can be DNA and another of the two or more target nucleic acids can be RNA. In some embodiments, the two or more target nucleic acids or target nucleic acid sequences can be any viral DNA described herein and/or viral RNA described herein. In some embodiments, the two or more target nucleic acids or target nucleic acid sequences can be any DNA from a bacterium, a fungus, or a parasite described herein. For example, one of the two or more target nucleic acids can be RNA from SARS-CoV-2 and another of the two or more target nucleic acids can be RNA from HIV. For example, one of the two or more target nucleic acids can be RNA from SARS-CoV-2, another of the two or more target nucleic acids can be RNA from HIV, and yet another of the two or more target nucleic acids can be RNA from influenza virus. For example, one of the two or more target nucleic acids can be RNA from SARS-CoV-2 and another of the two of more target nucleic acids can be DNA from hepatitis B. For example, one of the two or more target nucleic acids can be RNA from SARS-CoV-2, another of the two of more target nucleic acids can be DNA from hepatitis B, and yet another of the two or more target nucleic acids can be DNA from *Streptococcus pyogenes*.

Biological Samples

Provided herein are methods and compositions for diagnosing a disease or an infection in a high throughput manner using a method to amplify a target nucleic acid, including, for example, polymerase chain reaction (PCR), quantitative or real-time PCR (qPCR), reverse transcription-PCR (RT-PCR), and/or quantitative or real-time RT-PCR (rRT-PCR or RT-qPCR) to amplify target nucleic acid from a sample. A sample can be derived from a biological sample, i.e., extracted from a biological sample. A biological sample can be from a virus, bacterium, mycoplasma, parasite, fungus, or plant. A biological sample can be from an animal, such as a mammal, for example, a human, non-human primate, rodent, caprine, bovine, ovine, equine, canine, feline, mouse, rat, rabbit, horse or goat. In some embodiments, a biological sample is obtained from a human subject. The human subject can be a patient. The human subject can be an adult, an adolescent, a pre-adolescent, a child, a toddler, an infant, or a neonate. A biological sample can be a tissue sample or bodily fluid, such as a human bodily fluid. For example, the bodily fluid can be blood, sera, plasma, lavage, urine, cerebrospinal fluid (CSF), sputum, saliva, bone marrow, synovial fluid, aqueous humor, amniotic fluid, cerumen, breast milk, bronchoalveolar lavage fluid, semen, prostatic fluid, Cowper's fluid, pre-ejaculatory fluid, female ejaculate, sweat, tears, cyst fluid, pleural fluid, peritoneal fluid, pericardial fluid, lymph, chyme, chyle, bile, interstitial fluid, menses, pus, sebum, vaginal secretion, mucosal secretion, stool water, pancreatic juice, lavage fluid from sinus cavities, bronchopulmonary aspirate, blastocoel cavity fluid, or umbilical cord blood. A biological sample can comprise a cell, such as a stem cell, undifferentiated cell, differentiated cell, or a cell from a diseased subject or a subject suspected of having a condition or infection. A biological sample can be blood, a cell, a population of cells, a quantity of tissue, or fluid of a subject. In some embodiments, a biological sample comprises nasopharyngeal fluid, oropharyngeal fluid, saliva, blood, sera, plasma, lavage, urine, ear exudate, cerebrospinal fluid (CSF), sputum, saliva, bone marrow, synovial fluid, aqueous humor, amniotic fluid, cerumen, breast milk, auroral pharyngeal lavage fluid, bronchoalveolar lavage, bronchoalveolar lavage fluid, semen, prostatic fluid, Cowper's fluid, pre-ejaculatory fluid, female ejaculate, sweat, tears, cyst fluid, pleural fluid, peritoneal fluid, pericardial fluid, lymph, chyme, chyle, bile, interstitial fluid, menses, pus, sebum, vaginal secretion, mucosal secretion, stool, stool water, pancreatic juice, lavage fluid from sinus cavities, bronchopulmonary aspirate, blastocoel cavity fluid, or umbilical cord blood.

A biological sample can be collected by any non-invasive means, such as, for example, by a nasopharyngeal swab, a nasal swab, an oropharyngeal swab, or a buccal swab. A biological sample can be also collected by drawing, for example, blood or any other bodily fluid from a subject, or using fine needle aspiration or needle biopsy. A biological sample can be collected by the subject providing the sample to, for example, a doctor or lab technician. For example, the subject can provide a urine, stool, or saliva sample.

In one aspect, methods described herein can be performed with the biological sample itself without or with limited processing of the sample. In another aspects, method described herein can be performed on nucleic acid molecules extracted from a biological sample. For example, DNA or RNA can be extracted from samples before analysis. Most methods of RNA isolation from swabs, bodily fluids, or tissues can be based on the disruption of the tissue in the presence of protein denaturants to quickly and effectively inactivate RNAses. Isolated total RNA can then be further purified from the protein contaminants and concentrated by selective ethanol precipitations, phenol/chloroform extractions followed by isopropanol precipitation or cesium chloride, lithium chloride or cesium trifluoroacetate gradient centrifugations.

After extraction, RNA can be amplified, and transcribed into cDNA, which can then serve as template for multiple rounds of amplification by the appropriate DNA polymerase. Reverse transcription reactions can be carried out using non-specific primers, such as an anchored oligo-dT primer, or random sequence primers, or using a target-specific primer complementary to target RNA sequence for each probe being monitored, or using thermostable RNA-dependent DNA polymerases (such as a AMV RT or a MMLV RT).

A biological sample can be subject to a chemical treatment or a heat treatment. For example, a biological sample can be treated with N-acetylcysteine (NAC) to help liquify mucus that is common in some of samples such as saliva samples. In some embodiments, a biological sample is treated with N-acetylcysteine (NAC) before a sample is extracted from the biological sample. In some embodiments, a biological sample is treated to inactivate infectious agents or a pathogen (e.g., viral, bacterial, fungal, or parasitic) before a sample is extracted. In some embodiments, a biological sample is heat-inactivated before a sample is extracted. In some embodiments, heat activation is performed in a convection oven at 65° C. In some embodiments, a biological sample is inactivated in virus-inactivating buffers. In some embodiments, a biological sample is inactivated using DNA/RNA Shield.

Computer Systems

Any of the systems described herein, can be operably linked to a computer and can be automated through a computer either locally or remotely. In various instances, the methods and systems of the invention can further comprise software programs on computer systems and uses thereof. Accordingly, computerized control for the synchronization of the dispense/vacuum/refill functions such as orchestrating and synchronizing the material deposition device movement, dispense action and vacuum actuation are within the bounds of the invention. The computer systems can be programmed to interface between the user specified template sequence and the position of a material deposition device to deliver the correct reagents to specified regions of the surface.

Figure 7:
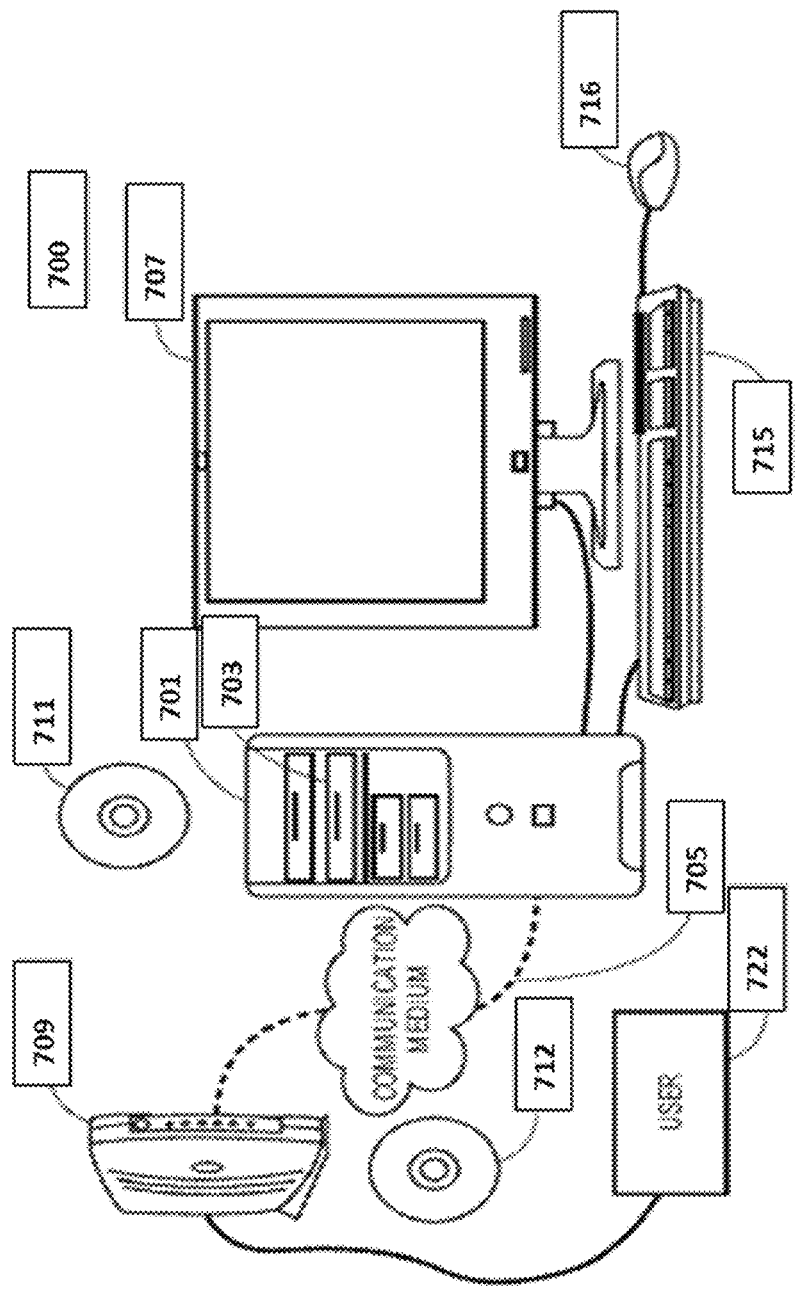
FIG. 7 illustrates a computer system.

The computer system 700 illustrated in FIG. 7 can be understood as a logical apparatus that can read instructions from media 711 and/or a network port 705, which can optionally be connected to server 709 having fixed media 712. The system, such as shown in FIG. 7 can include a CPU 701, disk drives 703, optional input devices such as keyboard 715 and/or mouse 716 and optional monitor 707. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 722 as illustrated in FIG. 7.

Figure 8:
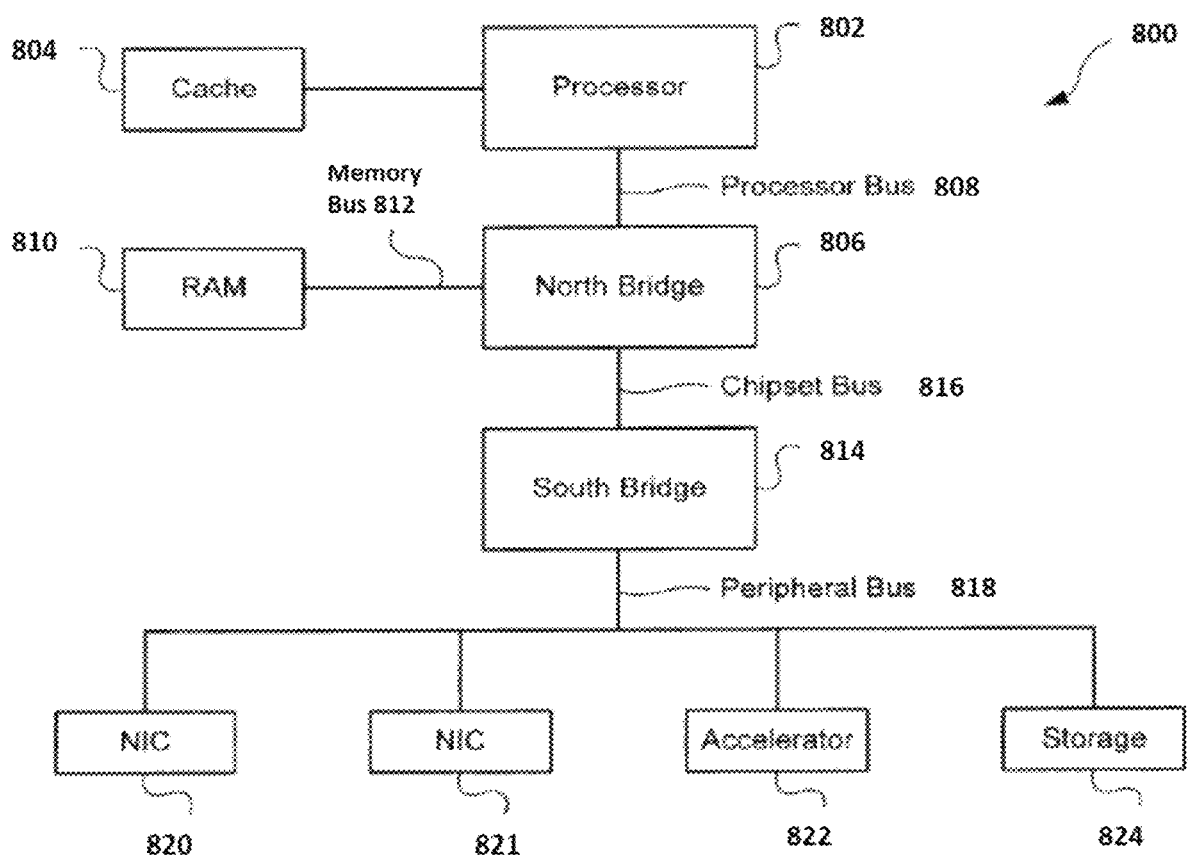
FIG. 8 is a block diagram illustrating architecture of a computer system.

Provided herein is a block diagram illustrating a first example architecture of a computer system 800 that can be used in connection with example instances of the present invention as shown in FIG. 8. As depicted in FIG. 8, the example computer system can include a processor 802 for processing instructions. Non-limiting examples of processors include: Intel Xeon™ processor, AMD Opteron™ processor, Samsung 8-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices.

As illustrated in FIG. 8, a high speed cache 804 can be connected to, or incorporated in, the processor 802 to provide a high speed memory for instructions or data that have been recently, or are frequently, used by processor 802. The processor 802 is connected to a north bridge 806 by a processor bus 808. The north bridge 806 is connected to random access memory (RAM) 810 by a memory bus 812 and manages access to the RAM 810 by the processor 802. The north bridge 806 is also connected to a south bridge 88 by a chipset bus 816. The south bridge 814 is, in turn, connected to a peripheral bus 818. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 818. In some alternative architectures, the functionality of the north bridge can be incorporated into the processor instead of using a separate north bridge chip. In some instances, system 800 can include an accelerator card 822 attached to the peripheral bus 818. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 824 and can be loaded into RAM 810 and/or cache 804 for use by the processor. The system 800 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example instances of the present invention. In this example, system 800 also includes network interface cards (NICs) 820 and 821 connected to the peripheral bus for providing network interfaces to external storage, such as Network Attached Storage (NAS) and other computer systems that can be used for distributed parallel processing.

Figure 9:
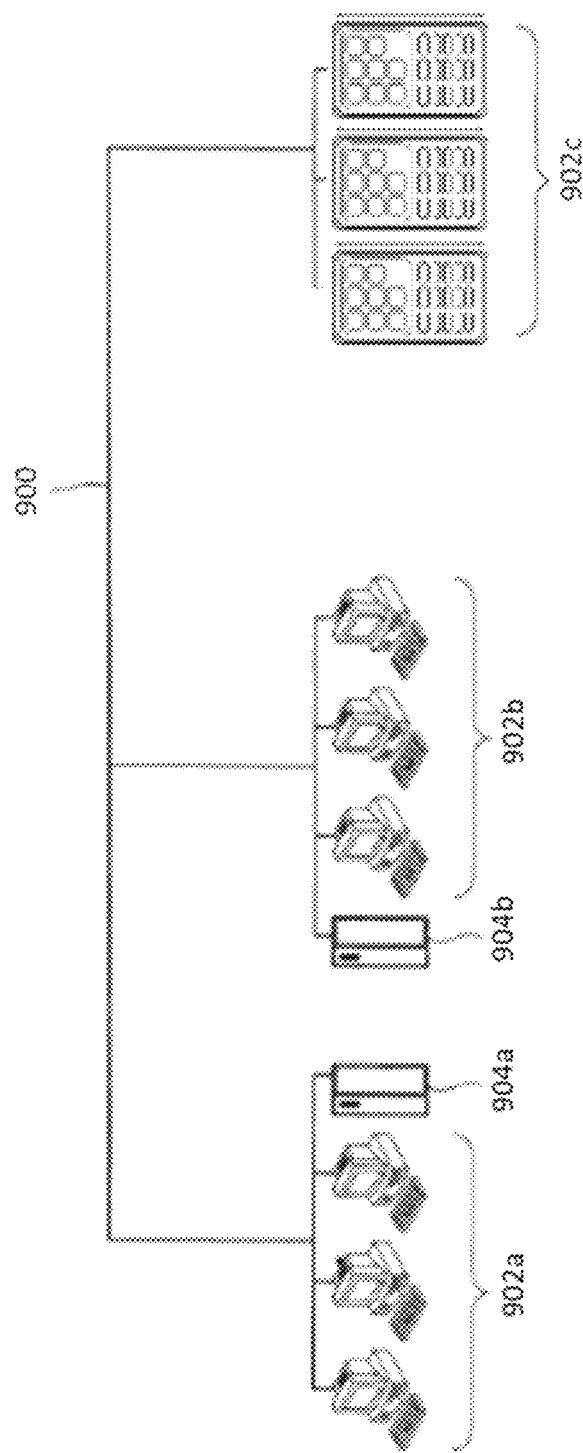
FIG. 9 is a diagram demonstrating a network configured to incorporate a plurality of computer systems, a plurality of cell phones and personal data assistants, and Network Attached Storage (NAS).

Provided herein is a diagram showing a network 900 with a plurality of computer systems 902a, and 902b, a plurality of cell phones and personal data assistants 902c, and Network Attached Storage (NAS) 904a, and 904b as shown in FIG. 9. In example instances, systems 902a, 902b, and 902c can manage data storage and optimize data access for data stored in Network Attached Storage (NAS) 904a and 904b. A mathematical model can be used for the data and be evaluated using distributed parallel processing across computer systems 902a, and 902b, and cell phone and personal data assistant systems 902c. Computer systems 902a, and 902b, and cell phone and personal data assistant systems 902c can also provide parallel processing for adaptive data restructuring of the data stored in Network Attached Storage (NAS) 904a and 904b. FIG. 9 illustrates an example only, and a wide variety of other computer architectures and systems can be used in conjunction with the various instances of the present invention. For example, a blade server can be used to provide parallel processing. Processor blades can be connected through a back plane to provide parallel processing. Storage can also be connected to the back plane or as Network Attached Storage (NAS) through a separate network interface.

In some example instances, processors can maintain separate memory spaces and transmit data through network interfaces, back plane, or other connectors for parallel processing by other processors. In other instances, some or all of the processors can use a shared virtual address memory space.

Figure 10:
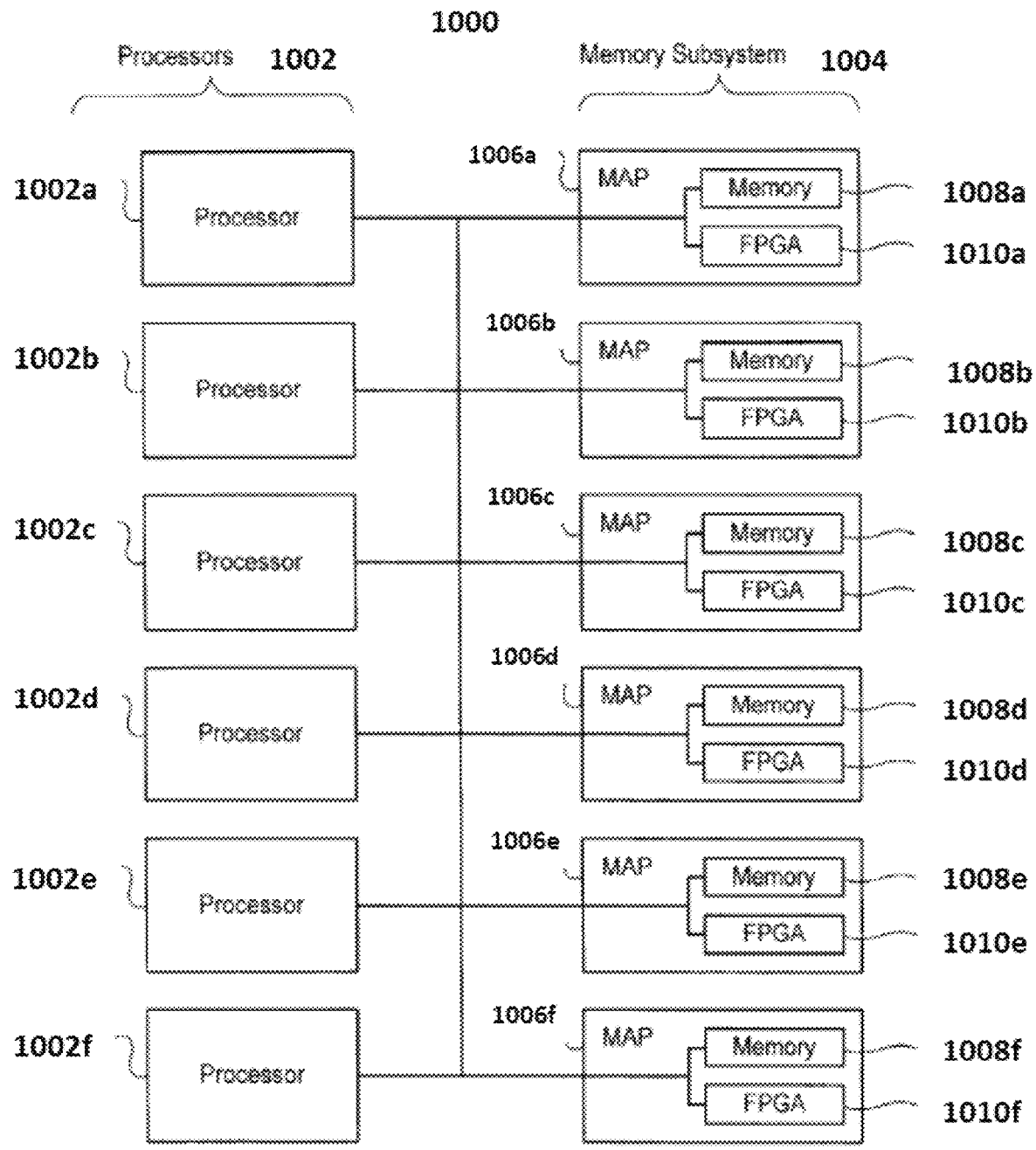
FIG. 10 is a block diagram of a multiprocessor computer system using a shared virtual address memory space.

Provided herein is a block diagram of a multiprocessor computer system 1000 using a shared virtual address memory space as illustrated in FIG. 10 in accordance with an example embodiment. The system includes a plurality of processors 1002 comprising 1002a-f that can access a shared memory subsystem 1004. The system incorporates a plurality of programmable hardware memory algorithm processors (MAPs) 1006a-f in the memory subsystem 1004. Each MAP 1006a-f can comprise a memory 1008a-f and one or more field programmable gate arrays (FPGAs) 1010a-f. The MAP provides a configurable functional unit and particular algorithms or portions of algorithms can be provided to the FPGAs 1010a-f for processing in close coordination with a respective processor. For example, the MAPs can be used to evaluate algebraic expressions regarding the data model and to perform adaptive data restructuring in example instances. In this example, each MAP is globally accessible by all of the processors for these purposes. In one configuration, each MAP can use Direct Memory Access (DMA) to access an associated memory 1008a-f, allowing it to execute tasks independently of, and asynchronously from the respective microprocessor 1002a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example instances, including systems using any combination of general processors, co-processors, FPGAs and other programmable logic devices, system on chips (SOCs), application specific integrated circuits (ASICs), and other processing and logic elements. In some instances, all or part of the computer system can be implemented in software or hardware. Any variety of data storage media can be used in connection with example instances, including random access memory, hard drives, flash memory, tape drives, disk arrays, Network Attached Storage (NAS) and other local or distributed data storage devices and systems.

In example instances, the computer system can be implemented using software modules executing on any of the above or other computer architectures and systems. In other instances, the functions of the system can be implemented partially or completely in firmware, programmable logic devices such as field programmable gate arrays (FPGAs) as referenced in FIG. 10, system on chips (SOCs), application specific integrated circuits (ASICs), or other processing and logic elements. For example, the Set Processor and Optimizer can be implemented with hardware acceleration through the use of a hardware accelerator card, such as accelerator card 722 illustrated in FIG. 7.

Other Embodiments

In some aspects, provided herein is a method of detecting a target nucleic acid sequence in a sample, said method comprising contacting said sample with at least one microdroplet comprising a pair of primers, wherein said at least one microdroplet contains a volume of equal to or less than 250 nL, and amplifying said target nucleic acid sequence in said sample, thereby detecting said target nucleic acid sequence in said sample. In some embodiments, said at least one microdroplet comprises said pair of primers at a concentration of at least 1 µM. In some embodiments, said at least one microdroplet further comprises a probe at a concentration of at least 1 µM. In some embodiments, contacting said sample with two or more microdroplets each comprising said pair of primers, wherein each of said two or more microdroplets has a volume of 2.5 nL. In some embodiments, contacting said sample with 50-100 microdroplets each comprising said pair of primers, wherein each of said 50-100 microdroplets has a volume of 2.5 nL. In some embodiments, each of said microdroplets has a volume of 25 nL, in which embodiment, ten times (10×) fewer number of microdroplets can be used in each reaction compared to using microdroplets with the volume of 2.5 nL.

In some aspects, provided herein is a method of amplifying a target nucleic acid sequence in a sample, said method comprising preparing a reaction pre-mixture comprising said sample and a polymerase, wherein said reaction pre-mixture does not comprise a primer, contacting said reaction pre-mixture with a microdroplet comprising a pair of primers to form a reaction mixture, wherein said microdroplet contains a volume of equal to or less than 250 nL, and amplifying said target nucleic acid sequence by thermal cycling in said reaction mixture, wherein said amplification has a lower limit of detection (LoD) as compared to an amplification by thermal cycling in a reaction mixture comprising a sample, a polymerase, and a pair of primers that are pre-mixed prior to amplification. In some embodiments, said amplification is commenced within 50 milliseconds after said contacting. In some embodiments, said amplification is commenced within 30 seconds after said contacting. In some embodiments, said amplification is commenced after 30 seconds of said contacting.

In some aspects, provided herein is a method of amplifying a target nucleic acid sequence in a plurality of samples, said method comprising: amplifying said target nucleic acid in each of said plurality of samples in a reaction mixture, wherein when said reaction mixture contains a volume of equal to or less than 10 µL, said amplification has a limit of detection (LoD) of 1000 molecules per mL, wherein said LoD is determined by a lowest concentration of the target nucleic acid that allows amplification to be detected when amplified in a plurality of positive control samples each having the lowest concentration of the target nucleic acid sequence, wherein amplification is detected in at least 95% of the plurality of the positive controls. In some aspects, provided herein is a method of amplifying a target nucleic acid sequence in a plurality of nucleic acid samples extracted from contrived or collected biological samples, said method comprising: amplifying said target nucleic acid in each of said plurality of samples in a reaction mixture, wherein when said reaction mixture contains a volume of equal to or less than 10 µL, said amplification has a limit of detection (LoD) of 3000 molecules per mL, as measured by amplification with serially diluted positive controls. In some embodiments, when said reaction mixture contains a volume of equal to or less than 10 µL, said amplification has a limit of detection (LoD) of 200 molecules per mL, wherein said LoD is determined a lowest concentration of the target nucleic acid sequence that allows amplification to be detected when amplified in a plurality of samples each having a biological component comprising the lowest concentration of the target nucleic acid, wherein amplification is detected in at least 95% of the plurality of samples, optionally wherein the target nucleic acid sequence is a viral nucleic acid sequence and the biological form is an inactivated particle. In some embodiments, said plurality of samples comprises 96-2000 samples. In some embodiments, said plurality of samples comprises at least 384 samples. In some embodiments, said plurality of samples comprises at least 1536 samples.

In some aspects, provided herein is a method of detecting a target nucleic acid sequence in a plurality of samples at a rate of at least 10000 samples per day with a single device, said method comprising contacting each of said plurality of samples with a pair of primers and amplifying said target nucleic acid sequence in each of said plurality of samples, thereby detecting said target nucleic acid sequence in each of said plurality of samples, wherein said detection has a sensitivity of at least 95% as calibrated with a positive control. In some embodiments, said detection has a rate of at least 15000 samples per day.

In some aspects, provided herein is a method for simultaneously detecting two or more target nucleic acid sequences in a plurality of samples at a rate of at least 10000 samples per day in a single device, said method comprising contacting said plurality of samples with two or more pairs of primers on a plate comprising a plurality of wells, wherein each well comprises one of said plurality of samples and one pair of said two or more pairs of primers, wherein each one pair of said two or more pairs of primers hybridizes with one of said two or more target nucleic acid sequences, wherein said plurality of wells comprise different pairs of said two or more pairs of primers, and amplifying one of said two or more target nucleic acid sequences in each well to a threshold level, thereby detecting said two or more target nucleic acid sequences in said plurality of samples, wherein said amplification of said detection has a sensitivity of at least 95% as calibrated with a positive control.

In some embodiments, said two or more target nucleic acid sequences are nucleic acid sequences of different genes. In some embodiments, said two or more target nucleic acid sequences are from different organisms. In some embodiments, each of said two or more target nucleic acid sequences hybridizes with only one pair of said two or more pairs of primers. In some embodiments, each of said two or more pairs of primers has a concentration of 1 µM-500 µM prior to said contacting. In some embodiments, each of said two or more pairs of primers has a concentration of 100 µM prior to said contacting. In some embodiments, each of said two or more pairs of primers has a concentration of 200 µM prior to said contacting. In some embodiments, each of said plurality of samples are positioned on said reaction plate in a pre-determined manner. In some embodiments, said contacting is performed by an automated liquid handler.

In some embodiments, at least one of said two or more target nucleic acid sequences comprise DNA or RNA. In some embodiments, said two or more target nucleic acid sequences comprise DNA and RNA. In some embodiments, said DNA is viral DNA. In some embodiments, said viral DNA is from hepatitis B, adenovirus, papillomavirus, poxvirus, herpesvirus, herpes simplex virus, varicella zoster virus, Epstein-Barr virus, or cytomegalovirus. In some embodiments, said DNA comprises DNA from a bacterium, a fungus, or a parasite. In some embodiments, said bacterium comprises *Streptococcus pyogenes*, coliform, *Escherichia coli, Salmonella, Shigella, Staphylococcus aureus, Gardnerella vaginalis, Neisseria gonorrhoeae, Chlamydia trachomatis, Treponema pallidum, Clostridium difficile, Mycobacterium tuberculosis, Bordetella pertussis, Streptococcus pneumoniae, Mycoplasma pneumoniae, Haemophilus influenzae, Legionella pneumophila, Neisseria meningitidis, Listeria monocytogenes, Borrelia burgdorferi, Vibrio cholerae, Clostridium botulinum, Clostridium tetani*, or *Bacillus anthracis*. In some embodiments, said fungus comprises *Candida albicans, Trichophyton, Microsporum, Epidermophyton, Trichophyton rubrum, Epidermophyton floccosum, Aspergillus, Histoplasma capsulatum, Cryptococcus neoformans, Cryptococcus gattii, Coccidioides* or *Blastomyces*. In some embodiments, said parasite comprises a protozoa, a helminth, or an ectoparasite.

In some embodiments, said RNA comprises viral RNA. In some embodiments, said two or more target nucleic acid sequences comprise a nucleic acid from severe acute respiratory syndrome coronavirus 2 (SARS-CoV-2), human immunodeficiency virus (HIV), influenza virus, Dengue virus, hepatitis C virus, hepatitis E virus, ebolavirus, lyssavirus, poliovirus, West Nile virus, Human T-cell lymphotropic virus type 1 (HTLV-1), respiratory syncytial virus (RSV), parainfluenza virus (NV), human metapneumovirus (hMPV), human rhinovirus (HRV), severe acute respiratory syndrome coronavirus 1 (SARS-CoV-1), middle east respiratory syndrome coronavirus (MERS-CoV), or measles virus.

In some embodiments, each of said two or more target nucleic acid sequences is amplified by at least 5 fold after 40 amplification cycles in each of said plurality of samples. In some embodiments, said target nucleic acid sequence is amplified by at least 5 fold after 40 amplification cycles in said sample. In some embodiments, said target nucleic acid sequence is amplified by at least 5 fold after 40 amplification cycles in each of said plurality of samples.

In some embodiments, said amplification is performed in a reaction mixture. In some embodiments, said reaction mixture has a volume of about 2.5 µL. In some embodiments, said reaction mixture has a volume of about 0.5 to about 20 µL. In some embodiments, said reaction mixture has a volume of about 0.5 to about 10 µL. In some embodiments, said reaction mixture has a volume of about 0.5 to about 1 µL. In some embodiments, said reaction mixture comprises a polymerase, deoxynucleotide triphosphates (dNTPs), DNAse/RNAse-free water, or an amplification buffer. In some embodiments, said reaction mixture comprises a reverse transcriptase. In some embodiments, said polymerase comprises a DNA-dependent DNA polymerase or an RNA-dependent DNA polymerase. In some embodiments, said polymerase comprises a DNA-dependent DNA polymerase and an RNA-dependent DNA polymerase.

In some embodiments, said amplification has at least 91%, 92%, 93%, 94%, 95%, 96%, 97%, 98%, or at least 99% sensitivity relative to a positive control amplification. In some embodiments, said amplification has at least 95% sensitivity relative to a positive control amplification. In some embodiments, said amplification has at least 91%, 92%, 93%, 94%, 95%, 96%, 97%, 98%, or at least 99% sensitivity relative to a negative control amplification. In some embodiments, said amplification has at least 95% sensitivity relative to a negative control amplification.

In some embodiments, said amplification has an LoD of 10-200 molecules per mL as determined by amplification with standard positive controls. In some embodiments, said LoD is 10 molecules per mL as determined by amplification with standard positive controls. In some embodiments, said LoD is 50 molecules per mL as determined by amplification with standard positive controls. In some embodiments, said LoD is 100 molecules per mL as determined by amplification with standard positive controls. In some embodiments, said LoD is 200 molecules per mL as determined by amplification with standard positive controls.

In some embodiments, the method further comprises detecting said target nucleic acid sequence in said sample in said reaction mixture. In some embodiments, said detection has an LoD of 100-2000 molecules per mL as determined by amplification with standard positive controls. In some embodiments, said LoD is 100 molecules per mL as determined by amplification with standard positive controls. In some embodiments, said LoD is 500 molecules per mL as determined by amplification with standard positive controls. In some embodiments, said LoD is 1000 molecules per mL as determined by amplification with standard positive controls. In some embodiments, said LoD is 2000 molecules per mL as determined by amplification with standard positive controls.

In some embodiments, said target nucleic acid sequence is DNA. In some embodiments, said two or more target nucleic acid sequences is viral DNA. In some embodiments, said viral DNA is from hepatitis B, adenovirus, papillomavirus, poxvirus, herpesvirus, herpes simplex virus, varicella zoster virus, Epstein-Barr virus, or cytomegalovirus. In some embodiments, said DNA comprises DNA from a bacterium, a fungus, or a parasite. In some embodiments, said bacterium comprises *Streptococcus pyogenes*, coliform, *Escherichia coli*, *Salmonella*, *Shigella*, *Staphylococcus aureus*, *Gardnerella vaginalis*, *Neisseria gonorrhoeae*, *Chlamydia trachomatis*, *Treponema pallidum*, *Clostridium difficile*, *Mycobacterium tuberculosis*, *Bordetella pertussis*, *Streptococcus pneumoniae*, *Mycoplasma pneumoniae*, *Haemophilus influenzae*, *Legionella pneumophila*, *Neisseria meningitidis*, *Listeria monocytogenes*, *Borrelia burgdorferi*, *Vibrio cholerae*, *Clostridium botulinum*, *Clostridium tetani*, or *Bacillus anthracis*. In some embodiments, said fungus comprises *Candida albicans*, *Trichophyton*, *Microsporum*, *Epidermophyton*, *Trichophyton rubrum*, *Epidermophyton floccosum*, *Aspergillus*, *Histoplasma capsulatum*, *Cryptococcus neoformans*, *Cryptococcus gattii*, *Coccidioides* or *Blastomyces*. In some embodiments, said parasite comprises a protozoa, a helminth, or an ectoparasite.

In some embodiments, said target nucleic acid sequence is RNA. In some embodiments, said target nucleic acid sequence is viral RNA. In some embodiments, said viral RNA is from severe acute respiratory syndrome coronavirus 2 (SARS-CoV-2). In some embodiments, said viral RNA is from human immunodeficiency virus (HIV), influenza virus, Dengue virus, hepatitis C virus, hepatitis E virus, ebolavirus, lyssavirus, poliovirus, West Nile virus, Human T-cell lymphotropic virus type 1 (HTLV-1), respiratory syncytial virus (RSV), parainfluenza virus (PIV), human metapneumovirus (hMPV), human rhinovirus (HRV), severe acute respiratory syndrome coronavirus 1 (SARS-CoV-1), middle east respiratory syndrome coronavirus (MERS-CoV), or measles virus.

In some embodiments, said reaction mixture further comprises a pair of primers. In some embodiments, said pair of primers has a concentration of 1 µM-500 µM prior to said contacting. In some embodiments, said pair of primers has a concentration of 100 µM prior to said contacting. In some embodiments, said pair of primers has a concentration of 200 µM prior to said contacting. In some embodiments, said reaction mixture further comprises a probe. In some embodiments, said reaction mixture further comprises two or more probes. In some embodiments, said amplification comprises polymerase chain reaction thermocycling.

In some embodiments, said sample is extracted from a biological sample. In some embodiments, each of said plurality of samples is extracted from a biological sample. In some embodiments, said biological sample comprises nasopharyngeal fluid, oropharyngeal fluid, saliva, blood, sera, plasma, lavage, urine, ear exudate, cerebrospinal fluid (CSF), sputum, saliva, bone marrow, synovial fluid, aqueous humor, amniotic fluid, cerumen, breast milk, auroral pharyngeal lavage fluid, bronchoalveolar lavage, bronchoalveolar lavage fluid, semen, prostatic fluid, Cowper's fluid, pre-ejaculatory fluid, female ejaculate, sweat, tears, cyst fluid, pleural fluid, peritoneal fluid, pericardial fluid, lymph, chyme, chyle, bile, interstitial fluid, menses, pus, sebum, vaginal secretion, mucosal secretion, stool, stool water, pancreatic juice, lavage fluid from sinus cavities, bronchopulmonary aspirate, blastocoel cavity fluid, or umbilical cord blood. In some embodiments, said biological sample is obtained from a human subject. In some embodiments, said biological sample is treated with N-acetylcysteine (NAC) before each of said plurality of samples is extracted from said biological sample. In some embodiments, said biological sample is heat-inactivated before each of said plurality of samples is extracted.

EXAMPLES

These examples are provided for illustrative purposes only and not to limit the scope of the claims provided herein.

Example 1: SARS-CoV-2 qPCR Probe Assay (SCV2 Test)

A real-time RT-PCR (rRT-PCR) assay is used for the qualitative detection of nucleic acid from the SARS-CoV-2 virus in nasopharyngeal, nasal, and/or oropharyngeal swab specimens in viral transport media (VTM), universal transfer media (UTM) or DNA/RNA Shield obtained from individuals suspected of COVID-19. This assay employs the CDC-designed primer/probe sequences as included in the SARS-CoV-2 (2019-nCoV) CDC qPCR Probe Assay. SARS-CoV-2-specific sequences target two separate regions of the viral nucleocapsid (N) gene. Also included is an internal control targeting the human RNase P (RP) gene. All three targets are detected in a single assay in multiplex, each with a unique fluorophore-quencher combination. Specific primer and probe sequences for detection of SARS-CoV-2 RNA and human control are listed in Table 1. Instruments that can be used to perform the test are indicated in Table 2.

Results are for the identification of SARS-CoV-2 RNA. The SARS-CoV-2 RNA is generally detectable in the upper respiratory tract during the acute phase of infection. Positive results (e.g., detection of SARS-CoV-2 nucleic acid in the sample) are indicative of the presence of SARS-CoV-2 RNA; clinical correlation with patient history and other diagnostic information is necessary to determine patient infection status. Negative results do not preclude SARS-CoV-2 infection and can be combined with clinical observations, patient history, and epidemiological information such as a patient's recent exposures, history, presence of clinical signs and symptoms consistent with COVID-19 to make decisions for patient management.

TABLE 1

Specific primer and probe sequences for detection of SARS-CoV-2 RNA and human control

| Name | Description | Oligo-Nucleotide Sequence (5'>3') | Label | Quencher | Conc. (nM) | Target |
|---|---|---|---|---|---|---|
| nCoV_N1-F | SARS-CoV-2 N1 Forward Primer | GACCCCAAAATCAGCGAAAT (SEQ ID NO: 1) | NA | NA | 315 | SARS-CoV-2 N |

TABLE 1-continued

Specific primer and probe sequences for detection of SARS-CoV-2 RNA and human control

| Name | Description | Oligo-Nucleotide Sequence (5'>3') | Label | Quencher | Conc. (nM) | Target |
|---|---|---|---|---|---|---|
| nCoV_N1-R | SARS-CoV-2 N1 Reverse Primer | TCTGGTTACTGCCAGTTGAATCTG (SEQ ID NO: 2) | NA | NA | 315 | SARS-CoV-2 N |
| nCoV_N1-P | SARS-CoV-2 N1 Probe | ACCCCGCATTACGTTTGGTGGACC (SEQ ID NO: 3) | FAM | BHQ-1 | 78.75 | SARS-CoV-2 N |
| nCoV_N2-F | SARS-CoV-2 N2 Forward Primer | TTACAAACATTGGCCGCAAA (SEQ ID NO: 4) | NA | NA | 202.5 | SARS-CoV-2 N |
| nCoV_N2-R | SARS-CoV-2 N2 Reverse Primer | GCGCGACATTCCGAAGAA (SEQ ID NO: 5) | NA | NA | 202.5 | SARS-CoV-2 N |
| nCoV_N2-P | SARS-CoV-2 N2 Probe | ACAATTTGCCCCCAGCGCTTCAG (SEQ ID NO: 6) | VIC/HEX | BHQ-1 | 50.625 | SARS-CoV-2 N |
| RP-F | RNase P Forward Primer | AGATTTGGACCTGCGAGCG (SEQ ID NO: 7) | NA | NA | 90 | Human RNase P |
| RP-R | RNase P Reverse Primer | GAGCGGCTGTCTCCACAAGT (SEQ ID NO: 8) | NA | NA | 90 | Human RNase P |
| RP-P | RNase P Probe | TTCTGACCTGAAGGCTCTGCGCG (SEQ ID NO: 9) | CY5 | BHQ-2 | 22.5 | Human RNase P |

TABLE 2

Instruments that can be used to carry out the test

| Instrument | Manufacturer | Procedure step |
|---|---|---|
| OT-2 | Opentrons | Sample reformatting |
| CyBio FeliX | Analytik Jena | RNA extraction and add RNA to rRT-PCR plates |
| Cobra | Art Robbins Instruments | Master plate manufacture |
| Echo 550 or 650 | LabCyte (550) Beckman (650) | Primer/probe and PCR control distribution |
| Lightcycler 480 II | Roche | rRT-PCR |

A protocol designed for high-throughput sample reformatting, RNA extraction, and rRT-PCR is followed using a heavily automated robotic workflow and the steps are as follows:
1) Heat inactivation of clinical specimens in a laboratory convection oven at 65° C. for 1 hour.
2) Automated sample reformatting of samples from sample tubes to 96-well sample blocks using the Opentrons OT-2 liquid handling robot.
3) Automated RNA extraction using the Analytik Jena CyBio FeliX instrument with the Applied Biosystems Mag-MAX Viral Pathogen II reagent kit.
4) Manufacturing of 384 well plates using an ArtRobbins Cobra bulk dispenser.
5) Assembly of 384 well plates using an Analytik Jena CyBio Felix instrument to dispense RNA samples and a LabCyte (or Beckman) Echo to dispense primer/probe sets and PCR controls.
6) Real time rRT-PCR using Roche LightCycler 480 II instrument and the One Step PrimeScript™ III RT-qPCR Kit (TaKaRa Bio, Cat #RR600A).
Controls to be Used:
Positive PCR Control
Synthetic SARS-CoV-2 RNA. Control reactions are run with synthetic RNA near the PCR LOD at 3.2 copies/μL.

These controls (16 copies/µL, 3.2 copies/4, and 0.64 copies/µL) are added directly to the PCR plate. RP (human RNase P) cDNA at 1000 copies/4, is also added to each of these controls. Each positive PCR control is included with each rRT-PCR run as a single reaction.

Negative PCR Control

Water, certified RNase/DNase-Free. This control is added directly to the PCR plate and is included with each rRT-PCR run as a single reaction.

Internal PCR/Extraction Control

Each clinical sample is subjected to detection of a human gene (RNase P, RP) expected to be present in each sample. This control is internal to each individual reaction.

Negative Extraction Control

VTM or DNA/RNA Shield containing no virus or human cells. This control is included in each extraction run and proceeds through the entire test pipeline through rRT-PCR detection.

Assay Results and Interpretation

All test control results are examined prior to interpretation of patient results. If control results are invalid, the patient results cannot be interpreted. A rRT-PCR/RT-qPCR cycle threshold (Ct) value of <40 is required for a detected sample for either the N1 or N2 assays. Samples resulting in detection of either the N1 or N2 assays are considered positive. A summary of the assay interpretation is presented in Table 3.

TABLE 3

Interpretation of test results

| N1 | N2 | RP | SARS CoV-2 interpretation |
|---|---|---|---|
| + | + | +/− | Detected |
| − | − | + | Not detected |
| + | − | +/− | Detected |
| − | + | +/− | Detected |
| − | − | − | Invalid |

Example 2: Performance Evaluation

1) Validation Data Summary

SCV2 test was validated by measuring the Limit of Detection (LoD measured as inactivated virus copies/mL) in contrived spike-in specimens, and by comparison to a cohort of clinical specimens previously run on another FDA EUA-approved platform.

The LoD of detection was determined to be 200 virus copies/mL of specimen, defined by detecting 100% (20/20) of 20 extraction replicates at that spike-in concentration. The LoD assay is elaborated in the next sections. The assay performance was compared against a panel of positive and negative clinical specimens tested on another sensitive FDA EUA-approved assay. 97.5% (39/40) agreement with the positive cohort and 95% (38/40) agreement with the negative cohort was obtained. This assay data is further elaborated in the next sections.

2) Limit of Detection (LoD)—Analytical Sensitivity

An initial LOD study was performed by spiking heat-inactivated SARS-CoV-2 virus (ATCC VR-1986HK) into PBS across a wide dilution series from 0 to 2,000 virus/mL. Spike-in samples were extracted in triplicate and detected using the standard rRT-PCR protocol. Viral RNA was detected in 100% of triplicate samples at the lowest spike-in of 100 virus/mL. See Table 4.

TABLE 4

Initial triplicate LOD determined at a wide spike-in concentration Virus/mL

| Replicate | Target | 2,000 | 1,000 | 500 | 300 | 200 | 100 | 0 | 0 |
|---|---|---|---|---|---|---|---|---|---|
| 1 | N1 | 33.9 | 35.0 | 36.6 | 37.8 | 36.8 | 37.9 | — | — |
|   | N2 | 32.9 | 34.2 | 35.5 | 36.7 | 35.5 | 36.1 | — | — |
| 2 | N1 | 33.6 | 35.1 | 35.1 | 38.3 | 36.2 | 37.9 | — | — |
|   | N2 | 32.8 | 34.5 | 34.9 | 35.7 | 36.0 | — | — | — |
| 3 | N1 | 34.5 | 35.0 | 36.7 | 36.3 | 37.3 | 38.2 | — | — |
|   | N2 | 33.6 | 34.9 | 35.2 | 35.5 | — | 36.6 | — | — |

The specific LOD was further evaluated by performing 20 replicate extractions at each of three virus dilutions around the putative initial LOD from the first triplicate experiment. SARS-CoV-2 was successfully detected in 20/20 (100%) replicates at 200 virus/mL, placing the extraction LOD at or below 200 viral copies/mL. See Table 5-1 for a summary of the 20 replicate LOD experiment results.

A subsequent experiment was performed in negative matrix at 300 and 200 virus/mL. 95% detection was observed at 300 virus/mL. Thus, the overall LOD is 300 virus/mL (Table 5-2).

TABLE 5-1

Final LOD determination with 20 replicates at three low virus concentrations

| Virus/mL | Target | 1 | 2 | 3 | 4 | 5 | 6 | 7 | 8 | 9 | 10 | 11 |
|---|---|---|---|---|---|---|---|---|---|---|---|---|
| 400 | N1 | 34.9 | 35.8 | 35.8 | 39.3 | 34.8 | 35.2 | 35.0 | 36.0 | 35.7 | 36.0 | 35.2 |
|   | N2 | 35.3 | 35.7 | 34.8 | 35.1 | 36.7 | 35.7 | 35.9 | 35.8 | 35.5 | 35.7 | 34.6 |
| 300 | N1 | 36.1 | 35.9 | 35.1 | 36.3 | 37.1 | 35.2 | 36.9 | 35.8 | 34.7 | 35.2 | 35.8 |
|   | N2 | 35.6 | 35.3 | — | 35.5 | 36.1 | 35.8 | 36.5 | 36.2 | 35.5 | 35.2 | 37.1 |
| 200 | N1 | 35.8 | 35.9 | 36.1 | 35.3 | 36.1 | 36.0 | 36.8 | 36.6 | 37.0 | 36.2 | 36.1 |
|   | N2 | 36.1 | 35.7 | 36.3 | 35.8 | 34.9 | 35.0 | 35.6 | 36.1 | 36.6 | 37.2 | 36.1 |
| 100 | N1 | 38.4 | — | — | 37.0 | 36.7 | 39.6 | 35.7 | 39.1 | 36.7 | 37.1 | — |
|   | N2 | — | 38.2 | — | 36.6 | 36.6 | — | — | 37.0 | 37.8 | 38.2 | — |

| Virus/mL | Target | 12 | 13 | 14 | 15 | 16 | 17 | 18 | 19 | 20 |
|---|---|---|---|---|---|---|---|---|---|---|
| 400 | N1 | 36.1 | 35.2 | 35.9 | 36.5 | 35.7 | 35.5 | 35.9 | 35.9 | 35.7 |
|   | N2 | 35.9 | 35.9 | 35.1 | 35.5 | 35.6 | 35.6 | 35.7 | 35.4 | 34.8 |
| 300 | N1 | 36.4 | 36.6 | 35.6 | 36.4 | 35.9 | 36.0 | 36.1 | — | 36.8 |
|   | N2 | 36.3 | 35.6 | 35.5 | 36.2 | 36.2 | 35.1 | 35.6 | 36.3 | 35.7 |

TABLE 5-1-continued

Final LOD determination with 20 replicates
at three low virus concentrations

| 200 | N1 | — | 37.7 | 36.8 | 35.8 | 36.2 | 36.8 | 35.8 | 36.6 | 36.9 |
| | N2 | 35.9 | 36.9 | — | 36.6 | 37.5 | 36.7 | 37.3 | 35.6 | 36.2 |
| 100 | N1 | — | 35.8 | 36.1 | 37.1 | 35.9 | — | 36.7 | — | — |
| | N2 | — | — | 36.1 | — | 37.1 | 36.7 | 36.7 | — | 35.8 |

Final LOD determination with 20 replicates at two low
virus concentrations diluted in negative clinical matrix

| Virus/mL | Target | 1 | 2 | 3 | 4 | 5 | 6 | 7 | 8 | 9 | 10 | 11 |
|---|---|---|---|---|---|---|---|---|---|---|---|---|
| 200 | N1 | 36.7 | 35.9 | 37.6 | 35.9 | — | 35.7 | 36.8 | 36.9 | — | 37.6 | 37.6 |
| | N2 | — | 35.0 | 36.2 | 35.0 | — | 35.1 | 35.6 | 35.3 | 35.5 | 36.2 | 36.0 |
| 100 | N1 | 36.5 | 37.8 | 37.0 | 37.0 | 37.3 | 35.7 | 34.7 | 37.6 | 37.2 | — | 37.1 |
| | N2 | — | 35.5 | 35.9 | — | — | 35.2 | 34.6 | 35.8 | 35.5 | 35.9 | 35.9 |

| Virus/mL | Target | 12 | 13 | 14 | 15 | 16 | 17 | 18 | 19 | 20 |
|---|---|---|---|---|---|---|---|---|---|---|
| 200 | N1 | 37.6 | 36.0 | — | 37.6 | — | 36.2 | 36.6 | 36.4 | 37.8 |
| | N2 | — | 34.9 | 35.6 | 36.0 | 35.5 | — | — | 35.8 | 35.4 |
| 100 | N1 | — | — | — | 37 | — | 37 | 37 | 37 | — |
| | N2 | — | 35.9 | 36.1 | 35.9 | — | — | 35.8 | — | 35.9 |

3) Clinical Evaluation:

To evaluate the test described herein in Example 1 against clinical samples, a set of 80 previously tested clinical nasopharyngeal swab specimens was obtained (40 positive, 40 negative). These specimens were originally tested on another currently available platform (Platform C). Specimen aliquots were heat-inactivated after testing on the platform C and prior to running them on the assay described herein in Example 1. A comparison of the results of the test described herein in Example 1 to the clinical results is presented in Table 6.

Positive Percent Agreement 40 positive samples were tested, and of these, 39 tested positive with our test, resulting in 97.5% concordance between the SCV2 test in Example 1 and the Platform C, an EUA approved platform. 24 of the 40 tested positive samples had Ct >30.0 on the Platform C, of which was detected 24/24 (100%).

Negative Percent Agreement

Of 40 negative samples tested, 38 were negative by the SCV2 test for 95% negative concordance.

TABLE 6

Summary of comparative results with
previously tested clinical specimens

| | Platform C Results | | | SCV2 test Results | | |
|---|---|---|---|---|---|---|
| Sample | N2 | E | Call | N1 | N2 | Call |
| 1 | — | — | Negative | — | — | Negative |
| 2 | — | — | Negative | — | — | Negative |
| 3 | — | — | Negative | — | — | Negative |
| 4 | — | — | Negative | — | — | Negative |
| 5 | — | — | Negative | — | — | Negative |
| 6 | — | — | Negative | — | — | Negative |
| 7 | — | — | Negative | — | — | Negative |

TABLE 6-continued

Summary of comparative results with
previously tested clinical specimens

| | Platform C Results | | | SCV2 test Results | | |
|---|---|---|---|---|---|---|
| Sample | N2 | E | Call | N1 | N2 | Call |
| 8 | — | — | Negative | — | — | Negative |
| 9 | — | — | Negative | — | — | Negative |
| 10 | — | — | Negative | — | — | Negative |
| 11 | — | — | Negative | — | — | Negative |
| 12 | — | — | Negative | — | — | Negative |
| 13 | — | — | Negative | — | — | Negative |
| 14 | — | — | Negative | — | — | Negative |
| 15 | — | — | Negative | — | — | Negative |
| 16 | — | — | Negative | — | — | Negative |
| 17 | — | — | Negative | — | — | Negative |
| 18 | — | — | Negative | — | — | Negative |
| 19 | — | — | Negative | — | — | Negative |
| 20 | — | — | Negative | — | — | Negative |
| 21 | — | — | Negative | — | — | Negative |
| 22 | — | — | Negative | — | — | Negative |
| 23 | — | — | Negative | — | — | Negative |
| 24 | — | — | Negative | 35.1 | 35.7 | Positive* |
| 25 | — | — | Negative | — | — | Negative |
| 26 | — | — | Negative | — | — | Negative |
| 27 | — | — | Negative | — | — | Negative |
| 28 | — | — | Negative | — | — | Negative |
| 29 | — | — | Negative | — | — | Negative |
| 30 | — | — | Negative | — | — | Negative |
| 31 | — | — | Negative | — | — | Negative |
| 32 | — | — | Negative | — | — | Negative |
| 33 | — | — | Negative | — | — | Negative |
| 34 | — | — | Negative | — | — | Negative |
| 35 | — | — | Negative | — | — | Negative |
| 36 | — | — | Negative | 35.5 | 34.9 | Positive* |
| 37 | — | — | Negative | — | — | Negative |
| 38 | — | — | Negative | — | — | Negative |
| 39 | — | — | Negative | — | — | Negative |
| 40 | — | — | Negative | — | — | Negative |
| 41 | 24.7 | 22.4 | Positive | 24.8 | 24.6 | Positive |

TABLE 6-continued

Summary of comparative results with previously tested clinical specimens

| Sample | Platform C Results | | | SCV2 test Results | | |
|---|---|---|---|---|---|---|
| | N2 | E | Call | N1 | N2 | Call |
| 42 | 28.0 | 25.9 | Positive | 26.0 | 25.7 | Positive |
| 43 | 20.9 | 18.5 | Positive | 33.1 | 32.5 | Positive |
| 44 | 33.0 | 30.6 | Positive | 31.6 | 31.1 | Positive |
| 45 | 40.2 | 39.0 | Positive | 38.6 | 36.8 | Positive |
| 46 | 38.6 | 36.0 | Positive | 35.5 | 34.7 | Positive |
| 47 | 38.3 | 35.2 | Positive | 35.1 | 35.3 | Positive |
| 48 | 40.2 | 41.7 | Positive | 37.6 | 36.1 | Positive |
| 49 | 37.7 | 34.5 | Positive | 36.2 | 36.8 | Positive |
| 50 | 36.6 | 36.5 | Positive | 32.3 | 32.0 | Positive |
| 51 | 37.0 | 33.9 | Positive | 32.0 | 31.7 | Positive |
| 52 | 24.3 | 23.8 | Positive | 25.2 | 24.9 | Positive |
| 53 | 20.4 | 18.2 | Positive | 19.5 | 19.2 | Positive |
| 54 | 35.5 | 32.0 | Positive | 34.0 | 33.0 | Positive |
| 55 | 32.6 | 29.7 | Positive | 27.0 | 26.7 | Positive |
| 56 | 35.0 | 31.5 | Positive | 32.6 | 32.1 | Positive |
| 57 | 25.9 | 23.6 | Positive | 24.7 | 24.4 | Positive |
| 58 | 34.7 | 31.8 | Positive | 31.6 | 31.3 | Positive |
| 59 | 28.5 | 25.7 | Positive | — | — | Negative |
| 60 | 41.3 | 40.5 | Positive | 38.7 | 37.5 | Positive |
| 61 | 36.0 | 32.1 | Positive | 35.7 | 34.8 | Positive |
| 62 | 41.1 | 39.8 | Positive | 36.5 | 36.2 | Positive |
| 63 | 31.2 | 28.6 | Positive | 30.1 | 29.7 | Positive |
| 64 | 32.0 | 29.5 | Positive | 31.6 | 31.3 | Positive |
| 65 | 24.1 | 22.7 | Positive | 23.8 | 23.8 | Positive |
| 66 | 35.7 | 32.7 | Positive | 34.2 | 33.6 | Positive |
| 67 | 38.3 | 36.4 | Positive | 34.9 | 34.5 | Positive |
| 68 | 27.9 | 25.5 | Positive | 26.4 | 26.1 | Positive |
| 69 | 25.2 | 23.1 | Positive | 25.7 | 25.6 | Positive |
| 70 | 18.7 | 16.4 | Positive | 18.1 | 17.8 | Positive |
| 71 | 30.8 | 28.1 | Positive | 31.0 | 30.6 | Positive |
| 72 | 27.3 | 25.7 | Positive | 30.4 | 30.0 | Positive |
| 73 | 25.0 | 23.5 | Positive | 26.4 | 25.9 | Positive |
| 74 | 26.7 | 24.2 | Positive | 30.9 | 30.9 | Positive |
| 75 | 34.1 | 31.2 | Positive | 34.0 | 34.0 | Positive |
| 76 | 29.9 | 27.9 | Positive | 29.0 | 28.6 | Positive |
| 77 | 36.9 | 33.2 | Positive | 33.0 | 32.1 | Positive |
| 78 | 29.5 | 26.3 | Positive | 28.7 | 28.5 | Positive |
| 79 | 39.6 | 38.7 | Positive | 37.9 | — | Positive |
| 80 | 30.2 | 27.6 | Positive | 31.2 | 30.9 | Positive |

*The two discordant samples #24 and #36 were retested three times and gave positive calls in 3/3 repeats of the SCV2 test in Example 1.

4) Inter-Assay Reproducibility

To demonstrate reproducibility across days, a set of 5 positive and 5 negative clinical samples were selected and tested across three different days. The results of these tests are outlined below in Table 11. In brief, the 5 positive and 5 negative specimens in each assay were successfully identified.

TABLE 11

Inter-assay reproducibility

| Day | Target | Positive | | | | | Negative | | | | |
|---|---|---|---|---|---|---|---|---|---|---|---|
| 1 | N1 | 21.7 | 24.1 | 19.6 | 26.8 | 34.7 | — | — | — | — | — |
| | N2 | 21.2 | 23.9 | 19.0 | 27.5 | 33.7 | — | — | — | — | — |
| 2 | N1 | 21.1 | 23.7 | 19.0 | 25.9 | 33.7 | — | — | — | — | — |
| | N2 | 21.7 | 24.5 | 20.6 | 26.8 | 34.5 | — | — | — | — | — |
| 3 | N1 | 21.7 | 24.2 | 19.7 | 26.3 | 34.3 | — | — | — | — | — |
| | N2 | 21.5 | 23.9 | 20.3 | 26.7 | 34.6 | — | — | — | — | — |

5) Intra-Assay Reproducibility

Intra-assay reproducibility is demonstrated by the LoD experiments, where multiple contrived spike-in samples were assayed at several dilutions in triplicate and in 20-replicate, including near and at the limit of detection. These assays were performed by multiple technicians and on multiple days.

Example 3: Sample Reformatting Standard Operating Procedure

Figure 2A:
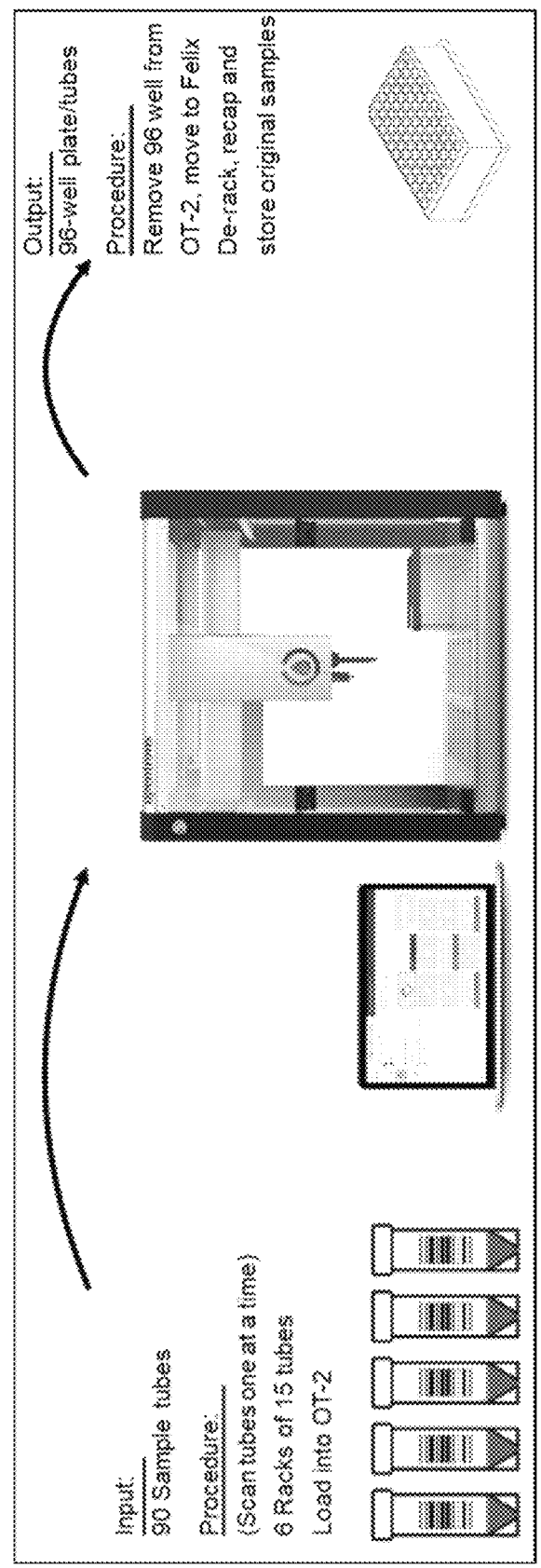
FIG. 2A depicts a schematic of sample reformatting procedure.

This procedure is for reformatting individual samples received into 96-well format suitable for high throughput RT-qPCR testing for COVID-19 (FIG. 2A).

Figure 2B:
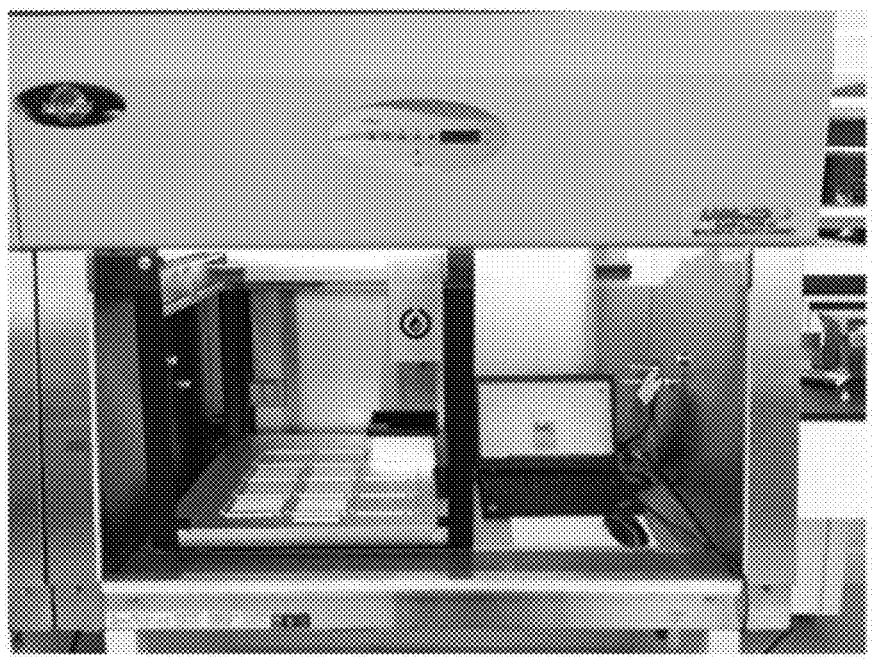
FIG. 2B shows an image of an exemplary device (OT-2 robotics) in a Biological Safety Cabinet (BSC).

Materials and Instruments:
Stainless tweezer (for removing swab from 5 ml specimen tube if necessary)
Box of pipette tips
Empty pipette tip box for used tips
Empty 96 deep well Sample plate
Three pre-accessioned 32-sample racks (1 each of Blue, Green, Yellow) from ready-for-reformatting refrigerator
Clear rubber caps (size would be 16 mm) for 10/15 ml tube and Blue rubber caps (size would be 13 mm) for 5 ml tube
Aluminum plate seal
Plate seal roller
PPE—include face shield as tube is being uncapped
Opentrons OT-2 robotics
Biosafety Cabinet
OT-2 Deck for manual reformatting
96 deep well adapter for manual reformatting on OT-2 deck
OT-2 in Biosafety Cabinet (FIG. 2B):

Procedures:

A. Opentrons OT-2 testing: At the beginning of a shift and before any reformatting, perform a calibration check using the calibration kit following the "9—maintenance and Calibration_OT-2_reformatting SOP". If any misalignment of the pipet with tubes is noticed, have a specialist trained for re-calibration to re-calibrate the instrument.

B. Opentrons OT-2 Reformatting: There will be separate OT2 robots calibrated for different tubes (5-mL tubes or 10/15-mL tubes). Please check the instrument and use the right instrument for the tube size that are reformatted.

Figure 2C:
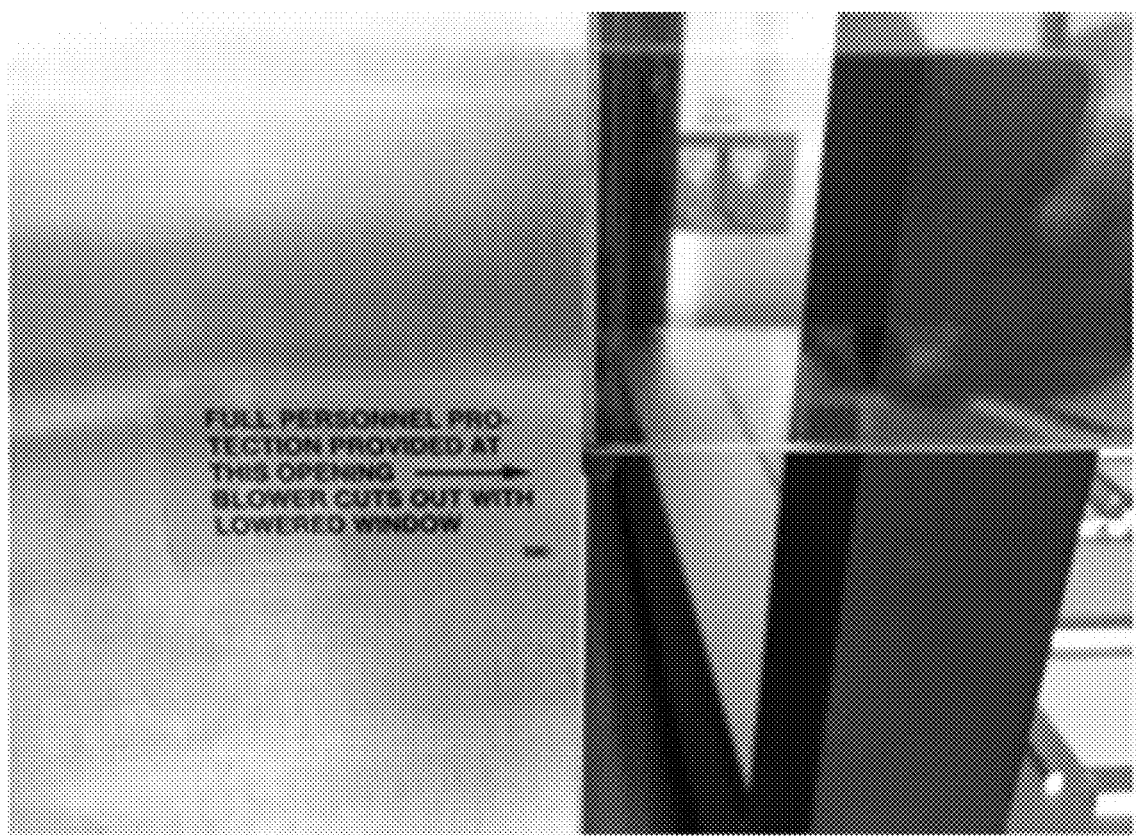
FIG. 2C shows an image of a safety sign on a Biological Safety Cabinet (BSC).

Note: The OT-2 are located in Biological Safety Cabinets (BSCs). The BSC needs to be always on and the window needs to stay at the sash height (as indicated by the sign on the side of the BSC as in FIG. 2C. This position provides full personal protection. The alarm will go off if the window is above the sash height and the blower will cut off if the window is below the sash height).

(1) Retrieve three color coded sample racks (one color each, blue, green and yellow) from the Heat Inactivated Sample refrigerator. Racks should be retrieved from the fridge with first in, first out priority (FIFO). As the tri-color racks are stored together in the pre-reformatting refrigerator from top to bottom with the earliest on the top and latest on the bottom, please take racks from the oldest shelf as indicated by the magnetic indicator. There are multiple tri-color racks, the color does not indicate first in, only their position (order) in the fridge indicates first in. The color coded racks ensure the correct positioning of controls for the reformatted 96 Deep well plate.

(2) Retrieve one empty barcoded 96 deep well sample plate from the plastic storage bin under the workbench. Keep the plate face down to minimize any potential contamination.

Figure 2D:
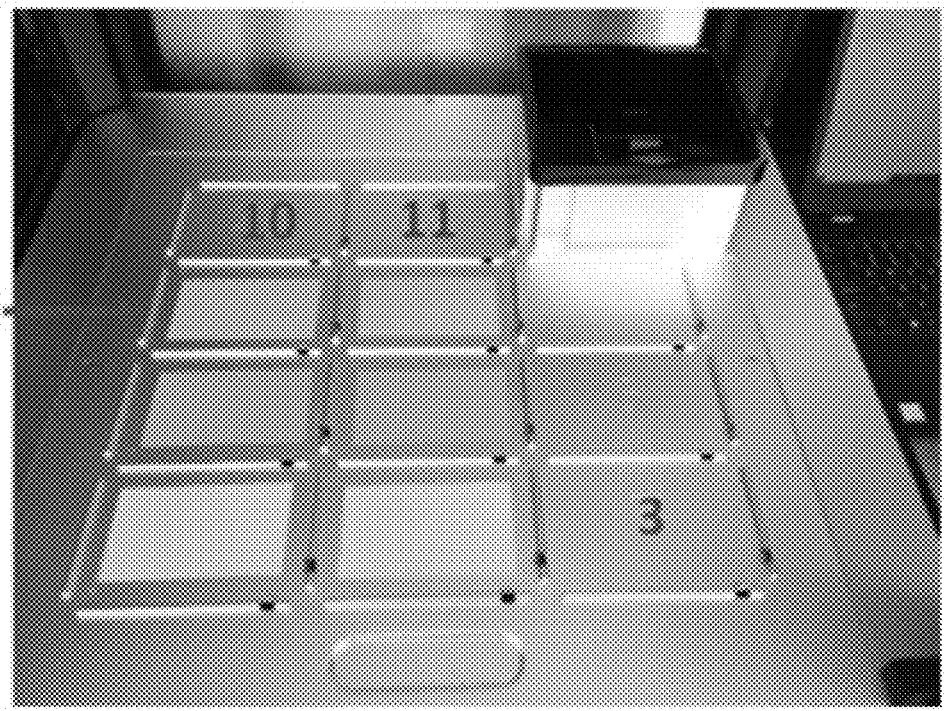
FIG. 2D shows an image depicting locations of slots on OT-2 deck.

(3) Load a new rack of p1000 filter tips pipette tips onto slot 10 of the OT2 deck. If there is an empty rack from a prior run in slot 10, transfer it to slot 11 or obtain a new empty tip rack and place it in slot 11. (See FIG. 2D for location for each).

(4) Launch the Reformat Rack to 96 well module of the DaViD Tracker software if not already running on the reformatting station computer. The cursor should automatically highlight rack barcode field.

(5) For each sample rack (back to front: Blue, Green, then Yellow).

(5-a) Scan the rack barcode, and then starting at position A1 (top left), lift each sample tube from the rack and scan the sample barcode.

(5-b) Scan each tube in the rack, moving across the rows first, from top left to bottom right (see diagram below). The Yellow rack should have 30 sample tubes with 1 control tube at D7 and an intentional empty space at position D8.

(5-c) Cells in the tracker will have the sample barcode populated (as they were scanned in from accessioning and grayed out). The barcode will become solid if the scanned sample barcode is verified to be in the correct rack at the correct position.

(5-d) Cells will turn orange, and an audible message will play if samples barcodes are duplicates or in an incorrect position. If the tube is in an incorrect location, Investigate the reason and correct it when it happens. If the issue cannot be resolved, bring the attention to a supervisor and the supervisor will investigate.

(5-e) Cells will turn red and a message will display if an illegal barcode is scanned (e.g., a rack barcode). Scan the correct barcode to correct.

(5-f) Manual entry of the barcode may be used if the barcode is not scannable. (Note: Cells will be pre-filled in gray text with the expected code to aid in identifying any errors during scanning.)

(5-g) Place the rack in the correct OT2 slot. Make sure that the rack is correctly seated between slot barriers on all four sides and notch on the top left corner. (Note: Racks should be placed on the OT2 deck according to the color code on the deck: Blue rack into blue slot, green rack into green slot, and yellow rack into yellow slot. The A1 slot (the notched corner) should always be at the back left.)

(5-h) Proceed to decap the tubes on the current rack before scanning and placing the next rack. (Note: Take extra care when decapping tubes to avoid spillage and cross contamination. Do not drop the decapped sample tube back into the rack as it will cause liquid to fly out of the tube and contaminate nearby samples If liquid gets onto gloves, immediately change gloves and discard the contaminated gloves into a biohazard waste container.)

Figure 2E:
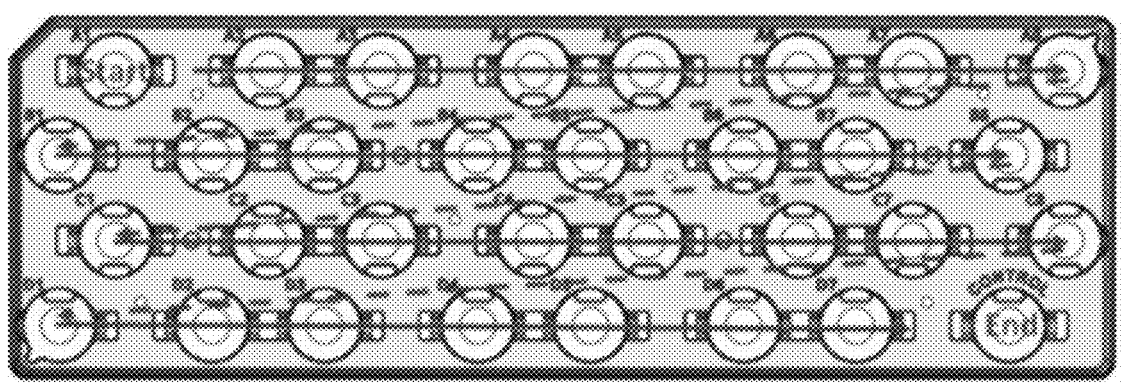
FIG. 2E shows a diagram depicting the order of decapping procedure.
Figure 2F:
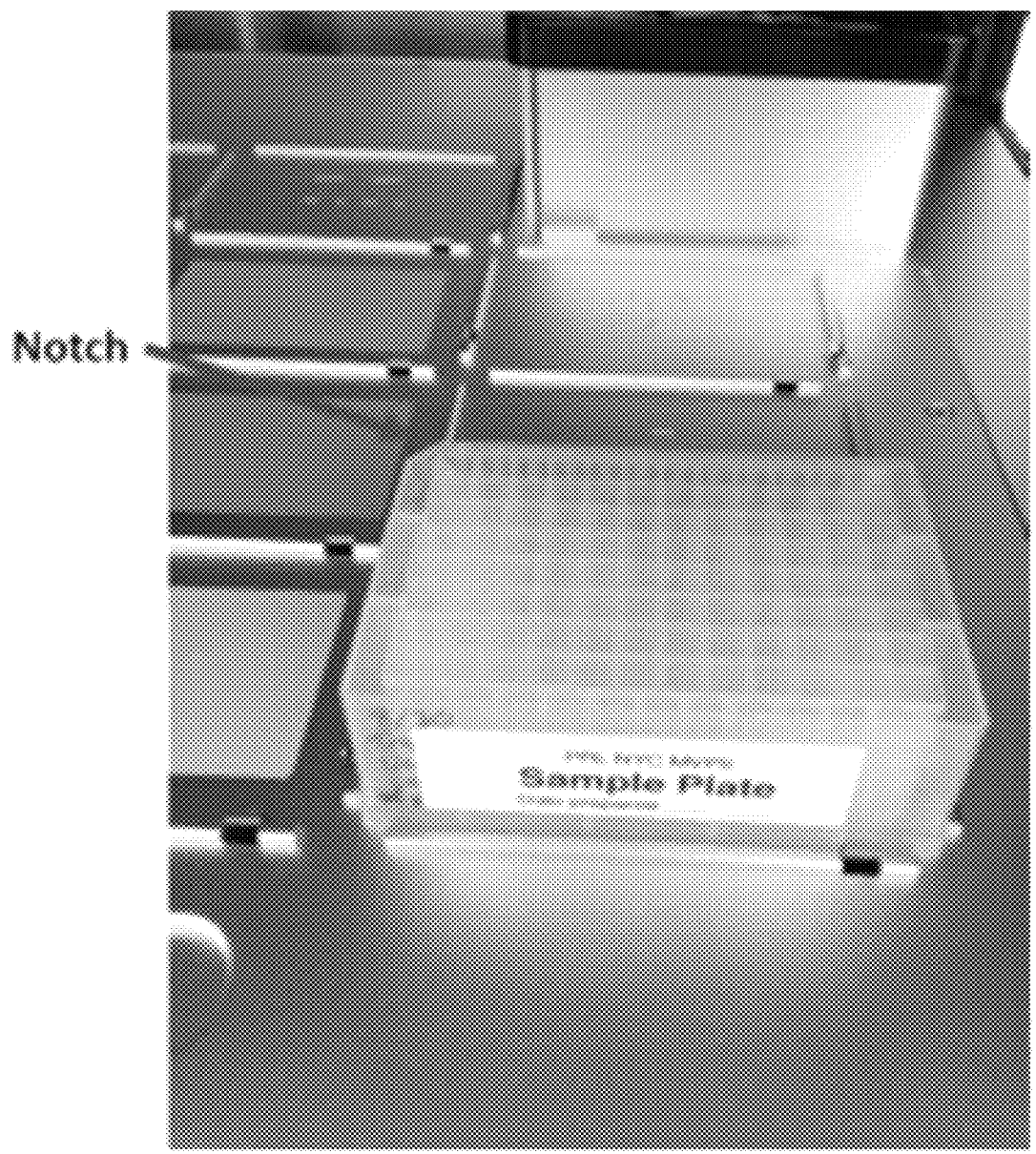
FIG. 2F shows an image depicting the placement of a 96-well Deep Well plate on the OT-2 deck.

(5-i) Decapping procedure: Tubes should be decapped in the same order as the tubes were scanned, starting from the back left (A1) and moving across rows to the front right (D8) (see diagram in FIG. 2E). (The scanning and decapping order is shown in FIG. 2E. This is the yellow ReOpen rack, the Blue and Green Reopen rack should be scanned and decapped in similar order but end at D8 location instead of D7.)

(5-i-a) For 10-15 ml tubes: Keeping the sample tubes in their rack positions and taking care to not move the rack from its deck position, lift one sample tube up, unscrew the tube cap to the almost off but not quite yet, slowly put the tube down into the rack, then unscrew the cap all the way, lift the cap and turn it upside down, and discard the cap into the waste container on the OT-2 deck.

(5-i-b) For 5 ml tubes: Decap the tubes and remove the swab in the sample tube at the same time. Decapping is the same as (i), after removing tube cap and discard into the waste container on the OT-2 deck and before moving on to next sample tube, use a stainless steel tweezer to remove the swab in the sample tube and discard the swab into a biohazard waste container and dispose the stainless steel tweezer into a sharps container. Gently put the sample tube back in the rack without dropping the sample tube.

Note: Turn the cap over to have the bottom facing up as it is moved over the other samples to the biohazard trash, to avoid any dripping of the sample off the lid into other samples.

(6) Once all three racks have been scanned and verified, scan the 96 Deep Well plate barcode into the plate barcode field and click 'Save' to submit the resulting 96-well plate to DaViD. There will be a popup message confirming that the plate was successfully submitted and the rack codes were archived.

(7) Remove the waste container from the OT-2 deck and discard the caps it contained into a biohazard waste container nearby and put the waste container back onto OT-2 deck.

(8) Load the 96-well Deep Well plate onto OT-2 deck at slot 3 with the notch on the upper left corner. Make sure the plate sits securely in the slot with the slot barrier.

(9) Thoroughly check that all racks and the Sample plate are properly seated in the OT2 slots, and all tubes are properly seated in the racks (i.e., vertical and not tilted).

(10) In the Opentrons software on the reformatting computer, make sure the '15 mL and 10 mL REFORMATTING_96_SAMPLES_SINGLE_PIPETTE.PY" protocol is loaded.

(11) Select the 'Run' tab and click 'Start run'.

(12) The OT-2 will begin the run, which will take approximately 55 minutes.

(12-a) The OT-2 front status light will change color according to the following:

(12-a-i) Yellow—Protocol is running.

(12-a-ii) Green—Protocol has completed. Press "resume" in App to finish the run.

(12-a-iii) Blue—Robot is idle.

(13) Monitor the beginning of the run for the first two columns of yellow rack to make sure the run proceeds normally before moving to another machine. Continue to monitor the run periodically to verify it is proceeding normally.

(14) When the run is complete, remove the 96 deep well sample plate from OT-2.

(15) Take an aluminum plate seal and remove paper backing to expose the glue side of the seal. Apply the seal to the plate with the glue side facing the top of the plate. Use a plate seal roller and roll over the plate to ensure a proper seal. Take care to avoid introducing creases or folds in the foil seal, as this will result in a poor seal and possible cross-contamination.

(16) Transfer sealed plate to 'ready for extraction' fridge.

(17) Recap samples according to following procedure (use clear 16 mm rubber cap for 10 or 15 ml tubes and blue 13 mm rubber cap for 5 ml tubes).

Figure 2G:
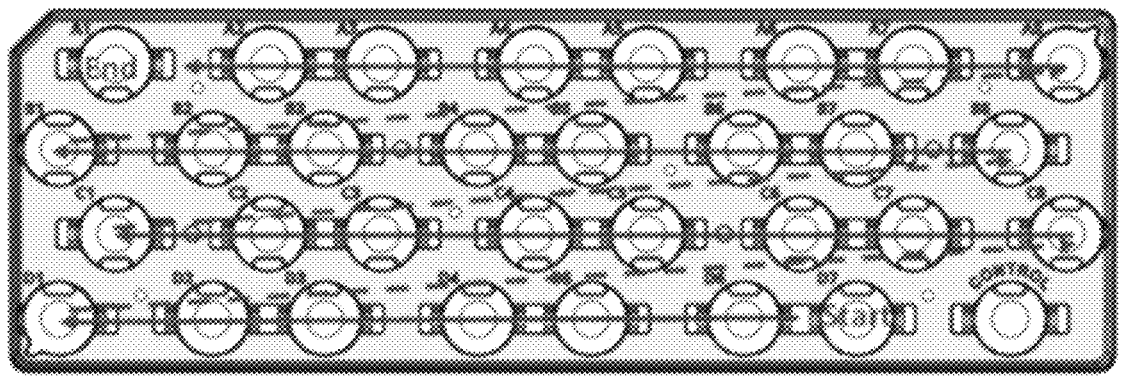
FIG. 2G shows a diagram depicting the order of recapping procedure.

(18) Move in reverse order to how they were placed in the robot and uncapped (i.e., from the front of the deck to the back, see FIG. 2G).

(18-a) Carefully push one of the rubber caps into each sample tube as deep as it will fit.

(18-b) Remove racks that are completely recapped before moving to the next rack to ensure sufficient workspace.

(19) Recapped samples should be placed in a sample storage rack and moved to the sample remainder fridge.

(20) Remove the now full used pipette tip box from deck slot 11 and discard in a sharp container. Move the now empty pipette tip box from slot 10 to slot 11 for the next run.

Note: At the end of a shift, the preparer or the technician should not leave if there is any reformatting running. Wait until the reformatting run finishes and seal the reformatted 96 Deep well sample plate. All reformatted 96 Deep Well plates need to be sealed and put into "Ready for RNA extraction refrigerator". Plan work accordingly.

C. Manual Reformatting: Manual reformatting is only necessary for a small percentage of samples. If too many samples need to go through manual reformatting, it may impact the turnaround time and the issue will need to be addressed with sample collection sites. If manual reformatting is necessary (samples are too viscous or other reasons) samples should be reformatted with the following procedure:

(1) Retrieve three color coded sample racks designated for manual reformatting from the reformatting refrigerator.

(2) Retrieve one pre-barcoded 96 deep well plate and keep the plate face down on the bench.

(3) Retrieve Manual Reformatting Adapter and place on deck of OT-2 in the bottom right deck slots (see FIG. 2H).

(4) Launch the ReformatSample module of the DaViD Tracker software if not already running on the reformatting station computer.

(5) Scan the 96-well plate barcode and load into the manual reformatting adapter on the reformatting deck. The plate can only slide in one way with the notch on the lower left corner. The cursor will jump to the rack barcode field of the first 32-well rack.

(6) Working with one rack at a time in the order of Blue, Green, and Yellow, for each sample rack:

(6-a) Scan the rack barcode and then starting at A1 (top left, see FIG. 2E) position, lift the sample from the rack and scan the barcode.

(6-b) Scan each tube in the rack, moving across the row first from top left to bottom right. Yellow racks will have 31 specimen tube slots and one control slot empty in D8.

(6-c) In DaViD, fields will turn green if the scanned specimen barcode is verified to be in the correct rack at the correct position.

(6-d) Fields will turn orange if samples are duplicate barcodes or in an incorrect position. Investigate the reason and correct it when it happens.

(6-e) Cells will turn red if an illegal barcode is scanned (i.e., a rack barcode). Scan the correct barcode to correct.

(6-f) If the barcode cannot be scanned, manually enter the barcode.

(6-g) Place the rack into the correct deck slot (Blue in blue slot, Green in green slot and Yellow in yellow slot). Make sure that the rack is firmly seated between the deck slot barriers on all four sides (see deck images above indicating the deck slot barriers for ReOpen Rack).

Figure 2I:
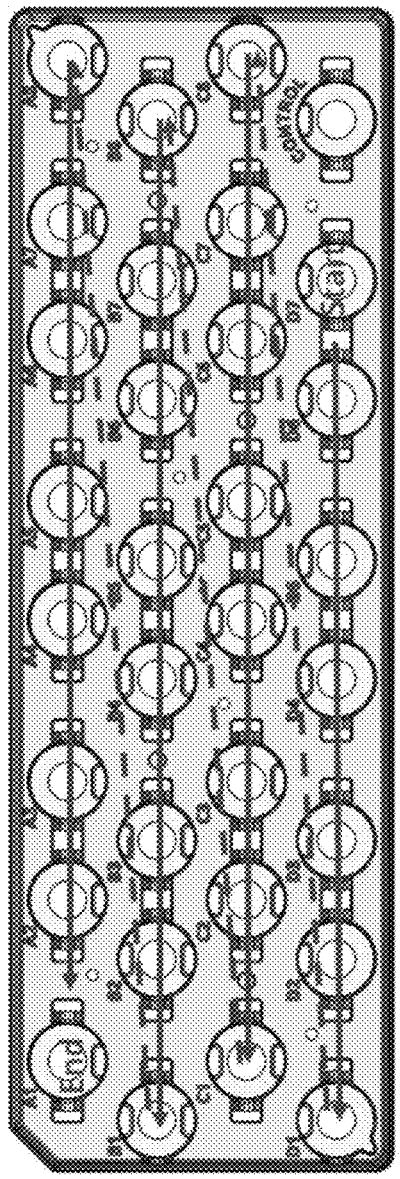
FIG. 2I shows a diagram depicting the order of decapping and manual transferring procedure.

(6-h) Moving from the top right tube in A8, across rows first and to the bottom left, decap each sample tube, discard the cap into biohazard waste, and manually transfer 400 μL of sample from the tube to the specified 96-well plate well according to the sample tube to 96 deep well plate mapping on the screen and near the manual reformatting station and in FIG. 2I.

Note: Racks should be placed on the deck according to color code. Blue rack in blue slot, green rack in green slot, and yellow rack in yellow slot.

(6-i) Cap the sample tube by carefully pushing a rubber cap into the sample tube and put the tube back into the rack before moving on to the next sample until the whole rack is finished. Use Clear rubber caps (size would be 16 mm) for 10/15 mL tube and Blue rubber caps (size would be 13 mm) for 5 mL tube.

(7) When all three color coded racks have been reformatted, seal the plate with foil seal and roller and transfer the plate to the "ready for extraction" fridge.

(8) Place recapped samples on the storage rack and move to sample storage fridge.

(9) If there are not enough samples to fill all three racks, the samples can be spread out on the three racks but all three racks should be used so that samples can be tested (without waiting for more samples).

Example 4: Preparation of Reagents for RNA Extraction and RT-qPCR Procedures

This procedure is for preparing reagents used in the RNA extraction and RT-qPCR procedures.

Equipment and materials are summarized in Table 7 and Table 8.

TABLE 7

Summary of equipment

| Item | Manufacturer | Cat. No. | No. |
| --- | --- | --- | --- |
| Isotemp General Purpose Lab Refrigerator | Fisherbrand | FBG49RPGA | 0 |
| General Purpose-20 Freezer | VWR | U2020GA14 | 0 |
| OT-2 robot | Opentrons | OT-2 | 2 |
| Opentrons P1000 single channel pipette gen2 | Opentrons | | 2 |
| 2-in-1 Bluetooth Barcode Scanner | TaoTronics | TT-BS030 | 2 |
| TempPlate sealing foil | USA Scientific | 2923-0110 | 8 |
| Soft rubber roller | Speedball | 4126 | 1 |
| CyBio FeliX | Analytik Jena AG | 30-5015-500-24 | 2 |
| Bioshake 3000-T elm | Analytik Jena AG | OL3317-11-120 | 2 |
| Microplate gripper | Analytik Jena AG | OL3317-11-800 | 2 |
| CyBio FeliX Head R 96/1000 uL | Analytik Jena AG | OL3316-14-950 | 2 |
| CyBio FeliX Support 97 mm | Analytik Jena AG | OL3317-11-105 | 4 |
| CyBio FeliX Support 37 mm | Analytik Jena AG | OL3317-11-120 | 2 |
| CyBi TipRack 96-1000 uL | Analytik Jena AG | OL3811-25-939-F | 8 |

TABLE 8

Summary of materials

| Item | Manufacturer | Cat. No. | No. |
| --- | --- | --- | --- |
| Hard-Shell ® 96-Well PCR Plates, low profile, thin wall, skirted, white/clear | BioRad | HSP9621 | 2 |
| 96-well Clear V-Bottom 2 mL Polypropylene Deep Well Plate | Corning | 3961 | 4 |
| MagMAX Viral/Pathogen II Kit | Applied Biosystems | A48383 | 1 |
| DNAse/RNAse Free Water | Zymo Research | W1001-30 | 1 |
| Apricot iPIPETTEPRO | Apricot Design | iPPPro | 1 |
| 384 well plate for Echo Source Plate | LABCYTE Inc | PP 0200 | 1 |
| Synthetic SARS-CoV-2 RNA control 1 (MT007544.1) | Twist Bioscience | 102019 | |
| 2019-nCoV_N_Positive Control | Integrated DNA Technologies | 10006625 | |
| Hs_RPP30 Positive Control | Integrated DNA Technologies | 10006626 | |
| MERS-CoV Control | Integrated DNA Technologies | 10006623 | |

TABLE 8-continued

Summary of materials

| Item | Manufacturer | Cat. No. No. |
|---|---|---|
| SARS-CoV Control | Integrated DNA Technologies | 10006624 |
| nCOV_N1 Forward Primer, | SynBio Technologies | |
| nCOV_N1 Reverse Primer, | SynBio Technologies | |
| nCOV_N1 Probe, | SynBio Technologies | |
| nCOV_N2 Forward Primer, | SynBio Technologies | |
| nCOV_N2 Reverse Primer, | SynBio Technologies | |
| nCOV_N2 Probe, | SynBio Technologies | |
| RNase P Forward Primer, | SynBio Technologies | |
| RNase P Reverse Primer, | SynBio Technologies | |
| RNase P Probe, | SynBio Technologies | |

Preparation:

Reagents are arrayed into 96-deep well plates according to RNA extraction kit manufacturer (Applied Biosystems) and either stored according to manufacturer before using or loaded directly onto robot.

Primers and probes are diluted to 250 µM stock solutions. Working solutions are prepared and dispensed into Echo source plates for storage and dispensing into light cycler reaction plates by the Echo.

Controls are prepared in PCR tubes for dispensing into Echo source plate and then dispensed into PCR plate by Echo.

Storage and Stability: Control stock solution and diluted working solutions are stored in −20° C. freezer. RNA extraction reagents are stored at room temperature.

Procedure: These procedures prepare multiple reagents used in RNA extraction and RT-qPCR procedures. These reagents need to be prepared at specific locations and using specific equipment to minimize the chance of contamination and ensure test sensitivity and specificity. Store the prepared reagents in specified locations. Please follow the procedure carefully. To perform these procedures, please wear standard PPE and fresh gloves.

(A) Negative RT-qPCR control preparation: Negative RT-qPCR control is water (molecular biology grade water, DNA/RNA free, DNase and RNase free). Prepare 1 mL aliquots in 1.5 mL sterile tubes to avoid contamination of stock bottles at the SARS-CoV-2 negative station. Store on the negative control bench at room temperature.

(B) Negative RNA extraction control preparation: Negative RNA extraction control is PBS buffer. Prepare 3 ml aliquots in 15 mL sample tubes and 5 mL sample tubes on the SARS-CoV-2 negative station. Store at the negative control bench at room temperature.

(C) Positive RNA Control STOCK SOLUTION Preparation: Twist Synthetic SARS-CoV-RNA Control 1 (MT007544.1) (Twist Bioscience, Cat #102019) comes at 1λ10^6 cp/µL concentration. Prepare diluted stock solutions for the training palette and qPCR controls and store the diluted stock solutions in −80° C. freezer. The positive RNA control is used both for the RNA standard curve in the training palette as well as positive RNA control in each RT-qPCR test run.

(C-a) ALIQUOTS FOR TRAINING PALETTE: Make 1:10 dilutions of original stock to 100,000 cp/µL by adding 100 µL of 1λ10^6 cp/µL stock to 900 µL DNase/RNase free water. Mix by vortexing briefly and centrifuge briefly to bring all liquid down to the bottom of the tube. Aliquot the 100,000 cp/µL solution into 25 µL aliquots in PCR tubes and store at −80 C freezer for training palette use (date and barcode the box containing these aliquots).

(C-b) ALIQUOTS FOR qPCR CONTROLS: Take one aliquot of 100,000 cp/µL stock and dilute to 1600 cp/µL by adding 204, of 100,000 cp/µL SARS-CoV-2 RNA solution in 1.230 mL of DNase/RNase free water in a 1.5 mL sterile tube. Mix by vortex and centrifuge briefly. Aliquot into 15 aliquots in PCR tubes and store in −80° C. for standard curve use (date and barcode the box containing these aliquots).

(D) TRAINING PALETTE CONTROLS WORKING SOLUTIONS Preparation: These 12 controls are prepared and aliquoted in 96 well plates (50 µl aliquots) and can be stored at −20° C. for several weeks. Each row of the plate will have a complete palette of 12 controls. The final full plate will have 8 rows of complete sets of 12. For each plate of controls a plate filled with $H_2O$ will need to be prepared.

To prepare 1 mL of each of the 12 solutions (enough for 2 full plates of controls) follow the procedure below:

(D-a) At the SARS-CoV-2 NEGATIVE station:

1. Use new gloves to avoid contaminating negative controls (gloves will be available at the negative station). Other standard PPE (lab coat, mask required).

2. Thaw on a rack the stock solutions of SARS, MERS and sCOV2 cDNAs 200,000 cp/µL (tubes form IDT). Mix tubes thoroughly once thawed.

3. Prepare 7 mL RP cDNA 2000 cp/µL solution in a 50 mL tube adding 704, of 200,000 cp/µL solution (tube from IDT) in 7 mL of sterile DNase, RNase free H2O. Pay attention not to touch the inside of the tube with the pipette.

4. Prepare 12 sterile 1.5 mL tubes and label them with numbers from 1 to 12.

5. Add the following volumes of sterile DNase, RNase free H2O in the tubes:

a. Tube 1 (water)=1 mL of H2O
b. Tube 2 (SARS cDNA)=0.5 mL of H2O
c. Tube 3 (MERS cDNA)=0.5 mL of H2O
d. Tube 4 (SARS-CoV-2 cDNA)=0.5 mL of H2O
e. Tube 5 (SARS-CoV-2 2K)=0.605 mL of H2O
f. Tube 6 (SARS-CoV-2 400)=0.5 mL of H2O
g. Tube 7 (SARS-CoV-2 400)=0.5 mL of H2O
h. Tube 8 (SARS-CoV-2 400)=0.5 mL of H2O
i. Tube 9 (SARS-CoV-2 400)=0.5 mL of H2O
j. Tube 10 (SARS-CoV-2 400)=0.5 mL of H2O
k. Tube 11 (SARS-CoV-2 400)=0.5 mL of H2O
l. Tube 12 (RP)=0.5 mL of H2O 6. Add 5 µL of SARS cDNA 200,000 cp/µL (tube from IDT) to Tube 2

7. Add 5 µL of MERS cDNA 200,000 cp/µL (tube from IDT) to Tube 3

8. Add 5 µL of sCOV2 cDNA 200,000 cp/µL (tube from IDT) to Tube 4

9. Return the stock SARS, MERS, CoV2 cDNA 200,000 cp/µl (tubes from IDT) tubes back to −20° C.

10. Move all the prepared 12 tubes and the RP 50 mL tube to the nCOV2 positive station using a "shuttle tube rack"

(D-b) On SARS-CoV-2 POSITIVE station:

1. Transfer the tubes from the "shuttle rack" to the nCOV2 positive station tube rack.

2. Bring back the "shuttle rack" to the end of the nCOV2 negative station.

3. Change gloves.

4. Thaw at room temperature a 25 µL aliquot of nCOV2 synthetic RNA 100,000 cp/µL (stored in 25 µL aliquots in −80° C.). Mix tubes thoroughly once thawed.

5. Add 20 µL of nCOV2 synthetic RNA 100,000 cp/µL to Tube 5.

6. Vortex and spin down the tube.

7. Add 125 µL from Tube 5 to Tube 6.

8. Vortex and spin down the tube.

Figure 3A:
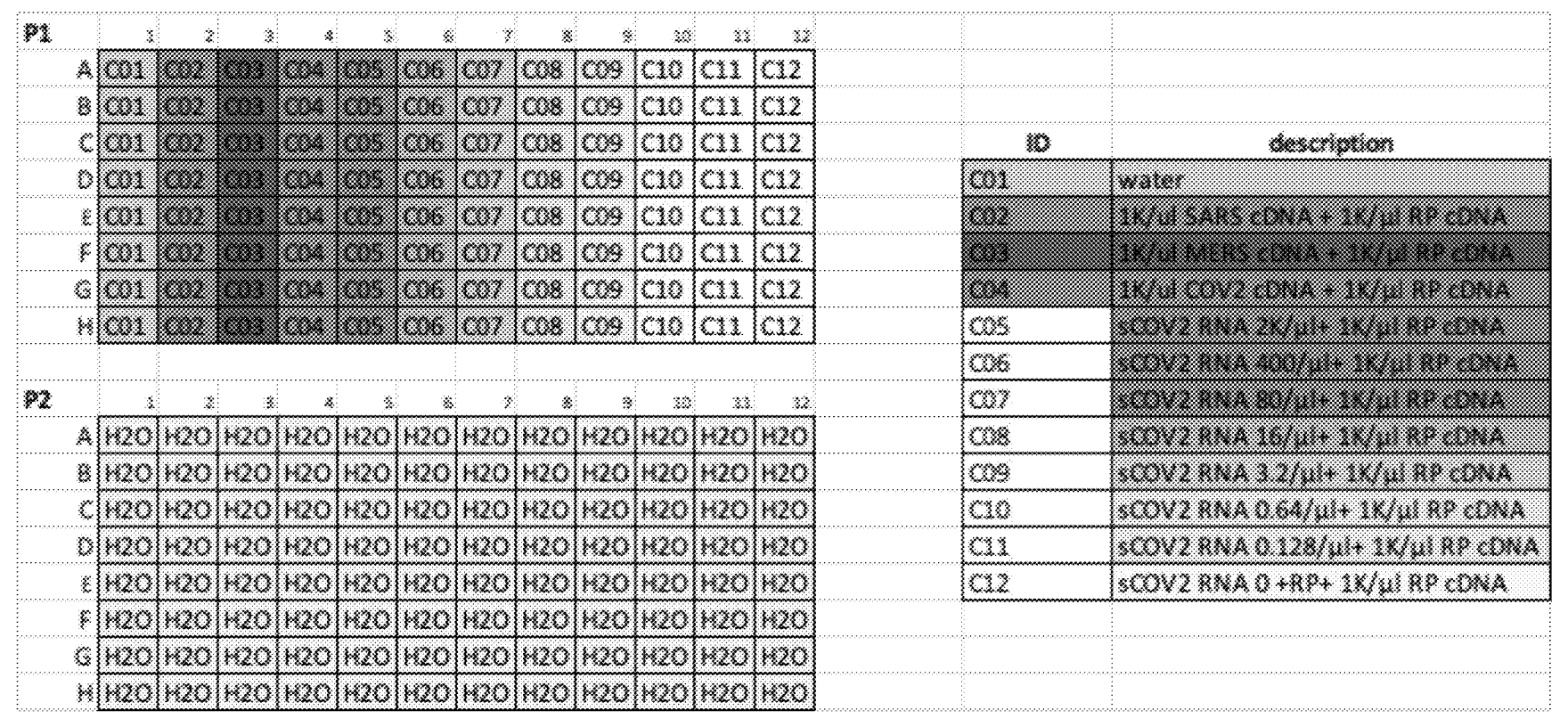

9. Add 125 µL from Tube 6 to Tube 7.
10. Vortex and spin down the tube.
11. Add 125 µL from Tube 7 to Tube 8.
12. Vortex and spin down the tube.
13. Add 125 µL from Tube 8 to Tube 9.
14. Vortex and spin down the tube.
15. Add 125 µL from Tube 9 to Tube 10.
16. Vortex and spin down the tube.
17. Add 125 µl from Tube 10 to Tube 11.
18. Vortex and spin down the tube.
19. Discard 125 µl from tube 11.
20. Add 0.5 mL of RP 2000 cp/µL (from the 50 ml tube previously prepared) in tube 2-12.
21. Mix by inverting each tube 2-3 times.
22. Spin down the tubes.
23. Add 50 µL of the solution from tube 1 to column 1 of 2 96 well plates.
24. Add 50 µL of the solution from tube 2 to column 2 of 2 96 well plates.
25. Add 50 µL of the solution from tube 3 to column 3 of 2 96 well plate.
26. Continue until the whole plate is full (see FIG. 3A).
27. Seal the 2 plates of controls and the 2 plates filled with sterile DNase, RNase free $H_2O$ and store them at −20° C. labelling them with content in the plate and the date of preparation using a marker.

Figure 3B:
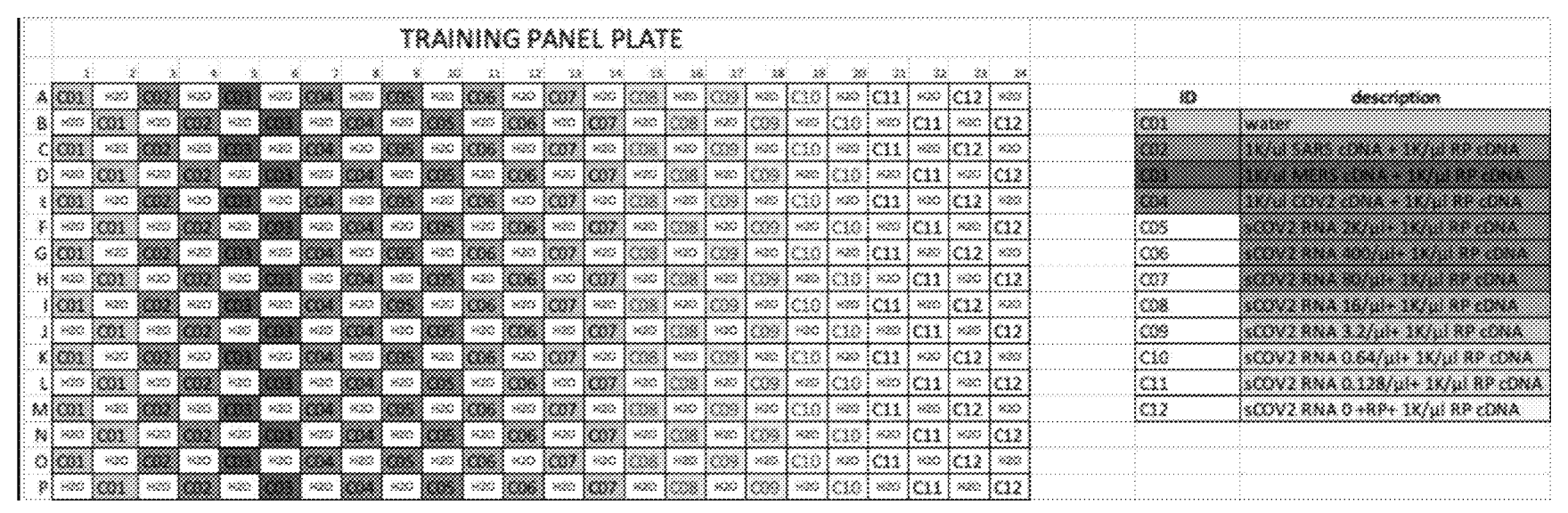

When used, each paired of control/$H_2O$ plates is thawed completely at room temperature, mix by vortexing and centrifuge at 3000× g for 1 minute, using the FeliX liquid dispenser, 54, of solution from each well is dispensed in a 384 qPCR plate prefilled with 5 µl of master mix. The control/$H_2O$ plates can be used to fill at least 4 384 qPCR plates using the layout shown in FIG. 3B.

(E) Controls for Each RT-Qpcr Run (Working Solutions)
4 controls are run in each RT-qPCR plate with patient samples and are added by the Echo to each 384 plate during dispense primers and probes. The controls are:
 1. Sterile DNase, RNAse free $H_2O$ (negative controls)
 2. 16 cp/µL nCOV2 synthetic RNA+1000 cp/mL RP cDNA (positive control 1)
 3. 3.2 cp/µL nCOV2 synthetic RNA+1000 cp/mL RP cDNA (positive control 2)
 4. 0.64 cp/µL nCOV2 synthetic RNA+1000 cp/mL RP cDNA (positive control 3)

These solutions will be prepared in batches and aliquoted in 5 tubes of PCR strips for each solution (2, 3, and 4). 70 µL of solution will be aliquoted in each tube. The 5 tubes PCR strips will be stored in barcoded empty PCR boxes (each containing a single type of solutions) stored in the positive control −20° C. freezer until use.

The below procedures are followed to make the Controls for RT-qPCR (enough for 1 Primer/Probes/Control PPC Echo source plate):

(E-a) On SARS-CoV-2 NEGATIVE station:
1. Use new gloves.
2. Prepare 600 µL of RP cDNA 2000 cp/µL by adding 6 µL of RP cDNA 200,000 cp/µL (tube from IDT) into a tube with (600 µL-6 µL) of sterile DNase/RNase free $H_2O$ (put 600 µL of water in the tube and then take out 6 µL).
3. Move the tube to the nCOV2 positive station using a "shuttle tube rack".

(E-b) on SARS-Cov-2 Positive Station:
1. Transfer the tubes from the "shuttle rack" to the SARS-CoV-2 positive station tube rack.
2. Bring back the "shuttle rack" to the end of the SARS-CoV-2 negative station.

3. Change gloves.
4. Thaw at room temperature a 10 µL aliquot of 1600 cp/µL SARS-CoV-2 synthetic RNA (the aliquot will thaw in less than a minute at room temperature; do not leave a tube at room temperature for more than 10 minutes before use).
5. Label 3 1.5 mL tubes writing 16, 3.2 and 0.64 on top of the cap.
6. Add the following volumes of sterile DNase, RNase free water in each of the 3 labelled tubes.
7. Tube 16=0.25 mL-5 µL (add 0.250 mL of water and then take out 5 µL.)
8. Tube 3.2=0.25 mL
9. Tube 0.64=0.25 mL
10. Add 5 µL of 1600 cp/µL SARS-CoV-2 synthetic RNA in Tube 16.
11. Vortex and spin down the tube.
12. Add 50 µL of solution from tube 16 to tube 3.2.
13. Vortex and spin down the tube.
14. Add 50 µL of solution from tube 3.2 to tube 0.64.
15. Vortex and spin down the tube.
16. Discard 50 µL of solution from tube 0.64.
17. Add 0.2 ml of RP 2000 cp/µL into each of the 3 tubes (Do not add RP in the water control).
18. Mix by inverting the tubes 3-4 times.
19. Vortex and spin down the tubes.

TO MAKE SOLUTIONS FOR MORE PLATES JUST MULTIPLY THESE AMOUNTS FOR THE NUMBER OF PLATES TO PREPARE

20. Prepare several strips of 5 PCR tubes.
21. With a multidispense pipette aliquot the 3 solutions in 70 µL aliquots in the 5 tubes PCR strips.
22. Store in separate empty barcoded PCR boxes separated by solutions (16, 3.2 and 0.64 cp/µL+RP 1K). Label the tubes with a different color marker (unless color coded tubes are already being used).
23. Store these single use aliquots at −20° C. until ready to use to make a PPC Echo plate.

(F) RNA Extraction Reagent Arraying on Apricot iPI-PETTEPRO
Prepare the reagents in SARS-CoV-2 negative work area. Please note, each reagent reservoir needs to be used to array at least 4 plates.

(F-i) Arraying Binding Solution plate (plate 2):
(F-i-a) Vortex the total nucleic acid magnetic beads until homogenous.
(F-i-b) Mix 220 mL binding solution with 8.46 mL total nucleic acid magnetic beads in a 250 mL bottle and add the well mixed solution to a fresh reagent reservoir. The solution will be enough to prepare four binding solution plates.
(F-i-c) Load the reagent reservoir and two 96 Deep Well plates to the iPIPETTEPRO plate shuttle. Dispense 550 µL binding solution to each well of the two plates.
(F-i-d) Remove the filled 96 well Deep Well plates and seal the plates with TempSeal sealing foil on Plateloc. Label the plate as plate 2, date of preparation, and operator initial. Store the plate at room temperature.
(F-i-e) Load two more 96 well Deep Well plates and Dispense 550 µL binding solution to each well of the two plates.
(F-i-f) Remove the filled 96 well Deep Well Plates and seal the plates with TempSeal sealing foil on Plateloc. Label the plate as plate 2, date of preparation, and operator initial. Store the plates at room temperature.
(F-i-g) If arraying more plates, repeat step b) through f) re-use the same reservoir. Otherwise, the reservoir can be disposed of in a biohazard waste container.

(F-ii) Arraying Wash Buffer plate (plate 3):

(F-ii-a) Dispense 200 mL Wash Buffer into a fresh reagent reservoir. This is enough to prepare two Wash Buffer plates.

(F-ii-b) Load the reservoir onto iPIPETTEPRO plate shuttle along with two 96-well Deep Well Plate. Dispense 1000 µL Wash Buffer to each well of the two Deep Well Plate.

(F-ii-c) Remove the two filled 96-well Deep Well Plate. Seal the plate with TempSeal Sealing foil on Plateloc. Label the plate as plate 3, date of preparation, and operator initial.

(F-ii-d) Dispense 200 mL Wash Buffer into the same reagent reservoir and repeat step b) and c).

(F-ii-e) If arraying more buffer 3 plates, repeat step a) through d) using the same reservoir. Otherwise, the reservoir can be disposed of in a biohazard waste container.

(F-iii) Arraying Ethanol Wash plate (plate 4):

(F-iii-a) Prepare 600 mL 80% Ethanol by mixing 120 mL DNase/RNase free water with 480 mL absolute Ethanol in a 1000 mL bottle (?). Cap the bottle tightly and mix by inverting the bottle 10-20 times.

(F-iii-b) Load a fresh reagent reservoir and two 96 well Deep Well Plate on to iPIPETTEPRO plate shuttle. Add 200 mL freshly prepared 80% Ethanol into the reagent reservoir. Dispense 750 µL 80% Ethanol into each well of the two plates.

(F-iii-c) Add 150 mL additional 80% Ethanol to the regent reservoir and dispense 750 µL 80% Ethanol into each well of the same two plates.

(F-iii-d) Remove the two filled plates and seal the plate with TempSeal sealing foil on Plateloc. Label the plates as Plate 4, date of preparation and operator initial. Store the plates at room temperature.

(F-iii-e) Add two new 96-well Deep Well plates to the iPIPETTEPRO plate shuttle. Add another 150 mL 80% Ethanol to the reagent reservoir. Dispense 750 µL 80% Ethanol to each well of the two plates.

(F-iii-f) Add the remaining 80% Ethanol to the reagent reservoir and dispense 750 µL 80% Ethanol into each well of the two plates.

(F-iii-g) Remove the two filled plates and seal the plate with TempSeal sealing foil on Plateloc. Label the plates as Plate 4, date of preparation and operator initial. Store the plates at room temperature.

(F-iii-h) If arraying more plates, repeat step a) through g) using the same reservoir. Otherwise, discard the reservoir into a biohazard waste container.

(F-iv) Arraying Elution Water plate (plate 5):

(F-iv-a) Add 45 mL DNase/RNase free water to a fresh reagent reservoir. Load the reagent reservoir and two 96 well Deep Well plate onto the iPIPETTEPRO plate shuttle. Dispense 50 DNase/RNase free water to each well of the two 96 well Deep Well plates.

(F-iv-b) Remove the two filled plates and seal the plate with TempSeal sealing foil on Plateloc. Label the plates as Plate 5, date of preparation and operator initials. Store the plates at room temperature.

(F-iv-c) Add two new 96 well Deep Well plates to the iPIPETTEPRO plate shuttle, dispense 100 µL DNase/RNase free water to each well of the two 96 well Deep Well Plates.

(F-iv-d) Remove the two filled plates and seal the plate with TempSeal sealing foil on Plateloc. Label the plates as Plate 5, date of preparation and operator initial. Store the plates at room temperature.

(F-iv-e) If arraying more plates, repeat step a) through d) using the same reservoir. Otherwise, discard the reagent reservoir in a biohazard waste container.

(G) Prepare Primer and Probes Stock Solution and Work Solutions:

Carry out the following procedure on SARS-CoV-2 negative station:

Prepare Primer and Probe Stock Solution: Upon receiving primers and probes, solubilize them to 250 µM stock solutions. Take the quantity in nmol printed on the primer and probe tubes (n), calculate the volume of H2O to use as: X=n*10/2.5 (or the same would be X=n*4). Resuspend primer and probe in X µL DNase/RNase free $H_2O$ to get 250 µM stock solution. Store the solubilized primers and probes at −20° C. negative freezer in the "PCR reagents preparation" room. Make sure that each tube is not frozen and thawed more than twice (label with an "X" on the tubes that have been thawed once already).

Prepare Primer/probe working solution: primers 45 µM/probes 11.25 µM made as following Tables 8-1, 8-2, and 8-3 (enough for one full Primers/Probes/Control Echo source plate):

TABLE 8-1

| Primers and Probes I | | | |
|---|---|---|---|
| PRIMER/PROBE (45 µM/11.25 µM) N1 WORKING SOLUTION (1200 µL total) | | X4 | X12 |
| 250 µM of Forward primer | 216 µL | 864 | 2592 |
| 250 µM of Reverse primer | 216 µL | 864 | 2592 |
| 250 µM of probe | 54 µL | 216 | 648 |
| H2O | 714 µL | 2856 | 8568 |
| Total | 1200 µL | 4800 | 14400 |

TABLE 8-2

| Primers and Probes II | | | |
|---|---|---|---|
| PRIMER/PROBE (45 µM/11.25 µM) N2 WORKING SOLUTION (1000 µL total) | | X4 | X12 |
| 250 µM of Forward primer | 180 µL | 720 | 2160 |
| 250 µM of Reverse primer | 180 µL | 720 | 2160 |
| 250 µM of probe | 45 µL | 180 | 540 |
| H2O | 595 µL | 2380 | 7140 |
| Total | 1000 µL | 4000 | 12000 |

TABLE 8-3

| Primers and Probes III | | | |
|---|---|---|---|
| PRIMER/PROBE (45 µM/11.25 µM) RP WORKING SOLUTION (700 µL total) | | X4 | X12 |
| 250 µM of Forward primer | 126 µL | 504 | 1512 |
| 250 µM of Reverse primer | 126 µL | 504 | 1512 |
| 250 µM of probe | 31.5 µL | 126 | 378 |
| H2O | 416.5 µL | 1666 | 4998 |
| Total | 700 µL | 2800 | 8400 |

The working solutions of Primers and Probes (PP) are aliquoted in 6 tube strips of color-coded PCR tubes. Aliquot N1, N2 and RP solutions in PCR tube strips with these volumes for each well:

N1 PP aliquots=96 µL/tube
N2 PP aliquots=76 µL/tube
RP PP aliquots=56 µL/tube

The aliquots are stored in empty tip boxes. The box should be labeled with the preparer's initials, date and a barcode.

In the Reagent database record for each box:
Date
Preparer's name
Type of primer stock solution (N1 250 µM, N2 250 µM, RP 250 µM)
  Barcode of the box
  Lot of the forward primers
  Lot of the reverse primers
  Lot of the probes
  Prepare Primer/Probe/Control (PPC) Echo source plate:
1) Retrieve from the "negative reagents" −20° C. freezer the following
  A) Two 6 tubes strips of N1 PP (primers/probes)
  B) Two 6 tubes strips of N2 PP
  C) Two 6 tubes strips of RP PP
Spin them down in a tip rack and leave them on a PCR tube rack on the negative station to thaw.
2) Retrieve from the "positive reagents" −20° C. freezer:
  A) One 5 tubes strip of 16 cp/µL+RP
  B) One 5 tubes strip of 3.2 cp/µL+RP
  C) One 5 tubes strip of 0.64 cp/µL+RP
Spin them down in a tip rack and leave them on a PCR tube rack on the positive station to thaw
3) Get a fresh 384 well Echo source plate and ON NEGATIVE STATION, with a P200 (bright yellow top) multichannel pipette add:
  A) 45 µL of N1 PP in row C starting from column 7
  B) 45 µL of N1 PP in row C starting from column 8
  C) 35 µL of N2 PP in row D starting from column 7
  D) 35 µL of N2 PP in row D starting from column 8
  E) 25 µL of RP PP in row E starting from column 7
  F) 25 µL of RP PP in row E starting from column 8
Do the same for row F, G and H following the scheme in FIG. 3C:
  G) Add 15 mL of DNase/RNase free H2O in a reservoir and with a multichannel pipette with 5 tips pipette 30 µL of the H2O in row J starting from column 8 and then column 9 (change tips after each pipetting)
  H) MOVE TO THE POSITIVE STATION where the controls are now thawed.
  I) Bring the scaffold with leftover water to the positive station
  J) With a multichannel pipette with 5 tips add the 16 cp/µL+RP control in row K starting from column 8 and then column 9 (change tips after each pipetting)
  K) With a multichannel pipette with 5 tips add the 3.2 cp/µL+RP control in row L starting from column 8 and then column 9 (change tips after each pipetting)
  L) With a multichannel pipette with 5 tips add the 0.64 cp/µL+RP control in row M starting from column 8 and then column 9 (change tips after each pipetting)
  M) Add 100 µL $H_2O$ (from the scaffold) in row A, B, O and P using a multichannel pipette N) Add 100 µL $H_2O$ in the empty wells of column 1, 2, 23, and 24.
4) Add a lid to the plate and spin it down at 3000× g for 1 minute.
5) Seal the plate with aluminum foil and pass the roller on top of it.
6) Add the date and the preparer's initial to the left side of the plate.
7) Store the plate in the negative 4° C., if used with 24 hours, or in the negative −20° C., if used after 24 hrs.
8) THIS PLATE CAN BE USED FOR 24 RUNS.

Example 5: RNA Extraction

Figure 4:
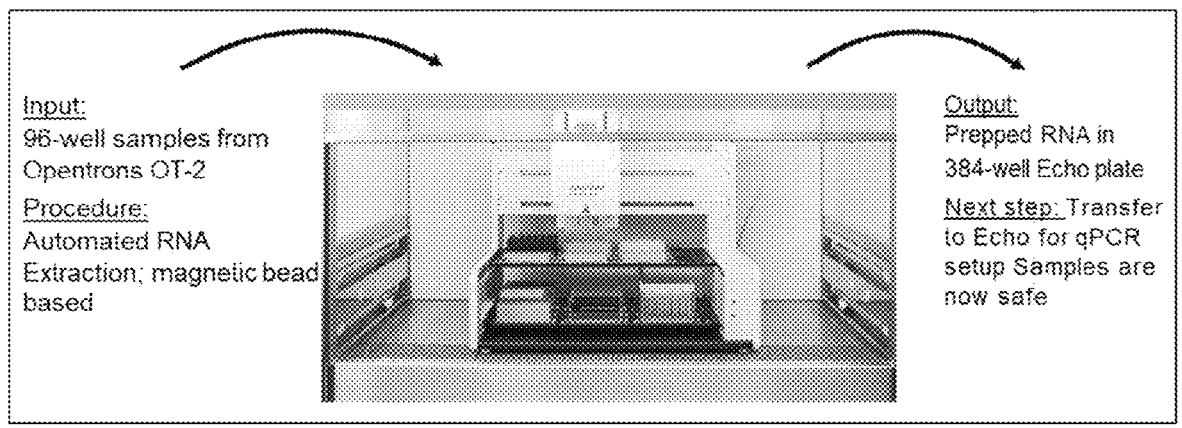
FIG. 4 depicts a schematic of RNA extraction procedure.

The procedure is for the purpose of extracting RNA from patient samples using a CyBio FeliX robot with the capability of extracting 96 samples in parallel (FIG. 4).

Figure 5:
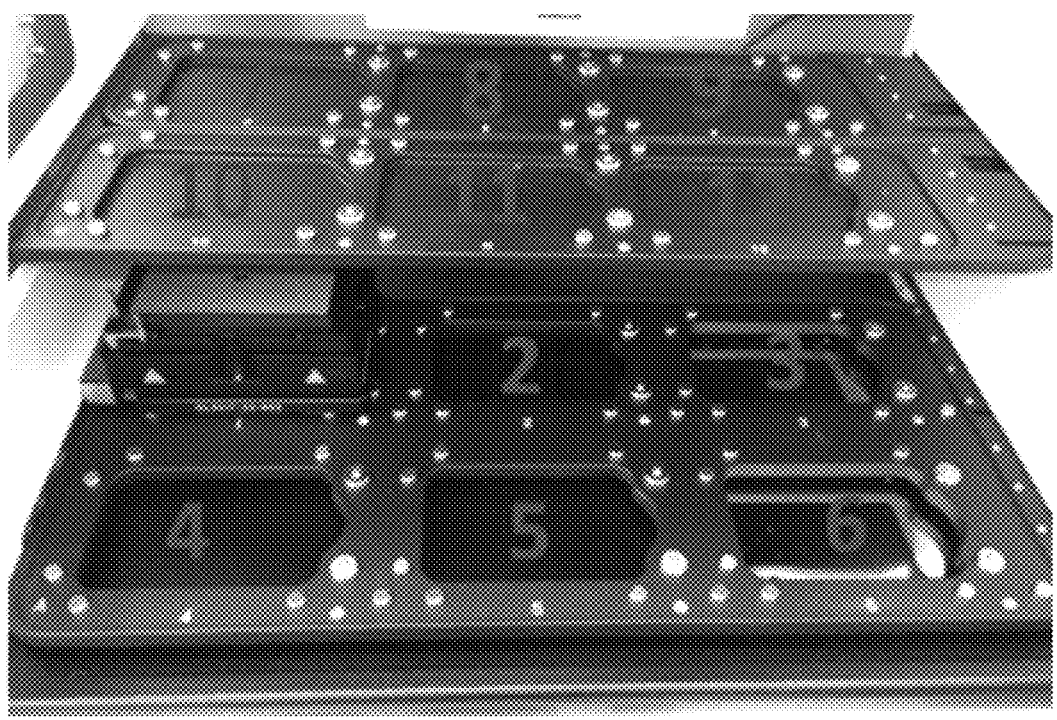
FIG. 5 shows an image depicting the deck positions for reagent plates and tip placements.

Material and Equipment:
CyBio Felix robot with 96 channel pipette head
Pre-reformatted 96 Deep Well Sample Plate
Reagent Plate 2
Reagent Plate 3
Reagent Plate 4
Reagent Plate 5
96-well skirted PCR plate
Barcoded 96-well skirted PCR plate
Two prefilled tip racks
Procedures:
The reagents and plates necessary for an extraction are pre-prepared and stored at room temperature at the RNA extraction bench. They must be arranged on the robot deck prior to the run.
Deck Preparation
(1) From the RNA extraction storage bench, obtain one of each of the following reagent plates:
  A. Plate 2—Binding (96 deep well plate)
  B. Plate 3—Wash (96 deep well plate)
  C. Plate 4—EtOH (96 deep well plate)
  D. Plate 5—Elution solution (96-well skirted PCR plate)
  E. Plate 6—Elution plate (96-well skirted PCR plate, barcoded)
(2) Obtain 2 pre-filled tip racks. Remove one tip from H1 position (lower left corner) from both racks.
(3) Obtain a reformatted sample plate, either directly from the reformatting run or from the 'Ready for RNA extraction' shelf in Fridge1. This is considered Plate 1.
(4) Remove the E-stop plug from the right side of the FeliX instrument. The decks can be now manually slide forward and back to facilitate placement of the reagent plates.
(5) Arrange the reagent plates and tips in the deck positions as in FIG. 5, taking care to ensure that they are securely positioned between the plate slot barriers:
Bottom Deck
  A. Position 4=Plate 1—Sample plate
  B. Position 5=Tip Rack 1
  C. Position 6=Tip Rack 2
Top Deck
  D. Position 7=Plate 2—Binding
  E. Position 8=Plate 3—Wash
  F. Position 9=Plate 4—EtOH
  G. Position 11=Plate 6—Elution plate
  H. Position 12=Plate 5—Elution solution
Felix Deck with plates and supplies for RNA extraction
(6) Ensure that Gripper is positioned on its mount in deck position 3, and the text 'Gripper' on the mount can be seen.
(7) Ensure that the magnet plate is positioned in deck position 10.
(8) Plug in the E-stop to its plug on the right side of the robot.
(9) In the Application Studio software of the FeliX laptop, select 'MagMAX MVPII RNA Extraction' to run the protocol.
(10) The deck arrangement will be prompted to be verified. Do so very carefully and thoroughly, taking care to verify the correct plates are in the correct deck positions and that they are all seated properly between the position barriers.
(11) Once verified, click 'Run'.
(12) The procedure will run for approximately 45 minutes.
(13) Monitor the run in the beginning of the run for 5 minutes before setting up another instrument and then check periodically to ensure completion without error.

(14) After the run, visually inspect the plate to make sure all wells have eluted samples as they should. Seal the 96-well elution plate and transfer to the 'Extracted RNA' shelf in Fridge1.

(15) Carefully discard the used reagent plates into appropriate waste streams. Plate 1 contains Guanidine and the content needs to be emptied into the hazardous chemical waste stream and Plate 4 contains ethanol and needs to be emptied into mixed ethanol waste. The emptied plates and all other reagent plates go into biohazard waste.

Example 6: Procedures for Manufacturing 384 Well Light Cycler Plates

This procedure is for manufacturing 384 well light cycler plates with RT-qPCR master mix and controls.

Material and Equipment:
One Step PrimeScript™ III RT-PCR Kit (TaKaRa Bio, Cat #RR600A)
PCR plate for LightCycler 480: Brooks Cat #4TI-0381
384 well plate for Echo source plate: Echo Qualified 384-Well Polypropylene Microplate 2.0 (LABCYTE INC. Cat #PP 0200, Lot #0006519165)
Control RNAs: Twist Synthetic SARS-CoV-2 RNA Control 1 (MT007544.1) (Twist Bioscience, Cat #102019)
Control cDNAs:
  2019-nCoV_N_Positive Control (Integrated DNA Technologies, Cat #10006625, Lot #509951) (For Training panel)
  Hs_RPP30 Positive Control (Integrated DNA Technologies, Cat #10006626, Lot #506769)
  MERS-CoV Control (Integrated DNA Technologies, Cat #10006623, Lot #508279) (For Training panel)
  SARS-CoV Control (Integrated DNA Technologies, Cat #10006624, Lot #507894) (For Training panel)
Cobra instrument
Procedure—Stepwise
Please wear clean gloves.
Cobra Preparation:

(1) Take out a new master mix 2× One Step PrimeScript III RT-qPCR Mix (RR600B) from the −20° C. freezer.

(2) Warm up the 2×master-mix (MM) to room temperature (20-25° C.) by leaving it on the bench for 15 min. Check that the temperature of the MM is in the acceptable range with a Noncontact Infrared Thermometer.

(3) Check that the waste container is not full. If full, empty it in the sink.

(4) Check that the wash bottle contains some water; if not fill it with sterile DNase/RNase free water (The empty water can be switched with a new one).

(5) Press the button on the pump for about 10 seconds to recirculate the wash water in the wash reservoir under the needles. One bottle of Takara III contains 50 mL of reagent that will be enough to dispense about 25 plates.

(6) Using the tracking computer in the room open the "plate manufacturing" file and add the relevant information for this session:
  a. Date
  b. Preparer's name
  c. Scan the 2D barcode of the Takara bottle being used.
  d. Scan the plates to be filled.
  f. Save the Document.

(7) Place the Costar plate on the multichannel Cobra dispense stage (Deck 1).

(8) Mark with a sharpie the front of the plate that will be dispensed; add the date of dispense and the preparer's initials.

Figure 6:
FIG. 6 shows an image depicting the placement of a 384 plate on Cobra instrument.

(9) Place a 384 plate on Deck 2 of the Cobra such that well A1 is oriented at the lower right-hand corner towards the operator, facing the clamp (the plate will be upside down for the operator) (see FIG. 6).

Cobra Dispensing Run:
NOTE: protocol optimized to dispense a batch of 384 PCR plates using the Bulk 4 Channel Cobra.
Open Protocol
1. Open the COBRA software
2. In the "Home" tab select "Initialize All."
3. After initialization go to the tab "Run".
4. Click the "Open" button and select the protocol: "Takara3_4CH_BULK_384.xml" (the only file on the desktop).
5. Check that:
  a. both "plate selection" fields on the top left, are on Dispense-384 PCR plate
  b. the Volume (µl) is set at 5.00 µl for each line (A, B, C and D)

Wash:
1. Make sure that the needles are on the wash reservoir. If not click on "Edit Channels"-* "prime/Purge"-* "Select . . . " and select "reservoir A". Click on "Move" and the needles will move to the top of the washing reservoir. To raise the needles, click on "select position" again and select "Home". Click on "Move"; the lines will raise a bit above the washing reservoir.
2. Connect a full water wash bottle to the line of the pressurized bottle (blue cap), switching the empty bottle with the full wash water bottle.
3. Click on the Edit Channel-* Prime/Purge.
4. Pressurize lines A, B, C and D by clicking on "pressurize" (the pump inside the COBRA will come off and the pressure will come up to about 15 psi).
5. Click "Fill" for each line and hold it until water comes out of the selected line and wash the line for about 10 seconds.
6. Do the same wash for all 4 lines.
7. With a KimWipe make sure there are not drops on the lines or on the metal needle holder; If there are, VERY GENTLY blot them with a KimWipe, never touching the needles directly with fingers. Also dry the top of the wash reservoir with a KimWipe.

Clean the Lines:
1. Click on the Edit Channel a Prime/Purge.
2. Depressurize the 4 lines clicking on "depressurize" (the sound of air coming out of the COBRA pump can be heard).
3. Connect the empty bottle to the pressurization line (blue cap).
4. Pressurize the 4 lines by again clicking on "pressurize."
5. Click "Fill" and hold it until all of the solution is expelled from the selected line (the sound of air coming out of the line can be heard when the solution is all out).
6. Do the same for all the lines.
7. With a KimWipe make sure there are no drops on the lines or on the metal needle holder; If there are, VERY GENTLY blot them with a KimWipe. Never touching the needles directly with fingers. Also dry the top of the wash reservoir with a KimWipe.

Prime Reagent:
1. Put a clean one-time use scaffold under the needles.
2. Pour the whole content of a TakaraIII bottle into a glass bottle (MM bottle).
3. Depressurize the 4 lines as described above.
4. Switch the empty bottle with the MM bottle.
5. Pressurize the lines as described above.

6. Click "Fill" and hold it until all the solution fills the whole line and is coming out of the needles into the scaffold.

7. Do the same for the 4 lines.

8. Put the scaffold on the side and cover it with a lid.

9. With a KimWipe make sure there are not drops on the lines or on the metal needle holder; If there are, VERY GENTLY blot them with a KimWipe, never touching the needles directly with fingers. Also dry the top of the wash reservoir with a KimWipe.

Dispense Reagent:

1. Click the "Back" button and go back to the "home" tab.

2. Place one 384 PCR plate on Deck 1 and one 384 PCR plate on Deck 2.

3. Make sure that there are no drops coming out of the needle. If there are, blot them gently with a KimWipe. If drops keep forming at the end of the needle(s) the COBRA will need to be serviced.

4. Click "Run."

5. Once the dispense is done, seal the plates.

6. Keep filling plates and seal them until done.

Final Steps:

1. Make sure that the needles are on the wash reservoir. If not click on "select position" and select "reservoir A". Click on "Move" and the needles will move above the washing reservoir. To raise the needles, click on "select position" again and select "Home". Click on "Move"; the lines will raise a bit above the washing reservoir.

2. When all plates are dispensed and sealed using the Plateloc and a peelable foil seal, store them in the allocated 4 C refrigerator close to the FeliX used to dispense RNA samples into the PCR plate.

3. Put the scaffold used at the beginning of the session (PRIME section of this SOP) and put it under the needles.

4. CLEAN THE LINES as described before.

5. When the lines are empty move the scaffold on the side and cover it with a lit.

6. WASH LINES with Water as described above.

7. CLEAN THE LINES as described above.

8. Close the software and leave the Cobra with EMPTY LINES until next session.

9. Pour the Takara reagent collected in the scaffold (about 8 ml) into the Takara III glass bottle. Store this botte (taped to the original bottle from the company) in the negative −20 C freezer. This leftover reagent can be used for the next session but JUST WITH TAKARA REAGENT WITH THE SAME LOT #.

Trouble Shooting:

1. If after dispensing the plates droplets can be seen outside the wells or very close to the edge of the wells, discard the plate. If the problem persists with the following plate, alert the lab manager. The COBRA will be re-serviced and reset for proper dispense.

2. If something goes wrong and it is necessary to CANCEL the run, click the CANCEL button that appears while the run is going. A window will ask if it's necessary to home the needles; click YES, UNLESS, for some reason the needles are INSIDE the washing reservoir. In that case click NO and re-initialize the COBRA going back to the HOME tab. Initialization will properly home the needles. After homing, if master mix is present in the lines (if master mix was being dispensed when the run was CANCELLED), pressurize the lines again and dispense some master mix in the waste, pressing "fill" for each of the 4 lines. After that it is ready to keep dispensing plates.

Example 7: Procedures for Dispensing RNAs Extracted from Samples

The procedure is for the purpose of dispensing RNA previously isolated from patient samples to a PCR master mix plate, using a CyBio FeliX robot with the capability of dispensing 96 samples in parallel.

Material and Equipments:

CyBio Felix robot with 96 channel pipette head

4× 96 well skirted RNA Plates (barcoded)

1× 384 well skirted LightCycler plate, prefilled with master mix and controls (barcoded)

4× prefilled tip racks

Procedures:

RNA plates containing isolated RNA are stored at 4 C in the Ready for PCR fridge. Pre-filled 384-well Lightcycler plates are stored at 4 C in the PCR plate fridge. They must be arranged on the FeliX deck prior to the run.

Deck Preparation (1) From the Ready for PCR fridge, obtain 4×RNA plates. (The fridges are clearly labeled and near the RNA extraction area).

(2) From the PCR plate fridge, obtain 1× pre-filled 384-well LightCycler plate.

(3) Remove the E-stop plug from the right side of the FeliX instrument. The decks can be now manually slide forward and back to facilitate placement of the plates and tips.

(4) Arrange the RNA and LightCycler plates and tips in the following deck positions, taking care to ensure that they are securely positioned between the plate slot barriers:

Bottom Deck a. Position 1=Tip Rack 1 b. Position 2=Tip Rack 2 c. Position 4=Tip Rack 3 d. Position 5=Tip Rack 4

Top Deck e. Position 7=RNA plate 1 f. Position 8=RNA plate 2 g. Position 10=RNA plate 3 h. Position 11=RNA plate 4 i. Position 12=384-well Lightcycler plate (5) Plug in the E-stop to its plug on the right side of the robot.

(6) In the Application Studio software of the FeliX laptop, select 'PCR RNA Dispense' to run the protocol.

(7) The deck arrangement will be prompted to be verified. Do so very carefully and thoroughly, taking care to verify the correct plates are in the correct deck positions and that they are all seated properly between the position barriers.

(8) Once verified, click 'Run'.

(9) The procedure will run for approximately 2 minutes.

(10) The procedure is very quick. Monitor the run for its entirety.

(11) Place a clear plastic lid on the Lightcycler plate.

(12) Remove and seal each RNA plate using the Plateloc next to the FeliX instrument.

(13) Transfer the lidded 384 well Lightcycler plate to the queue shelf for RT-qPCR.

(14) Transfer the RNA plates to the Post-PCR RNA Shelf in the Extracted RNA fridge.

(15) Carefully discard the used tips into the sharps disposal next to the FeliX station (see PRLNYC Lab waste policy).

Example 8: Multiplexed SARS-CoV-2 Testing

This procedure is for adding RNA samples to light cycler 384 well plate using Felix, adding Primers and Probes using Echo, performing multiplexed PCR test on light cycler 480 and reviewing and submitting test results to reporting software tools.

Definition:

MM: Master Mix

Material and Instruments:

One pre-dispensed light cycler 384-well reaction plate with Master Mix, controls and RNA samples added Pre-prepared Primer and Probe source plate with Primer and Probe working solution Echo Light cycler 480

10 µl tip box

Procedure—Stepwise

A. Primer/probe dispense with Echo

1. Thaw the primers/probes plate stored at −20 C as described in "PRL_SOP_ReagentPreparation". Vortex the plate briefly and centrifuge at 3000× g for 1 minute.

2. Retrieve Lightcycler 384 well plate (pre-dispensed with MM, controls, and filled with patient samples) from the queue shelf for RT-PCR. Centrifuge at 3000× g for 1 minute. Be very careful, while moving the plate, putting the plate in the centrifuge, or retrieving the plate from the centrifuge, not to knock or bump the plate as that could spill content in the microplate wells and cause cross contamination.

3. Recall the Echo dispense file to dispense in each well of a 384 LightCycler plate:

TABLE 9

Primer and Probe Mix

| Primer/probe target mix | Volume to be dispensed per well [nL] |
|---|---|
| N1-FAM | 70 |
| N2-HEX | 45 |
| RP-CY5 | 20 |

4. Run the dispense protocol providing the Echo with the source plate with primers/probes and the destination plate (LightCycler 384 well plate pre-dispensed with MM, controls and filled with patient samples) as follows:

Start Run

1) File>New

Source=384PP_AQ_BP2

Destination=LightCycler_384

Mapping Mode=Custom

2) Upload .csv files as follow in Source 1:

Select "Source 1" then click "File">"Import Region definition."

Select the specific dispense .csv file.

3) Optional: Click Run button (▶) and "Simulate" to simulate the run and check that the dispense files are correct.

4) If everything is correct Start Run clicking the Run button (▶).

6. When the Echo dispense has finished (about 2.5 minutes), position the plate on the heat sealer (PlateLok; Agilent) with clear sealer, making sure the appropriate metal stage is mounted on the sealer ("LC480" for 384 plates).

7. Heat seal the plate clicking "RUN" on heat sealer screen (seal for 2 seconds at 166° C.).

8. Centrifuge sealed plate at 4000× g for 3 min.

B. LightCycler 480

1. Turn on the cycler if not already on After initialization, the left indicator light should be green and the right indicator light, closest to the plate holder, should be red.

2. Press button close to right red light, eject stage, add new plate and press button again to re-insert stage with plate inside the light cycler. Right light now should now show green.

3. If the right indicator light is green before inserting the plate it means that a plate is already present in the machine. If that is the case, press button close to right green light, eject plate, discard it, add new plate and press button again to re-insert stage with plate inside the light cycler.

Start Run

1) Click "Run from MACRO"

2) Select "TAKARAIII_COVID_multiplex_50cycles"

3) Click "Start Run"

a) The run cycles are as follow (10 µl total volume):

Pre-incubation (1 cycle)=

RT=5 minutes at 52° C.

RT inactivation=10 seconds at 95° C.

Amplification (50 cycles)=

Melting=5 seconds at 95° C.

Annealing=30 seconds at 55° C. (acquisition of FAM, HEX and CY5 signals)

Cooling (1 cycle)=

Target temperature 40° C.

4. Save the file in the designated folder.

NOTE: The plate will be automatically named with the plateID of the barcode. The plate ID should also correspond to the name of the run file (these instructions should be already specified in the MACRO)

Analysis of Results

1. For each of the 3 detection channels (FAM/HEX/CY5) the MACRO will automatically:

1) apply "Abs Quant/Fit Points" and "2nd derivative" analysis.

2) select the correct "Color Comp" in the database.

2. Export the .xml file with Ct values using the export button.

Calculations

The Roche LightCycler 480 user software with "Abs quant/Fit-points" and "2nd derivative" analysis is used for the calculation of Ct values from each well. The threshold is automatically determined by the software and the efficiency is set as 2 (as for default parameters).

Reporting Results

A. Reference Ranges: rRT-PCR/RT-qPCR cycle threshold (Ct) values for the controls are typically within the range 30-40 for SARS-CoV-2 RNA and 10-40 for RPP30.

B. Procedure for Abnormal Results: For invalid results (see 11.2 below) samples are re-run. Ct values of positive and negative controls are recorded for each run. If the control samples deviate from usual values by more than 5 cycles, then the entire run is considered invalid.

Limitations of Procedure

This procedure is very flexible and can allow the use of different master mixes (once optimized for Cobra dispensing), samples from different origins (nasopharyngeal, nasal or oral swabs and saliva).

Performance Characteristics

A. Analytical Range: Ct values can range from 6 to 40.

B. Reportable Range: A human specimen control (RP) is considered positive at 6<Ct<40. Ct<40 is considered a positive signal from N1 and N2. Amplification curves that produce extremely low (10-20) or extremely high (40-50) Ct values will be manually observed by the operator to exclude abnormal qPCR amplification profiles indicative of untrustworthy results.

Patient samples: for a patient sample to be considered positive, positive signals must be obtained for either N1, and N2 primer pairs; a patient sample is negative if positive for RP and negative for both N1 and N2. Samples with negative for all N1, N2 and RP reactions are considered "invalid".

TABLE 10

| | | | Patient Samples | |
|---|---|---|---|---|
| N1 | N2 | RP | SARS Cov-2 interpretation | Action |
| + | + | +/− | Detected | Report Positive |
| − | − | + | Not detected | Report Negative |
| + | − | +/− | Detected | Report Positive |
| − | + | +/− | Detected | Report Positive |
| − | − | − | Invalid | Retest |

C. Sensitivity: LoD for SARS-CoV-2 is 200 virus/mL of specimen, with RNA extraction using the MagMAX Viral/Pathogen II Kit (Applied Biosystems).

D. Precision: pending verification.

Example 9: Comparison Between Adding Primers & Probes to Master Mix Versus to Amplification Mixture Primers and probes (PP) targeting two separate regions of the viral nucleocapsid (N) gene of SARS-CoV-2 (N1, N2) and a control human gene (RP) were mixed with 1 step RT-qPCR master mix (MM). The solution was dispensed in the bottom 8 rows of two light cycler (LC) 384 well plates. MM without PP was dispensed in the top 8 rows of the same two LC plates. After approximately 30 minutes serial dilutions of synthetic SARS-CoV-2 RNA (5 µl) were dispensed in the prepared LC plates. Concentrated PP were dispensed on the top 8 rows of the LC plates so that final reaction concentration of PP is the same for the whole plate. The plates were run in a LC following SCV2 test as described in Example 1 and rRT-PCR/RT-qPCR cycle threshold (Ct) values were collected using 2nd Derivative analysis.

Figure 11:
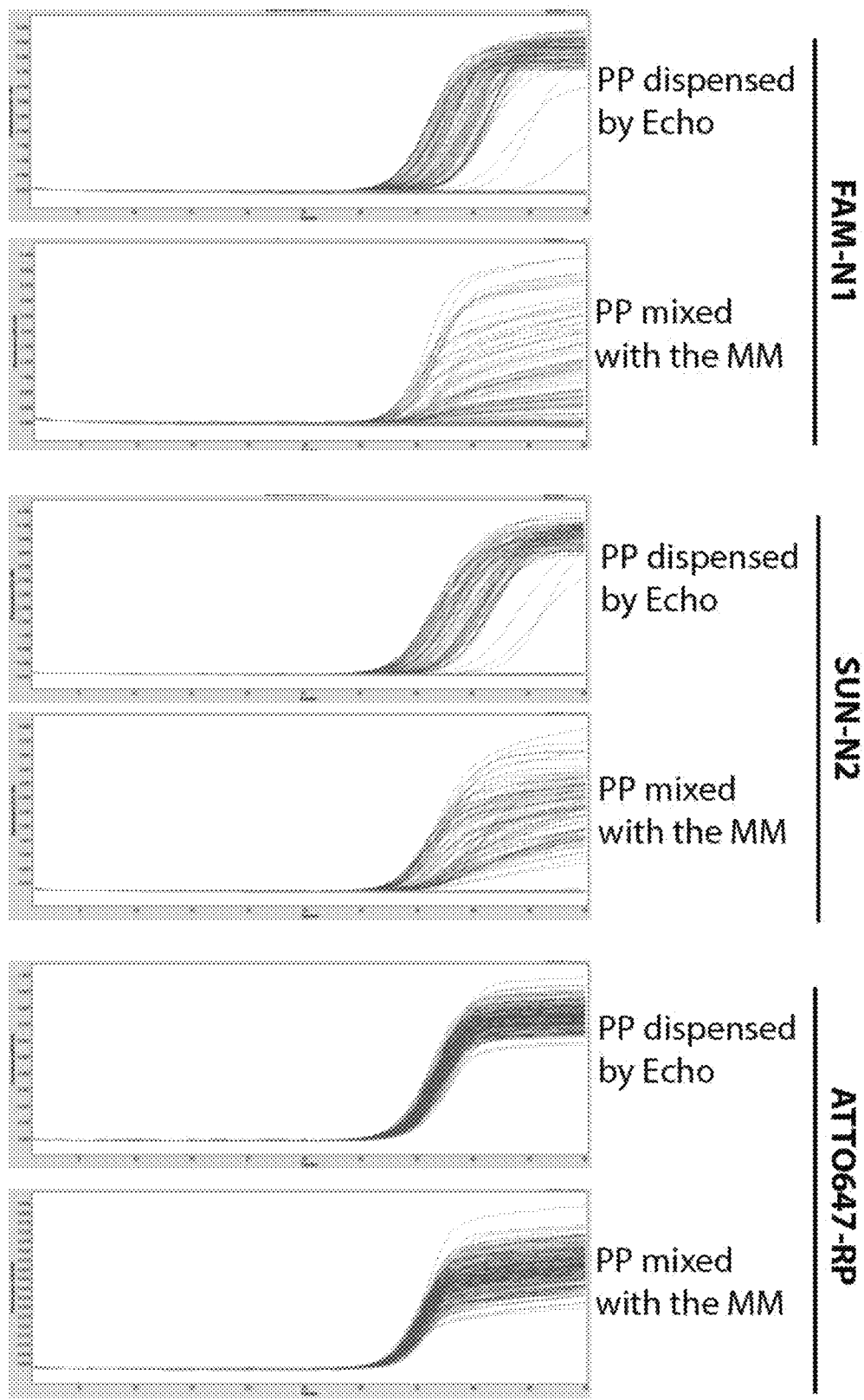
FIG. 11 depicts graphs demonstrating comparison of amplification curves of SCV2 tests performed with primers and probes (PP) separately dispensed with Echo and SCV2 tests performed with PP mixed into the master mix (MM). FAM-N1: primers and probes targeting SARS-CoV-2 N gene (N nucleotide 14-85), SUN-N2: primers and probes targeting SARS-CoV-2 N gene (N nucleotide 890-957), ATT0647-RP: primers and probes targeting a control human gene, RP.

Amplification curves of the same dilutions showed a much less variable and efficient PCR amplification for reaction using PP dispensed using an Echo right before the start of the RT-qPCR run. As shown in FIG. 11, these differences were very evident for both N1 and N2 PP and less evident for the RP PP.

The mixing of PP to MM also increased the number of samples with lower RNA concentrations for which SARS-CoV-2 was not detected (false negatives). As shown in FIG. 12, the number of positive reactions among the 32 replicates of each of the dilution was mostly higher in reaction with PP dispensed with the echo compared to reaction with PP mixed in the MM.

Example 10: Limit of Detection (LoD) Experiment 22 serial dilutions of SARS-CoV-2 synthetic RNA from 32 copies/µl to 0.02 copies/µl were prepared and analyzed with SCV2 test as described in Example 1 for SARS-CoV-2 quantification. rRT-PCR/RT-qPCR cycle threshold (Ct) values were collected after RT-qPCR reaction to determine the PCR limit of detection (LoD) of the test, defined as the lowest concentration of RNA detected at least 95% of the times among the replicates of that specific concentration (64 replicates for each concentration of RNA were used).

The SCV2 test has a PCR LoD of 1 copy/µl (=5 copies/reaction). As shown in FIG. 13, 98.4% of the reactions containing 1 copy/µl of SARS-CoV-2 RNA were indeed positive and produced an average Ct value of 36.7±1.0 for N1 and 37.2±1.0 for N2. SARS-CoV-2 at concentrations lower than 1 copy/µl (5 copies/reaction) were still detected by SCV2 test with a frequency of detection decreasing with decreased virus concentration. The SCV2 test was able to detect down to 0.02 copies/µl (=0.1 copies/reaction) of virus in 7.81% of reactions suggesting an almost 100% efficiency of amplification; 0.1 copies can be in theory detected in 1 of 10 reactions because one copy of virus can be present only in one of 10 wells. The empirical validation showed that SCV2 test can detect 1 copy of virus in one of 13 reactions indicating that the test efficiency is virtually at the physical limitation of the PCR assay.

The examples and embodiments described herein are for illustrative purposes only and various modifications or changes suggested to persons skilled in the art are to be included within the spirit and purview of this application and scope of the appended claims.

What is claimed is:

1. A method of detecting a target nucleic acid sequence in a sample, said method comprising:
contacting said sample with at least one microdroplet comprising a pair of primers and a probe, wherein said at least one microdroplet comprising said pair of primers and said probe contains a volume equal to or less than 250 nL, wherein said at least one microdroplet comprises said pair of primers and said probe at a concentration of at least 1 µM; and amplifying said target nucleic acid sequence in said sample, thereby detecting said target nucleic acid sequence in said sample, wherein said amplification comprises polymerase chain reaction thermocycling.

2. The method of claim 1, comprising contacting said sample with two or more microdroplets each comprising said pair of primers, wherein each of said two or more microdroplets has a volume of 2.5 nL or 25 nL.

3. The method of claim 1, wherein said target nucleic acid sequence is DNA, optionally wherein said target nucleic acid sequence is viral DNA, optionally further wherein said viral DNA is from hepatitis B, adenovirus, papillomavirus, poxvirus, herpesvirus, herpes simplex virus, varicella zoster virus, Epstein-Barr virus, or cytomegalovirus.

4. The method of claim 3, wherein said DNA comprises DNA from a bacterium, a fungus, or a parasite, optionally wherein said bacterium comprises *Streptococcus pyogenes*, coliform, *Escherichia coli*, *Salmonella*, *Shigella*, *Staphylococcus aureus*, *Gardnerella vaginalis*, *Neisseria gonorrhoeae*, *Chlamydia trachomatis*, *Treponema pallidum*, *Clostridium difficile*, *Mycobacterium tuberculosis*, *Bordetella pertussis*, *Streptococcus pneumoniae*, *Mycoplasma pneumoniae*, *Haemophilus influenzae*, *Legionella pneumophila*, *Neisseria meningitidis*, *Listeria monocytogenes*, *Borrelia burgdorferi*, *Vibrio cholerae*, *Clostridium botulinum*, *Clostridium tetani*, or *Bacillus anthracis*, optionally wherein said fungus comprises *Candida albicans*, *Trichophyton*, *Microsporum*, *Epidermophyton*, *Trichophyton rubrum*, *Epidermophyton floccosum*, *Aspergillus*, *Histoplasma capsulatum*, *Cryptococcus neoformans*, *Cryptococcus gattii*, *Coccidioides* or *Blastomyces*, optionally further wherein said parasite comprises a protozoa, a helminth, or an ectoparasite.

5. The method of claim 1, wherein said target nucleic acid sequence comprises a nucleic acid from severe acute respiratory syndrome coronavirus 2 (SARS-CoV-2), human immunodeficiency virus (HIV), influenza virus, Dengue virus, hepatitis C virus, hepatitis E virus, ebolavirus, lyssavirus, poliovirus, West Nile virus, Human T-cell lymphotropic virus type 1 (HTLV-1), respiratory syncytial virus (RSV), parainfluenza virus (NV), human metapneumovirus (hMPV), human rhinovirus (HRV), severe acute respiratory syndrome coronavirus 1 (SARS-CoV-1), middle east respiratory syndrome coronavirus (MERS-CoV), or measles virus.

6. The method of claim 1, wherein said amplification is performed in a reaction mixture.

7. The method of claim 6, wherein said reaction mixture has a volume of about 0.5 to about 20 µL.

8. The method of claim 6, wherein said reaction mixture comprises a polymerase, deoxynucleotide triphosphates (dNTPs), DNAse/RNAse-free water, or an amplification buffer, optionally wherein said polymerase comprises a DNA-dependent DNA polymerase or an RNA-dependent DNA polymerase.

9. The method of claim 6, wherein said reaction mixture comprises a reverse transcriptase.

10. The method of claim 1, wherein said amplification has at least 91% sensitivity relative to a positive control amplification or at least 91% sensitivity relative to a negative control amplification.

11. The method of claim 1, wherein said amplification has a lower limit of detection (LoD) of 10-200 molecules per mL as determined by amplification with standard positive controls.

12. The method of claim 1, wherein said detection has a lower limit of detection (LoD) of 100-2000 molecules per mL as determined by amplification with standard positive controls.

13. The method of claim 1, wherein said sample is extracted from a biological sample.

14. The method of claim 13, wherein said biological sample comprises nasopharyngeal fluid, oropharyngeal fluid, saliva, blood, sera, plasma, lavage, urine, ear exudate, cerebrospinal fluid (CSF), sputum, saliva, bone marrow, synovial fluid, aqueous humor, amniotic fluid, cerumen, breast milk, auroral pharyngeal lavage fluid, bronchoalveolar lavage, bronchoalveolar lavage fluid, semen, prostatic fluid, Cowper's fluid, pre-ejaculatory fluid, female ejaculate, sweat, tears, cyst fluid, pleural fluid, peritoneal fluid, pericardial fluid, lymph, chyme, chyle, bile, interstitial fluid, menses, pus, sebum, vaginal secretion, mucosal secretion, stool, stool water, pancreatic juice, lavage fluid from sinus cavities, bronchopulmonary aspirate, blastocoel cavity fluid, or umbilical cord blood, further wherein said biological sample is obtained from a human subject, optionally further wherein said biological sample is treated with N-acetylcysteine (NAC) before each of said plurality of samples is extracted from said biological sample, optionally further wherein said biological sample is heat-inactivated before each of said plurality of samples is extracted.

* * * * *

SEQUENCE LISTING

<160> NUMBER OF SEQ ID NOS: 9

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gaccccaaaa tcagcgaaat           20

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
tctggttact gccagttgaa tctg           24

```
<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
accccgcatt acgtttggtg gacc                                              24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttacaaacat tggccgcaaa                                                   20

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcgcgacatt ccgaagaa                                                     18

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
acaatttgcc cccagcgctt cag                                               23

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agatttggac ctgcgagcg                                                    19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagcggctgt ctccacaagt                                                   20
```

```
<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
ttctgacctg aaggctctgc gcg                                              23
```